US012697349B2

(12) United States Patent
Huang et al.

(10) Patent No.: US 12,697,349 B2
(45) Date of Patent: Aug. 4, 2026

(54) COMPOSITIONS AND METHODS FOR TREATING RAS-MUTANT CANCERS

(71) Applicants: MEMORIAL SLOAN KETTERING CANCER CENTER, New York, NY (US); ALGEN BIOTECHNOLOGIES, INC., San Francisco, CA (US)

(72) Inventors: Chun-Hao Huang, San Francisco, CA (US); Spencer Charles Knight, San Francisco, CA (US); Scott Lowe, New York, NY (US)

(73) Assignees: Memorial Sloan Kettering Cancer Center, New York, NY (US); Algen Biotechnologies, Inc., San Francisco, CA (US)

( * ) Notice: Subject to any disclaimer, the term of this patent is extended or adjusted under 35 U.S.C. 154(b) by 882 days.

(21) Appl. No.: 17/604,864

(22) PCT Filed: Apr. 23, 2020

(86) PCT No.: PCT/US2020/029513
§ 371 (c)(1),
(2) Date: Oct. 19, 2021

(87) PCT Pub. No.: WO2020/219668
PCT Pub. Date: Oct. 29, 2020

(65) Prior Publication Data
US 2022/0193109 A1 Jun. 23, 2022

Related U.S. Application Data

(60) Provisional application No. 62/838,065, filed on Apr. 24, 2019.

(51) Int. Cl.
| | |
|---|---|
| *A61K 31/7088* | (2006.01) |
| *A61K 31/4412* | (2006.01) |
| *A61K 31/519* | (2006.01) |
| *A61K 31/7068* | (2006.01) |
| *A61K 31/7135* | (2006.01) |
| *A61P 35/00* | (2006.01) |
| *C12N 15/113* | (2010.01) |
| *G01N 33/50* | (2006.01) |

(52) U.S. Cl.
CPC ...... *A61K 31/7088* (2013.01); *A61K 31/4412* (2013.01); *A61K 31/519* (2013.01); *A61K 31/7068* (2013.01); *A61K 31/7135* (2013.01); *A61P 35/00* (2018.01); *C12N 15/1137* (2013.01); *G01N 33/5091* (2013.01); *C12N 2310/14* (2013.01); *C12N 2310/531* (2013.01); *C12N 2320/31* (2013.01); *G01N 2333/90212* (2013.01)

(58) Field of Classification Search
CPC .............. A61K 31/336; A61K 31/7068; A61K 31/7088; A61K 31/7135; A61P 35/00
See application file for complete search history.

(56) References Cited

U.S. PATENT DOCUMENTS

| | | | |
|---|---|---|---|
| 2007/0050146 A1 | 3/2007 | Bentwich et al. | |
| 2020/0222407 A1* | 7/2020 | Lipford .............. | A61K 39/3955 |

FOREIGN PATENT DOCUMENTS

| | | |
|---|---|---|
| JP | 2017-527582 A | 9/2017 |
| JP | 2017-527583 A | 9/2017 |
| JP | 2019-031476 A | 5/2018 |
| WO | WO-2009/114126 A1 | 9/2009 |
| WO | WO-2014/122599 A1 | 8/2014 |
| WO | WO-2014/143855 A2 | 9/2014 |
| WO | WO-2017/027359 A1 | 2/2017 |
| WO | WO-2018/145090 A1 | 8/2018 |
| WO | WO-2018/218087 A1 | 11/2018 |

OTHER PUBLICATIONS

Ramanathan (Clin Cancer Res 2007;13(7), Apr. 1, 2007, pp. 2109-2114).*
FDA (Am J Health-Syst Pharm, vol. 52, May 1, 1995; p. 931).*
International Search Report and Written Opinion on PCT PCT/US2020/029513 mailed Aug. 17, 2020.
Perez et al. "Antineoplastic effects of auranofin in human pancreatic adenocarcinoma preclinical models," Surgery Open Science, Jul. 3, 2019 (Jul. 3, 2019). vol 1. Iss. 2, pp. 56-63. entire document.
Mou Haiwei et al: "Genetic disruption of oncogenic Kras sensitizes lung cancer cells to Fas receptor-mediated apoptosis", Proceedings of the National Academy of Sciences, vol. 114, No. 14, Apr. 4, 2017 (Apr. 4, 2017), pp. 3648-3653, XP093045775, ISSN: 0027-8424, DOI: 10.1073/pnas.1620861114 Retrieved from the Internet: URL:https://www.ncbi.nlm.nih.gov/pmc/articles/PMC5389295/pdf/pnas.201620861.pdf> p. 3651, left column, paragraph 3—right column, paragraph 1; * abstract*.
Randhawa H. et al: "Activation of ERK signaling and induction of colon cancer cell death by piperlongumine", Toxicology in Vitro., vol. 27, No. 6, Sep. 1, 2013 (Sep. 1, 2013), pp. 1626-1633, XP093045839, GB ISSN: 0887-2333, DOI:10.1016/j.tiv.2013.04.006 Retrieved from the Internet: URL:https://www.ncbi.nlm.nih.gov/pmc/articles/PMC3749270/pdf/nihms481162.pdf> p. 6, paragraph 2; * abstract; figure 1 *.
Seung-Min Shin et al: "Antibody targeting intracellular oncogenic Ras mutants exerts anti-tumour effects after systemic administration", Nature Communications, vol. 8, May 10, 2017 (May 10, 2017), pp. 1-14, XP055434123, DOI: 10.1038/ncomms15090 age 4, right column, paragraph 2; *abstract*.

(Continued)

*Primary Examiner* — Pancham Bakshi
(74) *Attorney, Agent, or Firm* — Foley & Lardner LLP

(57) ABSTRACT

The present disclosure relates generally to compositions and methods for the treatment of a RAS-mutant cancer. In particular, the present technology relates to administering a therapeutically effective amount of one or more TXNRD1 inhibitors to a subject diagnosed with, or at risk for a RAS-mutant cancer (e.g., RAS-mutant pancreatic cancer).

9 Claims, 29 Drawing Sheets

Specification includes a Sequence Listing.

(56)                    References Cited

OTHER PUBLICATIONS

Yuki Yamaguchi et al: "Piperlongumine rapidly induces the death of human pancreatic cancer cells mainly through the induction of ferroptosis", International Journal of Oncology, Jan. 31, 2018 (Jan. 31, 2018), XP055552921, GR ISSN: 1019-6439, DOI: 10.3892/ijo. 2018.4259 p. 1011, right column, paragraph 1; * abstract; figures 2-3 *.

Chen, Xiang, et al., Targeting Oxidative Stress in Embryonal Rhabdomyosarcoma, Cancer Cell 24, 710-724, Dec. 9, 2013, Elsevier Inc.

Hrabe, et al., Disruption of thioredoxin metabolism enhances the toxicity of transforming growth factor B-activated kinase 1 (TAK1) inhibition in KRAS-mutated colon cancer cells, Redox Biology 5 (2015) 219-327.

Yan, et al., Inhibition of Thioredoxin/Thioredoxin Reductase Induces Synthetic Lethality in Lung Cancers with Compromised Glutathione Homeostasis, Molecular Cell Biology, Cancer Research, doi: 10.11S8/0008-5472.CAN-18-1938.

Yoo, Min-Hyuk, et al., Targeting Thioredoxin Reductase 1 Reduction in Cancer Cells Inhibits Self-Sufficient Growth and DNA Replication, PLoS One; www.plosone.org. Oct. 2007, Issue 10, e1112.

Chen Xiang et al: "Targeting Oxidative Stress in Embryonal Rhabdomyosarcoma", Cancer Cell, vol. 24, No. 6, Dec. 1, 2013 (Dec. 1, 2013), pp. 710-724, XP093008612, US ISSN: 1535-6108, DOI: 10.1016/j.ccr.2013.11.002.

Hrabe Jennifer E. et al: "Disruption of thioredoxin metabolism enhances the toxicity of transforming growth factor [beta]-activated kinase 1 (TAKI) inhibition in KRAS-mutated colon cancer cells", Redox Biology, vol. 5, Jun. 18, 2015 (Jun. 18, 2015), pp. 319-327, XP093008292.

Powis et al., "Thioredoxin signaling as a target for cancer therapy", Current Opinion in Pharmacology, vol. 7, No. 4, pp. 392-397, 2007.

Misale et al., "KRAS G12C NSCLC Models are Sensitive to Direct Targeting Of KRAS in Combination with PI3K Inhibition," Clin Cancer Res, Jan. 2019, vol. 25, (13, pages).

* cited by examiner

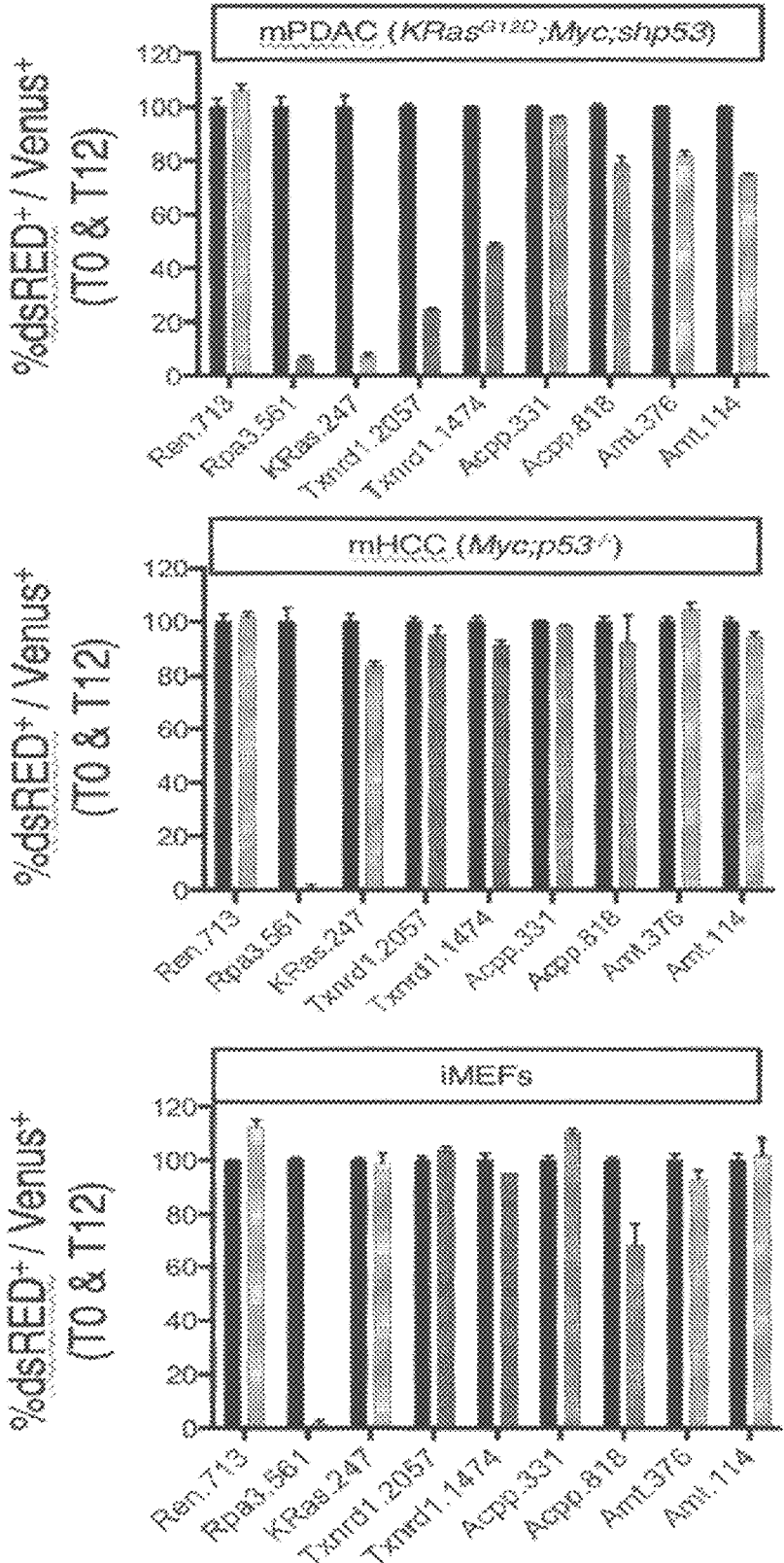

SEQUENCE LISTING

<160> NUMBER OF SEQ ID NOS: 29

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tctaatatca ttaacaccat gg                                           22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
taaataaaac tgaatatggt ca                                           22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ttaataataa cttatgatat ta                                           22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tttgtaacaa aaatacatgg aa                                           22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tttaaatgaa aatccttcac at                                           22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ttttaaatga aaatccttca ca                                           22

```
<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
taagaaaaga gaatcacaac at                                              22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttttcattta tcttcacccc ta                                              22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ttagaaagaa atagataccc aa                                              22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
taataataac ttatgatatt aa                                              22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tttagtcaca gggtaattcg tc                                              22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttcgtcactg acaacgttgt ga                                              22
```

-continued

```
<210> SEQ ID NO 13
<211> LENGTH: 3969
<212> TYPE: DNA
<213> ORGANISM: Homo sapiens

<400> SEQUENCE: 13
agaccctcac gtgatgacaa cagctagcaa agttctgtag ctactgcctt agggcatagt      60
ctaatttctt cagtaaaaac acacttattc caaatttggt tccagaattg ccttaaattg     120
tttttgctct gttcttaggt tgggggcggc tatgagcagg cagaggatgt ggtgtcaccc     180
aattaggagc tctcagctta cgaggcaatt agcataggtt gccagggctg cacgaggagt     240
ggatttctgc tttgtcattc tgactctggc agttagcccg cccgctcggc gcagggcgtg     300
gcttctcgta gccattagga aacagcaacc ctttcacctc agttttcttc actccggcat     360
ttgcagcaga gcgaaaggtg gtcgagtcct gaaggagggc ctgatgtctt catcattctc     420
aaattcttag gacggtcggg ccctggaagg aacgctctcg gaattggccg cggaaaccga     480
tctgcccgtt gtgtttgtga aacagagaaa gataggcggc catggtccaa ccttgaaggc     540
ttatcaggag ggcagacttc aaaagctact aaaaatgaac ggccctgaag atcttcccaa     600
gtcctatgac tatgacctta tcatcattgg aggtggctca ggaggtctgg cagctgctaa     660
ggaggcagcc caatatggca agaaggtgat ggtcctggac tttgtcactc ccacccctct     720
tggaactaga tggggtctcg gaggaacatg tgtgaatgtg ggttgcatac ctaaaaaact     780
gatgcatcaa gcagctttgt taggacaagc cctgcaagac tctcgaaatt atggatggaa     840
agtcgaggag acagttaagc atgattggga cagaatgata gaagctgtac agaatcacat     900
tggctctttg aattggggct accgagtagc tctgcgggag aaaaaagtcg tctatgagaa     960
tgcttatggg caatttattg gtcctcacag gattaaggca acaaataata aaggcaaaga    1020
aaaaatttat tcagcagaga gatttctcat tgccactggt gaaagaccac gttacttggg    1080
catccctggt gacaaagaat actgcatcag cagtgatgat cttttctcct tgccttactg    1140
cccgggtaag accctggttg ttggagcatc ctatgtcgct ttggagtgcg ctggatttct    1200
tgctggtatt ggtttagacg tcactgttat ggttaggtcc attcttctta gaggatttga    1260
ccaggacatg gccaacaaaa ttggtgaaca catggaagaa catggcatca gtttataag    1320 acagttcgta ccaattaaag ttgaacaaat tgaagcaggg acaccaggcc gactcagagt    1380
agtagctcag tccaccaata gtgaggaaat cattgaagga gaatataata cggtgatgct    1440
ggcaatagga agagatgctt gcacaagaaa aattggctta gaaaccgtag gggtgaagat    1500
aaatgaaaag actggaaaaa tacctgtcac agatgaagaa cagaccaatg tgccttacat    1560
ctatgccatt ggcgatatat ggaggataa ggtggagctc acccagttg caatccaggc    1620 aggaagattg ctggctcaga ggctctatgc aggttccact gtcaagtgtg actatgaaaa    1680
tgttccaacc actgtatta ctcctttgga atatggtgct tgtggccttt ctgaggagaa    1740
agctgtggag aagtttgggg aagaaaatat tgaggtttac catagttact tttggccatt    1800
ggaatggacg attccgtcaa gagataacaa caaatgttat gcaaaaataa tctgtaatac    1860
taaagacaat gaacgtgttg tgggctttca cgtactgggt ccaaatgctg agaagttac    1920 acaaggcttt gcagctgcgc tcaaatgtgg actgaccaaa aagcagctgg acagcacaat    1980
tggaatccac cctgtctgtg cagaggtatt cacaacattg tctgtgacca agcgctctgg    2040
ggcaagcatc ctccaggctg ctgctgagg ttaagcccca gtgtggatgc tgttgccaag    2100
actgcaaacc actggctcgt ttccgtgccc aaatccaagg cgaagttttc tagagggttc    2160
```

-continued

```
ttgggctctt ggcacctgcg tgtcctgtgc ttaccaccgc ccaaggcccc cttggatctc      2220
ttggatagga gttggtgaat agaaggcagg cagcatcaca ctggggtcac tgacagactt      2280
gaagctgaca tttggcaggg catcgaaggg atgcatccat gaagtcacca gtctcaagcc      2340
catgtggtag gcggtgatgg aacaactgtc aaatcagttt tagcatgacc tttccttgtg      2400
gattttctta ttctcgttgt caagtttct  agggttgaat tttttcttt  tttctccatg      2460 gtgttaatga tattagagat gaaaaacgtt agcagttgat ttttgtccaa aagcaagtca      2520
tggctagagt atccatgcaa ggtgtcttgt tgcatggaag ggatagtttg gctcccttgg      2580
aggctatgta ggcttgtccc gggaaagaga actgtcctgc agctgaaatg gactgttctt      2640
tactgacctg ctcagcagtt cttctctca  tatattccca aaacaagtac atctgcgatc      2700
aactctagcc aaatttgccc ctgtgtgcta catgatggat gattattatt ttaaggtctg      2760
tttaggaagg gaaatggcta cttggccagc cattgcctgg catttggtag tatagtatga      2820
ttctcaccat tatttgtcat ggaggcagac atacaccaga aatgggggag aaacagtaca      2880
tatctttctg tctttagttt attgtgtgct ggtctaagca agctgagatc atttgcaatg      2940
gaaaacacgt aacttgttta aaagtttttc tggtagcttt agctttatgc taaaaaaaat      3000
aatgacattg ggtatctatt tctttctaag actacattag taggaaaata agtcttttca      3060
tgcttatgat ttagctgttt tgtggtaatt gcttttaaa  ggaagttatt aatatcataa      3120
gttattatta atattttgaa cacaggtgga tgtgaaggat tttcatttaa aaaccaagtg      3180
gttttgactt tttctgttga atgaacaact gtgccttgtg gaattttgc  agaagtgttt      3240 atgctttgtt agcatttcaa cttgcattat tataaagagg tattaatgcc tcagttatgt      3300
gtttgtcaat gtactggctg aggattctat ctcagctgtc ttttctaact gtgtaggttg      3360
agttttgaac acgtgcttgt ggacatcagg cctcctgcca gcagttcttg aagcttcttt      3420
ttcattcctg ctactctacc tgtatttctc agttgcagca ctgagtggtc aaaatacatt      3480
tctgggccac ctcagggaac ccatgcatct gcctggcatt taggcagcag agccctgac      3540 cgtcccccac agggctctgc ctcacgtcct catctcattt ggctgtgtaa agaaatggga      3600
aaagggaaaa ggagagagca attgaggcag ttgaccatat tcagttttat ttatttattt      3660
ttaatttgtt ttttttctcca agtccaccag tctctgaaat tagaacagta ggcggtatga      3720
gataatcagg cctaatcatg ttgtgattct cttttcttag tggagtggaa tgttctatcc      3780
ccacaagaag gattatatct tatagacttg tcttgttcag attctgtatt tacccatttt      3840
attgaaacat atactaagtt ccatgtattt ttgttacaaa tcttctgaaa aaaaacaaaa      3900
caatgtgaaa cattaaaatt aaaaggcatt aataatatcc acgtgtgcct tcttactgaa      3960
aaaaaaaaa                                                              3969
```

<210> SEQ ID NO 14
<211> LENGTH: 4096
<212> TYPE: DNA
<213> ORGANISM: Homo sapiens

<400> SEQUENCE: 14

```
agaccctcac gtgatgacaa cagctagcaa agttctgtag ctactgcctt agggcatagt        60
ctaatttctt cagtaaaaac acacttattc caaatttggt tccagaattg ccttaaattg       120
tttttgctct gttcttaggt tggggcggc  tatgagcagg cagaggatgt ggtgtcaccc       180
aattaggagc tctcagctta cgaggcaatt agcataggtt gccagggctg cacgaggagt       240
```

-continued

```
ggatttctgc tttgtcattc tgactctggc agttagcccg cccgctcggc gcagggcgtg     300
gcttctcgta gccattagga aacagcaacc ctttcacctc agttttcttc actccggcat     360
ttgcagcaga gcgaaaggtg gtcgagtcct gaaggagggc ctgatgtctt catcattctc     420
aaattcttgt aagctctgcg tcgggtgaaa ccagacaaag ccgcgagccc agggatggga     480
gcacgcgggg gacggcctgc cggcggggac gacagcattg cgcctgggtg cagcagtgtg     540
cgtctcgggg aagggaagat attttaaggc gtgtctgagc agacggggag gcttttccaa     600
acccaggcag cttcgtggcg tgtgcggttt cgacccggtc acacaaagct tcagcatgtc     660
atgtggctta tcaggagggc agacttcaaa agctactaaa aatgaacggc cctgaagatc     720
ttcccaagtc ctatgactat gaccttatca tcattggagg tggctcagga ggtctggcag     780
ctgctaagga ggcagcccaa tatggcaaga aggtgatggt cctggacttt gtcactccca     840
cccctcttgg aactagatgg ggtctcggag gaacatgtgt gaatgtgggt tgcatacccta    900 aaaaactgat gcatcaagca gctttgttag gacaagccct gcaagactct cgaaattatg     960
gatggaaagt cgaggagaca gttaagcatg attgggacag aatgatagaa gctgtacaga    1020
atcacattgg ctctttgaat tggggctacc gagtagctct gcgggagaaa aaagtcgtct    1080
atgagaatgc ttatgggcaa tttattggtc ctcacaggat taaggcaaca aataataaag    1140
gcaaagaaaa aatttattca gcagagagat ttctcattgc cactggtgaa agaccacgtt    1200
acttgggcat ccctggtgac aaagaatact gcatcagcag tgatgatctt ttctccttgc    1260
cttactgccc gggtaagacc ctggttgttg gagcatccta tgtcgctttg gagtgcgctg    1320
gatttcttgc tggtattggt ttagacgtca ctgttatggt taggtccatt cttcttagag    1380
gatttgacca ggacatggcc aacaaaattg gtgaacacat ggaagaacat ggcatcaagt    1440
ttataagaca gttcgtacca attaaagttg aacaaattga agcagggaca ccaggccgac    1500
tcagagtagt agctcagtcc accaatagtg aggaaatcat tgaaggagaa tataatacgg    1560
tgatgctggc aataggaaga gatgcttgca caagaaaaat tggcttagaa accgtagggg    1620
tgaagataaa tgaaaagact ggaaaaatac ctgtcacaga tgaagaacag accaatgtgc    1680
cttacatcta tgccattggc gatatattgg aggataaggt ggagctcacc ccagttgcaa    1740
tccaggcagg aagattgctg gctcagaggc tctatgcagg ttccactgtc aagtgtgact    1800
atgaaaatgt tccaaccact gtatttactc ctttggaata tggtgcttgt ggcctttctg    1860
aggagaaagc tgtggagaag tttgggggaag aaaatattga ggtttaccat agttactttt    1920
ggccattgga atggacgatt ccgtcaagag ataacaacaa atgttatgca aaaataatct    1980
gtaatactaa agacaatgaa cgtgttgtgg gctttcacgt actgggtcca aatgctggag    2040
aagttacaca aggctttgca gctgcgctca aatgtggact gaccaaaaag cagctggaca    2100
gcacaattgg aatccaccct gtctgtgcag aggtattcac aacattgtct gtgaccaagc    2160 gctctgggc aagcatcctc caggctggct gctgaggtta agcccagtg tggatgctgt      2220 tgccaagact gcaaaccact ggctcgtttc cgtgcccaaa tccaaggcga agttttctag    2280
agggttcttg ggctcttggc acctgcgtgt cctgtgctta ccaccgccca aggccccctt    2340
ggatctcttg gataggagtt ggtgaataga aggcaggcag catcacactg gggtcactga    2400
cagacttgaa gctgacattt ggcagggcat cgaagggatg catccatgaa gtcaccagtc    2460
tcaagcccat gtggtaggcg gtgatggaac aactgtcaaa tcagttttag catgaccttt    2520
ccttgtggat tttcttattc tcgttgtcaa gttttctagg gttgaatttt tttctttttt    2580
ctccatggtg ttaatgatat tagagatgaa aaacgttagc agttgatttt tgtccaaaag    2640
```

-continued

```
caagtcatgg ctagagtatc catgcaaggt gtcttgttgc atggaaggga tagtttggct      2700
cccttggagg ctatgtaggc ttgtcccggg aaagagaact gtcctgcagc tgaaatggac      2760
tgttctttac tgacctgctc agcagtttct tctctcatat attcccaaaa caagtacatc      2820
tgcgatcaac tctagccaaa tttgcccctg tgtgctacat gatggatgat tattatttta      2880
aggtctgttt aggaagggaa atggctactt ggccagccat tgcctggcat ttggtagtat      2940
agtatgattc tcaccattat ttgtcatgga ggcagacata caccagaaat gggggagaaa      3000
cagtacatat ctttctgtct ttagtttatt gtgtgctggt ctaagcaagc tgagatcatt      3060
tgcaatggaa aacacgtaac ttgtttaaaa gtttttctgg tagcttttagc tttatgctaa      3120 aaaaaataat gacattgggt atctatttct ttctaagact acattagtag gaaaataagt      3180
cttttcatgc ttatgattta gctgtttgt ggtaattgct ttttaaagga agttattaat      3240
atcataagtt attattaata ttttgaacac aggtggatgt gaaggatttt catttaaaaa      3300
ccaagtggtt ttgacttttt ctgttgaatg aacaactgtg ccttgtggaa tttttgcaga      3360
agtgtttatg ctttgttagc atttcaactt gcattattat aaagaggtat taatgcctca      3420
gttatgtgtt tgtcaatgta ctggctgagg attctatctc agctgtcttt tctaactgtg      3480
taggttgagt tttgaacacg tgcttgtgga catcaggcct cctgccagca gttcttgaag      3540 cttcttttc attcctgcta ctctacctgt atttctcagt tgcagcactg agtggtcaaa      3600
atacatttct gggccacctc agggaaccca tgcatctgcc tggcatttag gcagcagagc      3660
ccctgaccgt cccccacagg gctctgcctc acgtcctcat ctcatttggc tgtgtaaaga      3720
aatgggaaaa gggaaaagga gagagcaatt gaggcagttg accatattca gttttatta       3780 tttattttta atttgttttt ttctccaagt ccaccagtct ctgaaattag aacagtaggc      3840
ggtatgagat aatcaggcct aatcatgttg tgattctctt ttcttagtgg agtggaatgt      3900
tctatcccca caagaaggat tatatcttat agacttgtct tgttcagatt ctgtatttac      3960
ccattttatt gaaacatata ctaagttcca tgtattttg ttacaaatct tctgaaaaaa       4020
aacaaaacaa tgtgaaacat taaaattaaa aggcattaat aatatccacg tgtgccttct      4080
tactgaaaaa aaaaaa                                                       4096
```

```
<210> SEQ ID NO 15
<211> LENGTH: 3859
<212> TYPE: DNA
<213> ORGANISM: Homo sapiens

<400> SEQUENCE: 15
```

```
agaccctcac gtgatgacaa cagctagcaa agttctgtag ctactgcctt agggcatagt        60
ctaatttctt cagtaaaaac acacttattc caaatttggt tccagaattg ccttaaattg       120
tttttgctct gttcttaggt tgggggcggc tatgagcagg cagaggatgt ggtgtcaccc       180
aattaggagc tctcagctta cgaggcaatt agcataggtt gccagggctg cacgaggagt       240
ggatttctgc tttgtcattc tgactctggc agttagcccg cccgctcggc gcagggcgtg       300
gcttctcgta gccattagga aacagcaacc cttcacctc agttttcttc actccggcat        360
ttgcagcaga gcgaaaggtg gtcgagtcct gaaggaggg ctgatgtctt catcattctc        420
aaattcttgc ttatcaggag ggcagacttc aaaagctact aaaaatgaac ggccctgaag       480
atcttcccaa gtcctatgac tatgacctta tcatcattgg aggtggctca ggaggtctgg       540
cagctgctaa ggaggcagcc caatatggca agaaggtgat ggtcctggac tttgtcactc       600
```

-continued

```
ccacccctct tggaactaga tggggtctcg gaggaacatg tgtgaatgtg ggttgcatac    660
ctaaaaaact gatgcatcaa gcagctttgt taggacaagc cctgcaagac tctcgaaatt    720
atggatggaa agtcgaggag acagttaagc atgattggga cagaatgata gaagctgtac    780
agaatcacat tggctctttg aattgggggct accgagtagc tctgcgggag aaaaaagtcg    840
tctatgagaa tgcttatggg caatttattg gtcctcacag gattaaggca acaaataata    900
aaggcaaaga aaaaatttat tcagcagaga gatttctcat tgccactggt gaaagaccac    960
gttacttggg catccctggt gacaaagaat actgcatcag cagtgatgat cttttctcct   1020
tgccttactg cccgggtaag accctggttg ttggagcatc ctatgtcgct ttggagtgcg   1080
ctggatttct tgctggtatt ggtttagacg tcactgttat ggttaggtcc attcttctta   1140
gaggatttga ccaggacatg gccaacaaaa ttggtgaaca catggaagaa catggcatca   1200
agtttataag acagttcgta ccaattaaag ttgaacaaat tgaagcaggg acaccaggcc   1260
gactcagagt agtagctcag tccaccaata gtgaggaaat cattgaagga gaatataata   1320
cggtgatgct ggcaatagga agagatgctt gcacaagaaa aattggctta gaaaccgtag   1380
gggtgaagat aaatgaaaag actggaaaaa tacctgtcac agatgaagaa cagaccaatg   1440
tgccttacat ctatgccatt ggcgatatat tggaggataa ggtggagctc accccagttg   1500
caatccaggc aggaagattg ctggctcaga ggctctatgc aggttccact gtcaagtgtg   1560
actatgaaaa tgttccaacc actgtattta ctcctttgga atatggtgct tgtggccttt   1620
ctgaggagaa agctgtggag aagtttgggg aagaaaatat tgaggtttac catagttact   1680
tttggccatt ggaatggacg attccgtcaa gagataacaa caaatgttat gcaaaaataa   1740
tctgtaatac taaagacaat gaacgtgttg tgggctttca cgtactgggt ccaaatgctg   1800
gagaagttac acaaggcttt gcagctgcgc tcaaatgtgg actgaccaaa aagcagctgg   1860
acagcacaat tggaatccac cctgtctgtg cagaggtatt cacaacattg tctgtgacca   1920
agcgctctgg ggcaagcatc ctccaggctg gctgctgagg ttaagcccca gtgtggatgc   1980
tgttgccaag actgcaaacc actggctcgt ttccgtgccc aaatccaagg cgaagttttc   2040
tagagggttc ttgggctctt ggcacctgcg tgtcctgtgc ttaccaccgc ccaaggcccc   2100
cttggatctc ttggatagga gttggtgaat agaaggcagg cagcatcaca ctggggtcac   2160
tgacagactt gaagctgaca tttggcaggg catcgaaggg atgcatccat gaagtcacca   2220
gtctcaagcc catgtggtag gcggtgatgg aacaactgtc aaatcagttt tagcatgacc   2280
tttccttgtg gattttctta ttctcgttgt caagttttct agggttgaat ttttttcttt   2340
tttctccatg gtgttaatga tattagagat gaaaaacgtt agcagttgat ttttgtccaa   2400
aagcaagtca tggctagagt atccatgcaa ggtgtcttgt tgcatggaag ggatagtttg   2460
gctcccttgg aggctatgta ggcttgtccc gggaaagaga actgtcctgc agctgaaatg   2520
gactgttctt tactgacctg ctcagcagtt tcttctctca tatattccca aaacaagtac   2580
atctgcgatc aactctagcc aaatttgccc ctgtgtgcta catgatggat gattattatt   2640
ttaaggtctg tttaggaagg gaaatggcta cttggccagc cattgcctgg catttggtag   2700
tatagtatga ttctcaccat tatttgtcat ggaggcagac atacaccaga aatggggggag   2760 aaacagtaca tatctttctg tctttagttt attgtgtgct ggtctaagca agctgagatc   2820
atttgcaatg gaaaacacgt aacttgttta aaagttttttc tggtagcttt agctttatgc   2880
taaaaaaaat aatgacattg ggtatctatt tctttctaag actacattag taggaaaata   2940 agtctttttca tgcttatgat ttagctgttt tgtggtaatt gctttttaaa ggaagttatt   3000
```

-continued

```
aatatcataa gttattatta atattttgaa cacaggtgga tgtgaaggat tttcatttaa      3060
aaaccaagtg gttttgactt tttctgttga atgaacaact gtgccttgtg gaattttttgc    3120 agaagtgttt atgctttgtt agcatttcaa cttgcattat tataaagagg tattaatgcc     3180
tcagttatgt gtttgtcaat gtactggctg aggattctat ctcagctgtc ttttctaact    3240
gtgtaggttg agttttgaac acgtgcttgt ggacatcagg cctcctgcca gcagttcttg    3300
aagcttcttt ttcattcctg ctactctacc tgtatttctc agttgcagca ctgagtggtc    3360
aaaatacatt tctgggccac ctcagggaac ccatgcatct gcctggcatt taggcagcag    3420
agcccctgac cgtcccccac agggctctgc ctcacgtcct catctcattt ggctgtgtaa     3480
agaaatggga aaagggaaaa ggagagagca attgaggcag ttgaccatat tcagttttat    3540
ttatttattt ttaatttgtt ttttctccca agtccaccag tctctgaaat tagaacagta     3600
ggcggtatga gataatcagg cctaatcatg ttgtgattct ctttttcttag tggagtggaa    3660 tgttctatcc ccacaagaag gattatatct tatagacttg tcttgttcag attctgtatt     3720
tacccatttt attgaaacat atactaagtt ccatgtattt ttgttacaaa tcttctgaaa    3780
aaaaacaaaa caatgtgaaa cattaaaatt aaaaggcatt aataatatcc acgtgtgcct    3840
tcttactgaa aaaaaaaaa                                                  3859
```

```
<210> SEQ ID NO 16
<211> LENGTH: 4206
<212> TYPE: DNA
<213> ORGANISM: Homo sapiens

<400> SEQUENCE: 16
```

```
agaccctcac gtgatgacaa cagctagcaa agttctgtag ctactgcctt agggcatagt       60
ctaatttctt cagtaaaaac acacttattc caaatttggt tccagaattg ccttaaattg      120 ttttttgctct gttcttaggt tgggggcggc tatgagcagg cagaggatgt ggtgtcaccc     180
aattaggagc tctcagctta cgaggcaatt agcataggtt gccagggctg cacgaggagt      240
ggatttctgc tttgtcattc tgactctggc agttagcccg cccgctcggc gcagggcgtg      300
gcttctcgta gccattagga aacagcaacc ctttcacctc agttttcttc actccggcat      360
ttgcagcaga gcgaaaggtg gtcgagtcct gaaggagggc ctgatgtctt catcattctc     420
aaattcttgt aagctctgcg tcgggtgaaa ccagacaaag ccgcgagccc agggatggga     480
gcacgcgggg gacggcctgc cggcggggac gacagcattg cgcctgggtg cagcagtgtg     540
cgtctcgggg aagggaagat attttaaggc gtgtctgagc agacggggag gcttttccaa     600
acccaggcag cttcgtggcg tgtgcggttt cgacccggtc acacaaagct tcagcatgtc     660
atgtgaggac ggtcgggccc tggaaggaac gctctcggaa ttggccgcgg aaaccgatct    720
gcccgttgtg tttgtgaaac agagaaagat aggcggccat ggtccaacct tgaaggctta    780
tcaggagggc agacttcaaa agctactaaa aatgaacggc cctgaagatc ttcccaagtc     840
ctatgactat gaccttatca tcattggagg tggctcagga ggtctggcag ctgctaagga     900
ggcagcccaa tatggcaaga aggtgatggt cctggacttt gtcactccca cccctcttgg     960
aactagatgg ggtctcggag aacatgtgt gaatgtgggt tgcataccta aaaaactgat      1020
gcatcaagca gctttgttag acaagcccct gcaagactct cgaaattatg gatggaaagt     1080
cgaggagaca gttaagcatg attgggacag aatgatagaa gctgtacaga atcacattgg     1140
ctctttgaat tggggctacc gagtagctct gcgggagaaa aaagtcgtct atgagaatgc     1200
```

-continued

```
ttatgggcaa tttattggtc ctcacaggat taaggcaaca aataataaag gcaaagaaaa   1260
aatttattca gcagagagat ttctcattgc cactggtgaa agaccacgtt acttgggcat   1320
ccctggtgac aaagaatact gcatcagcag tgatgatctt ttctccttgc cttactgccc   1380
gggtaagacc ctggttgttg gagcatccta tgtcgctttg gagtgcgctg gatttcttgc   1440
tggtattggt ttagacgtca ctgttatggt taggtccatt cttcttagag gatttgacca   1500
ggacatggcc aacaaaattg gtgaacacat ggaagaacat ggcatcaagt ttataagaca   1560
gttcgtacca attaaagttg aacaaattga agcagggaca ccaggccgac tcagagtagt   1620
agctcagtcc accaatagtg aggaaatcat tgaaggagaa tataatacgg tgatgctggc   1680
aataggaaga gatgcttgca caagaaaaat tggcttagaa accgtagggg tgaagataaa   1740
tgaaaagact ggaaaaatac ctgtcacaga tgaagaacag accaatgtgc cttacatcta   1800
tgccattggc gatatattgg aggataaggt ggagctcacc ccagttgcaa tccaggcagg   1860
aagattgctg gctcagaggc tctatgcagg ttccactgtc aagtgtgact atgaaaatgt   1920
tccaaccact gtatttactc ctttggaata tggtgcttgt ggcctttctg aggagaaagc   1980
tgtggagaag tttggggaag aaaatattga ggtttaccat agttactttt ggccattgga   2040
atggacgatt ccgtcaagag ataacaacaa atgttatgca aaaataatct gtaatactaa   2100
agacaatgaa cgtgttgtgg gctttcacgt actgggtcca aatgctggag aagttacaca   2160
aggctttgca gctgcgctca aatgtggact gaccaaaaag cagctggaca gcacaattgg   2220
aatccaccct gtctgtgcag aggtattcac aacattgtct gtgaccaagc gctctgggc   2280 aagcatcctc caggctggct gctgaggtta agccccagtg tggatgctgt tgccaagact   2340
gcaaaccact ggctcgtttc cgtgcccaaa tccaaggcga agttttctag agggttcttg   2400
ggctcttggc acctgcgtgt cctgtgctta ccaccgccca aggcccccctt ggatctcttg   2460 gataggagtt ggtgaataga aggcaggcag catcacactg gggtcactga cagacttgaa   2520
gctgacattt ggcagggcat cgaagggatg catccatgaa gtcaccagtc tcaagcccat   2580
gtggtaggcg gtgatggaac aactgtcaaa tcagttttag catgaccttt ccttgtggat   2640
tttcttattc tcgttgtcaa gttttctagg gttgaatttt tttctttttt ctccatggtg   2700
ttaatgatat tagagatgaa aaacgttagc agttgatttt tgtccaaaag caagtcatgg   2760
ctagagtatc catgcaaggt gtcttgttgc atggaaggga tagtttggct cccttggagg   2820
ctatgtaggc ttgtcccggg aaagagaact gtcctgcagc tgaaatggac tgttctttac   2880
tgacctgctc agcagtttct tctctcatat attcccaaaa caagtacatc tgcgatcaac   2940
tctagccaaa tttgcccctg tgtgctacat gatggatgat tattatttta aggtctgttt   3000
aggaagggaa atggctactt ggccagccat tgcctggcat ttggtagtat agtatgattc   3060
tcaccattat ttgtcatgga ggcagacata caccagaaat gggggagaaa cagtacatat   3120
ctttctgtct ttagtttatt gtgtgctggt ctaagcaagc tgagatcatt tgcaatggaa   3180
aacacgtaac ttgtttaaaa gttttttctgg tagctttagc tttatgctaa aaaaaataat   3240
gacattgggt atctatttct ttctaagact acattagtag gaaaataagt cttttcatgc   3300
ttatgattta gctgttttgt ggtaattgct tttttaaagga agttattaat atcataagtt   3360
attattaata ttttgaacac aggtggatgt gaaggatttt catttaaaaa ccaagtggtt   3420
ttgacttttt ctgttgaatg aacaactgtg ccttgtggaa tttttgcaga agtgtttatg   3480
ctttgttagc atttcaactt gcattattat aaagaggtat taatgcctca gttatgtgtt   3540
tgtcaatgta ctggctgagg attctatctc agctgtcttt tctaactgtg taggttgagt   3600
```

```
tttgaacacg tgcttgtgga catcaggcct cctgccagca gttcttgaag cttctttttc    3660
attcctgcta ctctacctgt atttctcagt tgcagcactg agtggtcaaa atacatttct    3720
gggccacctc agggaaccca tgcatctgcc tggcatttag gcagcagagc ccctgaccgt    3780
cccccacagg gctctgcctc acgtcctcat ctcatttggc tgtgtaaaga aatgggaaaa    3840
gggaaaagga gagagcaatt gaggcagttg accatattca gttttattta tttattttta    3900
atttgttttt ttctccaagt ccaccagtct ctgaaattag aacagtaggc ggtatgagat    3960
aatcaggcct aatcatgttg tgattctctt ttcttagtgg agtggaatgt tctatcccca    4020
caagaaggat tatatcttat agacttgtct tgttcagatt ctgtatttac ccattttatt    4080
gaaacatata ctaagttcca tgtatttttg ttacaaatct tctgaaaaaa aacaaaacaa    4140
tgtgaaacat taaaattaaa aggcattaat aatatccacg tgtgccttct tactgaaaaa    4200
aaaaaa                                                               4206

<210> SEQ ID NO 17
<211> LENGTH: 4291
<212> TYPE: DNA
<213> ORGANISM: Homo sapiens

<400> SEQUENCE: 17
agaccctcac gtgatgacaa cagctagcaa agttctgtag ctactgcctt agggcatagt      60
ctaatttctt cagtaaaaac acacttattc caaatttggt tccagaattg ccttaaattg     120
tttttgctct gttcttaggt tgggggcggc tatgagcagg cagaggatgt ggtgtcaccc     180
aattaggagc tctcagctta cgaggcaatt agcataggtt gccagggctg cacgaggagt     240
ggatttctgc tttgtcattc tgactctggc agttagcccg cccgctcggc gcagggcgtg     300
gcttctcgta gccattagga aacagcaacc cttttcacctc agtttttcttc actccggcat     360 ttgcagcaga gcgaaaggtg gtcgagtcct gaaggagggc ctgatgtctt catcattctc     420
aaattcttgt aagctctgcg tcgggtgaaa ccagacaaag ccgcgagccc agggatggga     480
gcacgcgggg gacggcctgc cggcggggac gacagcattg cgcctgggtg cagcagtgtg     540
cgtctcgggg aagggaagat attttaaggc gtgtctgagc agacgggggag gcttttccaa     600 acccaggcag cttcgtggcg tgtgcggttt cgacccggtc acacaaagct tcagcatgtc     660
atgtggtagg tgaggccggc gcctgtaggc tggcggtttc cttcctcttg gtctttgtag     720
agacagtttg cagaacagcg gagaaaatgg aggacggtcg ggccctggaa ggaacgctct     780
cggaattggc cgcggaaacc gatctgcccg ttgtgtttgt gaaacagaga aagataggcg     840
gccatggtcc aaccttgaag gcttatcagg agggcagact tcaaaagcta ctaaaaatga     900
acggccctga agatcttccc aagtcctatg actatgacct tatcatcatt ggaggtggct     960
caggaggtct ggcagctgct aaggaggcag cccaatatgg caagaaggtg atggtcctgg    1020
actttgtcac tcccacccct cttggaacta gatggggtct cggaggaaca tgtgtgaatg    1080
tgggttgcat acctaaaaaa ctgatgcatc aagcagcttt gttaggacaa gccctgcaag    1140
actctcgaaa ttatggatgg aaagtcgagg agacagttaa gcatgattgg gacagaatga    1200
tagaagctgt acagaatcac attggctctt tgaattgggg ctaccgagta gctctgcggg    1260
agaaaaaagt cgtctatgag aatgcttatg ggcaatttat tggtcctcac aggattaagg    1320
caacaaataa taaaggcaaa gaaaaaattt attcagcaga gagatttctc attgccactg    1380
gtgaaagacc acgttacttg ggcatccctg gtgacaaaga atactgcatc agcagtgatg    1440
```

-continued

```
atctttctc  cttgccttac  tgcccgggta  agaccctggt  tgttggagca  tcctatgtcg   1500
ctttggagtg  cgctggattt  cttgctggta  ttggtttaga  cgtcactgtt  atggttaggt   1560
ccattcttct  tagaggattt  gaccaggaca  tggccaacaa  aattggtgaa  cacatggaag   1620
aacatggcat  caagtttata  agacagttcg  taccaattaa  agttgaacaa  attgaagcag   1680
ggacaccagg  ccgactcaga  gtagtagctc  agtccaccaa  tagtgaggaa  atcattgaag   1740
gagaatataa  tacggtgatg  ctggcaatag  gaagagatgc  ttgcacaaga  aaaattggct   1800
tagaaaccgt  aggggtgaag  ataaatgaaa  agactggaaa  aatacctgtc  acagatgaag   1860
aacagaccaa  tgtgccttac  atctatgcca  ttggcgatat  attggaggat  aaggtggagc   1920 tcacccccagt  tgcaatccag  gcaggaagat  tgctggctca  gaggctctat  gcaggttcca   1980
ctgtcaagtg  tgactatgaa  aatgttccaa  ccactgtatt  tactcctttg  gaatatggtg   2040
cttgtggcct  ttctgaggag  aaagctgtgg  agaagtttgg  ggaagaaaat  attgaggttt   2100
accatagtta  cttttggcca  ttggaatgga  cgattccgtc  aagagataac  aacaaatgtt   2160
atgcaaaaat  aatctgtaat  actaaagaca  atgaacgtgt  tgtgggcttt  cacgtactgg   2220
gtccaaatgc  tggagaagtt  acacaaggct  ttgcagctgc  gctcaaatgt  ggactgacca   2280
aaaagcagct  ggacagcaca  attggaatcc  accctgtctg  tgcagaggta  ttcacaacat   2340
tgtctgtgac  caagcgctct  ggggcaagca  tcctccaggc  tggctgctga  ggttaagccc   2400
cagtgtggat  gctgttgcca  agactgcaaa  ccactggctc  gtttccgtgc  ccaaatccaa   2460
ggcgaagttt  tctagagggt  tcttgggctc  ttggcacctg  cgtgtcctgt  gcttaccacc   2520
gcccaaggcc  cccttggatc  tcttggatag  gagttggtga  atagaaggca  ggcagcatca   2580
cactggggtc  actgacagac  ttgaagctga  catttggcag  ggcatcgaag  ggatgcatcc   2640
atgaagtcac  cagtctcaag  cccatgtggt  aggcggtgat  ggaacaactg  tcaaatcagt   2700
tttagcatga  cctttccttg  tggatttttct  tattctcgtt  gtcaagtttt  ctagggttga   2760 attttttttct  tttttctcca  tggtgttaat  gatattagag  atgaaaaacg  ttagcagttg   2820
atttttgtcc  aaaagcaagt  catggctaga  gtatccatgc  aaggtgtctt  gttgcatgga   2880
agggatagtt  tggctccctt  ggaggctatg  taggcttgtc  ccgggaaaga  gaactgtcct   2940
gcagctgaaa  tggactgttc  tttactgacc  tgctcagcag  tttcttctct  catatattcc   3000
caaaacaagt  acatctgcga  tcaactctag  ccaaatttgc  ccctgtgtgc  tacatgatgg   3060
atgattatta  ttttaaggtc  tgtttaggaa  gggaaatggc  tacttggcca  gccattgcct   3120
ggcatttggt  agtatagtat  gattctcacc  attatttgtc  atggaggcag  acatacacca   3180
gaaatggggg  agaaacagta  catatctttc  tgtctttagt  ttattgtgtg  ctggtctaag   3240
caagctgaga  tcatttgcaa  tggaaaacac  gtaacttgtt  taaaagtttt  tctggtagct   3300
ttagctttat  gctaaaaaaa  ataatgacat  tgggtatcta  tttctttcta  agactacatt   3360
agtaggaaaa  taagtctttt  catgcttatg  atttagctgt  tttgtggtaa  ttgctttttta   3420 aaggaagtta  ttaatatcat  aagttattat  taatattttg  aacacaggtg  gatgtgaagg   3480
attttcattt  aaaaaccaag  tggttttgac  tttttctgtt  gaatgaacaa  ctgtgccttg   3540 tggaatttttt  gcagaagtgt  ttatgctttg  ttagcatttc  aacttgcatt  attataaaga   3600
ggtattaatg  cctcagttat  gtgtttgtca  atgtactggc  tgaggattct  atctcagctg   3660
tcttttctaa  ctgtgtaggt  tgagttttga  acacgtgctt  gtggacatca  ggcctcctgc   3720
cagcagttct  tgaagcttct  tttttcattcc  tgctactcta  cctgtatttc  tcagttgcag   3780
cactgagtgg  tcaaaataca  tttctgggcc  acctcaggga  acccatgcat  ctgcctggca   3840
```

```
tttaggcagc agagcccctg accgtccccc acagggctct gcctcacgtc ctcatctcat    3900
ttggctgtgt aaagaaatgg gaaaagggaa aaggagagag caattgaggc agttgaccat    3960
attcagtttt atttatttat ttttaatttg tttttttctc caagtccacc agtctctgaa    4020
attagaacag taggcggtat gagataatca ggcctaatca tgttgtgatt ctcttttctt    4080
agtggagtgg aatgttctat ccccacaaga aggattatat cttatagact tgtcttgttc    4140
agattctgta tttacccatt ttattgaaac atatactaag ttccatgtat ttttgttaca    4200
aatcttctga aaaaaaacaa aacaatgtga aacattaaaa ttaaaaggca ttaataatat    4260
ccacgtgtgc cttcttactg aaaaaaaaaa a                                   4291

<210> SEQ ID NO 18
<211> LENGTH: 3846
<212> TYPE: DNA
<213> ORGANISM: Homo sapiens

<400> SEQUENCE: 18
agaccctcac gtgatgacaa cagctagcaa agttctgtag ctactgcctt agggcatagt      60
ctaatttctt cagtaaaaac acacttattc caaatttggt tccagaattg ccttaaattg     120
tttttgctct gttcttaggt tgggggcggc tatgagcagg cagaggatgt ggtgtcaccc     180
aattaggagc tctcagctta cgaggcaatt agcataggtt gccagggctg cacgaggagt     240
ggatttctgc tttgtcattc tgactctggc agttagcccg cccgctcggc gcagggcgtg     300
gcttctcgta gccattagga aacagcaacc ctttcacctc agttttcttc actccggcat     360
ttgcagcaga gcgaaaggtg gtcgagtcct gaaggagggc ctgatgtctt catcattctc     420
aaattcttag gacggtcggg ccctggaagg aacgctctcg gaattggccg cggaaaccga     480
tctgcccgtt gtgtttgtga aacagagaaa gataggcggc catggtccaa ccttgaagga     540
ggcagcccaa tatggcaaga aggtgatggt cctggacttt gtcactccca cccctcttgg     600
aactagatgg ggtctcggag gaacatgtgt gaatgtgggt tgcatcaccta aaaaactgat     660 gcatcaagca gctttgttag gacaagccct gcaagactct cgaaattatg gatggaaagt     720
cgaggagaca gttaagcatg attgggacag aatgatagaa gctgtacaga atcacattgg     780
ctctttgaat tggggctacc gagtagctct gcgggagaaa aaagtcgtct atgagaatgc     840
ttatgggcaa tttattggtc ctcacaggat taaggcaaca aataataaag gcaaagaaaa     900
aatttattca gcagagagat ttctcattgc cactggtgaa agaccacgtt acttgggcat     960
ccctggtgac aaagaatact gcatcagcag tgatgatctt ttctccttgc cttactgccc    1020
gggtaagacc ctggttgttg gagcatccta tgtcgctttg gagtgcgctg gatttcttgc    1080
tggtattggt ttagacgtca ctgttatggt taggtccatt cttcttagag gatttgacca    1140
ggacatggcc aacaaaattg gtgaacacat ggaagaacat ggcatcaagt ttataagaca    1200
gttcgtacca attaaagttg aacaaattga agcagggaca ccaggccgac tcagagtagt    1260
agctcagtcc accaatagtg aggaaatcat tgaaggagaa tataatacgg tgatgctggc    1320
aataggaaga gatgcttgca caagaaaaat tggcttagaa accgtagggg tgaagataaa    1380
tgaaaagact ggaaaaatac ctgtcacaga tgaagaacag accaatgtgc cttacatcta    1440
tgccattggc gatatattgg aggataaggt ggagctcacc ccagttgcaa tccaggcagg    1500
aagattgctg gctcagaggc tctatgcagg ttccactgtc aagtgtgact atgaaaatgt    1560
tccaaccact gtatttactc ctttggaata tggtgcttgt ggcctttctg aggagaaagc    1620
```

-continued

```
tgtggagaag tttggggaag aaaatattga ggtttaccat agttactttt ggccattgga      1680
atggacgatt ccgtcaagag ataacaacaa atgttatgca aaaataatct gtaatactaa      1740
agacaatgaa cgtgttgtgg gctttcacgt actgggtcca aatgctggag aagttacaca      1800
aggctttgca gctgcgctca aatgtggact gaccaaaaag cagctggaca gcacaattgg      1860
aatccaccct gtctgtgcag aggtattcac aacattgtct gtgaccaagc gctctggggc      1920
aagcatcctc caggctggct gctgaggtta agccccagtg tggatgctgt tgccaagact      1980
gcaaaccact ggctcgtttc cgtgcccaaa tccaaggcga agttttctag agggttcttg      2040
ggctcttggc acctgcgtgt cctgtgctta ccaccgccca aggcccccctt ggatctcttg      2100 gataggagtt ggtgaataga aggcaggcag catcacactg gggtcactga cagacttgaa      2160
gctgacattt ggcagggcat cgaagggatg catccatgaa gtcaccagtc tcaagcccat      2220
gtggtaggcg gtgatggaac aactgtcaaa tcagttttag catgaccttt ccttgtggat      2280
tttcttattc tcgttgtcaa gttttctagg gttgaatttt tttcttttttt ctccatggtg      2340 ttaatgatat tagagatgaa aaacgttagc agttgatttt tgtccaaaag caagtcatgg      2400
ctagagtatc catgcaaggt gtcttgttgc atggaaggga tagtttggct cccttggagg      2460
ctatgtaggc ttgtcccggg aaagagaact gtcctgcagc tgaaatggac tgttctttac      2520
tgacctgctc agcagtttct tctctcatat attcccaaaa caagtacatc tgcgatcaac      2580
tctagccaaa tttgcccctg tgtgctacac gatggatgat tattatttta aggtctgttt      2640
aggaagggaa atggctactt ggccagccat tgcctggcat ttggtagtat agtatgattc      2700
tcaccattat ttgtcatgga ggcagacata caccagaaat gggggagaaa cagtacatat      2760
ctttctgtct ttagtttatt gtgtgctggt ctaagcaagc tgagatcatt tgcaatggaa      2820
aacacgtaac ttgtttaaaa gttttttctgg tagctttagc tttatgctaa aaaaaataat      2880
gacattgggt atctatttct ttctaagact acattagtag gaaaataagt cttttcatgc      2940
ttatgattta gctgttttgt ggtaattgct tttttaaagga agttattaat atcataagtt      3000
attattaata ttttgaacac aggtggatgt gaaggatttt catttaaaaa ccaagtggtt      3060 ttgactttt ctgttgaatg aacaactgtg ccttgtggaa tttttgcaga agtgtttatg      3120
ctttgttagc atttcaactt gcattattat aaagaggtat taatgcctca gttatgtgtt      3180
tgtcaatgta ctggctgagg attctatctc agctgtcttt tctaactgtg taggttgagt      3240
tttgaacacg tgcttgtgga catcaggcct cctgccagca gttcttgaag cttctttttc      3300
attcctgcta ctctacctgt atttctcagt tgcagcactg agtggtcaaa atacatttct      3360
gggccacctc agggaaccca tgcatctgcc tggcatttag gcagcagagc ccctgaccgt      3420
cccccacagg gctctgcctc acgtcctcat ctcatttggc tgtgtaaaga aatgggaaaa      3480
gggaaaagga gagagcaatt gaggcagttg accatattca gttttattta tttattttta      3540
atttgttttt ttctccaagt ccaccagtct ctgaaattag aacagtaggc ggtatgagat      3600
aatcaggcct aatcatgttg tgattctctt ttcttagtgg agtggaatgt tctatcccca      3660
caagaaggat tatatcttat agacttgtct tgttcagatt ctgtatttac ccattttatt      3720
gaaacatata ctaagttcca tgtatttttg ttacaaatct tctgaaaaaa aacaaaacaa      3780
tgtgaaacat taaaattaaa aggcattaat aatatccacg tgtgccttct tactgaaaaa      3840
aaaaaa                                                                  3846
```

<210> SEQ ID NO 19
<211> LENGTH: 3860

<212> TYPE: DNA
<213> ORGANISM: Homo sapiens

<400> SEQUENCE: 19
agttcccaca gggccttgtg cgacatgggc tgcgccgagg gcaaggcagt ggcggcggcc      60
gccccaacgg agctgcagac gaaaggcaag aacggcgatg gccgccgtag gtcagctaaa     120
gatcatcacc ctggtaaaac tttgccagag aacccagcag gattcaccag cacggccact     180
gcagactcca gagccctgct tcaggcctat atagatggtc actctgtggt catcttcagt     240
aggtccacat gcacacgctg tactgaggta aagaagttat ttaaatctct gtgtgttcct     300
tattttgtgc ttgaacttga tcaaacagag gacggtcggg ccctggaagg aacgctctcg     360
gaattggccg cggaaaccga tctgcccgtt gtgtttgtga aacagagaaa gataggcggc     420
catggtccaa ccttgaaggc ttatcaggag ggcagacttc aaaagctact aaaaatgaac     480
ggccctgaag atcttcccaa gtcctatgac tatgacctta tcatcattgg aggtggctca     540
ggaggtctgg cagctgctaa ggaggcagcc caatatggca agaaggtgat ggtcctggac     600
tttgtcactc ccacccctct tggaactaga tggggtctcg gaggaacatg tgtgaatgtg     660
ggttgcatac ctaaaaaact gatgcatcaa gcagctttgt taggacaagc cctgcaagac     720
tctcgaaatt atggatggaa agtcgaggag acagttaagc atgattggga cagaatgata     780
gaagctgtac agaatcacat tggctctttg aattggggct accgagtagc tctgcgggag     840
aaaaaagtcg tctatgagaa tgcttatggg caatttattg gtcctcacag gattaaggca     900
acaaataata aaggcaaaga aaaaatttat tcagcagaga gatttctcat tgccactggt     960
gaaagaccac gttacttggg catccctggt gacaaagaat actgcatcag cagtgatgat    1020
cttttctcct tgccttactg cccgggtaag accctggttg ttggagcatc ctatgtcgct    1080
ttggagtgcg ctggatttct tgctggtatt ggtttagacg tcactgttat ggttaggtcc    1140
attcttctta gaggatttga ccaggacatg gccaacaaaa ttggtgaaca catggaagaa    1200
catggcatca agtttataag acagttcgta ccaattaaag ttgaacaaat tgaagcaggg    1260
acaccaggcc gactcagagt agtagctcag tccaccaata gtgaggaaat cattgaagga    1320
gaatataata cggtgatgct ggcaatagga agagatgctt gcacaagaaa aattggctta    1380
gaaaccgtag gggtgaagat aaatgaaaag actggaaaaa tacctgtcac agatgaagaa    1440
cagaccaatg tgccttacat ctatgccatt ggcgatatat tggaggataa ggtggagctc    1500
accccagttg caatccaggc aggaagattg ctggctcaga ggctctatgc aggttccact    1560
gtcaagtgtg actatgaaaa tgttccaacc actgtattta ctcctttgga atatggtgct    1620
tgtggccttt ctgaggagaa agctgtggag aagtttgggg aagaaaatat tgaggtttac    1680
catagttact tttggccatt ggaatggacg attccgtcaa gagataacaa caaatgttat    1740
gcaaaaataa tctgtaatac taaagacaat gaacgtgttg tgggctttca cgtactgggt    1800
ccaaatgctg gagaagttac acaaggcttt gcagctgcgc tcaaatgtgg actgaccaaa    1860
aagcagctgg acagcacaat tggaatccac cctgtctgtg cagaggtatt cacaacattg    1920
tctgtgacca agcgctctgg ggcaagcatc ctccaggctg gctgctgagg ttaagcccca    1980
gtgtggatgc tgttgccaag actgcaaacc actggctcgt ttccgtgccc aaatccaagg    2040
cgaagttttc tagagggttc ttgggctctt ggcacctgcg tgtcctgtgc ttaccaccgc    2100
ccaaggcccc cttggatctc ttggatagga gttggtgaat agaaggcagg cagcatcaca    2160
ctggggtcac tgacagactt gaagctgaca tttggcaggg catcgaaggg atgcatccat    2220

-continued

```
gaagtcacca gtctcaagcc catgtggtag gcggtgatgg aacaactgtc aaatcagttt    2280
tagcatgacc tttccttgtg gattttctta ttctcgttgt caagttttct agggttgaat    2340
tttttctttt tttctccatg gtgttaatga tattagagat gaaaaacgtt agcagttgat    2400
ttttgtccaa aagcaagtca tggctagagt atccatgcaa ggtgtcttgt tgcatggaag    2460
ggatagtttg gctcccttgg aggctatgta ggcttgtccc gggaaagaga actgtcctgc    2520
agctgaaatg gactgttctt tactgacctg ctcagcagtt tcttctctca tatattccca    2580
aaacaagtac atctgcgatc aactctagcc aaatttgccc ctgtgtgcta catgatggat    2640
gattattatt ttaaggtctg tttaggaagg gaaatggcta cttggccagc cattgcctgg    2700
catttggtag tatagtatga ttctcaccat tatttgtcat ggaggcagac atacaccaga    2760 aatggggggag aaacagtaca tatctttctg tctttagttt attgtgtgct ggtctaagca    2820
agctgagatc atttgcaatg gaaaacacgt aacttgttta aaagtttttc tggtagcttt    2880
agctttatgc taaaaaaaat aatgacattg ggtatctatt tctttctaag actacattag    2940
taggaaaata agtctttttca tgcttatgat ttagctgttt tgtggtaatt gcttttttaaa    3000 ggaagttatt aatatcataa gttattatta atattttgaa cacaggtgga tgtgaaggat    3060
tttcatttaa aaaccaagtg gttttgactt tttctgttga atgaacaact gtgccttgtg    3120
gaatttttgc agaagtgttt atgctttgtt agcatttcaa cttgcattat tataaagagg    3180
tattaatgcc tcagttatgt gtttgtcaat gtactggctg aggattctat ctcagctgtc    3240
ttttctaact gtgtaggttg agttttgaac acgtgcttgt ggacatcagg cctcctgcca    3300
gcagttcttg aagcttcttt ttcattcctg ctactctacc tgtatttctc agttgcagca    3360
ctgagtggtc aaaatacatt tctgggccac ctcagggaac ccatgcatct gcctggcatt    3420
taggcagcag agcccctgac cgtcccccac agggctctgc ctcacgtcct catctcattt    3480
ggctgtgtaa agaaatggga aaagggaaaa ggagagagca attgaggcag ttgaccatat    3540 tcagtttttat ttatttattt ttaatttgtt tttttctcca agtccaccag tctctgaaat    3600
tagaacagta ggcggtatga gataatcagg cctaatcatg ttgtgattct cttttcttag    3660
tggagtggaa tgttctatcc ccacaagaag gattatatct tatagacttg tcttgttcag    3720
attctgtatt tacccatttt attgaaacat atactaagtt ccatgtattt ttgttacaaa    3780
tcttctgaaa aaaaacaaaa caatgtgaaa cattaaaatt aaaaggcatt aataatatcc    3840
acgtgtgcct tcttactgaa                                                3860
```

```
<210> SEQ ID NO 20
<211> LENGTH: 3417
<212> TYPE: DNA
<213> ORGANISM: Mus musculus

<400> SEQUENCE: 20
```

```
agtttgcttc cgtcaggcct cgcgtccacg cgggaggtgc gggacgccga caccgcgggg     60
cgagaagagc tggtggtttc accttccttg ttcatagggc ggcggggcct tgcagcggcg    120
cgggcgagcg gaaaggccgc gggaggcggc gagccagcgg aaggtgcgac cggcggaggg    180
cggccatggt ccagccctga agccgaacaa aaaaggccaa cttcaaaagc tgccaacaat    240
gaatggctcc aaagatcccc ctgggtccta tgacttcgac ctgatcatca ttggaggagg    300
ctcaggagga ctggcagcag ctaaggaggc agccaaattt gacaagaaag tgctggtctt    360
ggattttgtc acaccgactc ctcttgggac cagatggggt ctcggaggaa cgtgtgtgaa    420
tgtgggttgc atacctaaga agctgatgca ccaggcagct ttgctcggac aagctctgaa    480
```

-continued

```
agactcgcgc aactatggct ggaaagtcga agacacagtg aagcatgact gggagaaaat      540
gacggaatct gtgcagagtc acatcggctc gctgaactgg ggctaccgcg tagctctccg      600
ggagaaaaag gtcgtctatg agaatgctta cgggaggttc attggtcctc acaggattgt      660
ggcgacaaat aacaaaggta aagaaaaaat ctattcagca gagcggttcc tcatcgccac      720
aggtgagagg ccccgctacc tgggcatccc tggagacaaa gagtactgca tcagcagtga      780 tgatctttc tccttgcctt actgcccggg gaagaccta gtagttggtg catcctatgt      840
cgccttggaa tgtgcaggat ttctggctgg tatcggctta gacgtcactg taatggtgcg      900
gtccattctc cttagaggat ttgaccaaga catggccaac aaaatcggtg aacacatgga      960
agaacatggt atcaagttta taaggcagtt cgtcccaacg aaaattgaac agatcgaagc      1020
aggaacacca ggccgactca gggtgactgc tcaatccaca aacagcgagg agaccataga      1080
gggcgaattt aacacagtgt tgctggcggt aggaagagat tcttgtacga gaactattgg      1140
cttagagacc gtgggcgtga agataaacga aaaaaccgga aagatacccg tcacggatga      1200
agagcagacc aatgtgcctt acatctacgc catcggtgac atcctggagg ggaagctaga      1260
gctgactccc gtagccatcc aggcggggag attgctggct cagaggctgt atggaggctc      1320
caatgtcaaa tgtgactatg acaatgtccc aacgactgta tttactcctt tggaatatgg      1380
ctgttgtggc ctctctgaag aaaaagccgt agagaaattt ggggaagaaa atattgaagt      1440
ttaccatagt ttctttttggc cattggaatg gacagtccca tcccgggata acaacaaatg      1500
ttatgcaaaa ataatctgca accttaaaga cgatgaacgt gtcgtgggct tccacgtgct      1560
gggtccaaac gctggagagg tgacgcaggg cttttgcggct gcgctcaagt gtgggctgac      1620
taagcagcag ctggacagca ccatcggcat ccacccggtc tgtgcagaga tattcacaac      1680
gttgtcagtg acgaagcgct ctggggaga catcctccag tctggctgct gaggttaagc      1740
cccagtgtgg atgctgttgc caagactaca gaccattgcc ttgcttcctt gcccacgccc      1800
aggtgaagtt caggaaggct cttgggtcct aggcgccaat tcaaggtgct gtcctaaggc      1860
caccgggtcc ctgggatctt gtgggtagga ggtggcaggt cgaaggaggc tgcagcatcg      1920 cactgggtc accatgacag actcagactg acatctggca gagcatcaca ggcatgcgtc      1980
catgaagtca ctggcctcaa gcccaagtgg tgggcagtga cagaagagct gccgggtctg      2040
ttgagctcaa ccttttcctg tagattgtct tagtctcact ttcaagctgt ctaatgtcaa      2100
ttctgttttt cttttttcct ccatgggggtt aatgatacta gagatagggga atattagcaa      2160 tcagtttttg tcatggctgg tccatctgca acagtcttta ctgtgtggaa gtgggtgaga      2220
tggcttatga gagccaaacc aatttatccc cagaaagacg aattaccctg tgactaaaat      2280
acactgtctg ctttttactaa ctggtgtagc attgtctcct ttaataagtc ttgtgtccaa      2340
aacgagaaaa accattggcc actttttgcaa gtttcctgca gtgtgcttag caagggaggt      2400
ggcgacttgg ctaatctact tgaactgcat cgcatggctc ttgggtagct tagagcatcg      2460
cagggtagag gcagaccagc agtgagtgtc tctcctggta caattattgt ctggttctca      2520
gtggaaaacg cttaatttgc tttaaacttg gtgttttttgt gaggtggatt tagtgtcttaag      2580 ctgtgtccca taagaactac attcacaggc aagtggctct tcctccacac agcctataca      2640
tcttctgagg taattacttt cataaggaag ctgttcataa cgtaagttat tattattatt      2700
gaacacaggg ggatgtgaag gatttttcat tgaaaaacca aatggttttt cttttttct      2760 gttcagtgag cccacaggaa ctctgtcagg acagccagta ctctgccggc atggctgctg      2820
```

```
gggcgtttac ggtgtagttt agctcctagg ttacatgacc gtgaacatgc tggctgagga    2880
ctacacaaac caggtttccc accatacacg gcctggccct gcagcttctt ttcttgccct    2940
cccctttgcc tgtccccacc tgcagtactg agtggcgttt cacagtaccc ttctgggcca    3000
cctcagggaa gggatttgcc tggtgtccag ccagcagcac ccaccctgcc ccacgaggct    3060
ccctcacacc tgcccccccg tccttgtgtt aagacagtg ggaagaggag aaaggaccag    3120
ggaaaccaag ggagttgact gttcagtttt atttatttat tttttaagtt ttttttttcct    3180 ttcaagtctg ccagtctctg agatcagaac aacagacagt gtagggtaac taatcatgtg    3240
attctcttag tggaatgaaa tgttctaccc ccacaagaag gagtatacgt cattgttcat    3300
attctgtaat cgcacaatgt attgtaatgc aaattccaat tccatgtatt tttattacaa    3360 ttttttctgga aaaaaatgtg aaccaataaa agatgttgat gcacacgcgt gccttct    3417
```

<210> SEQ ID NO 21
<211> LENGTH: 3505
<212> TYPE: DNA
<213> ORGANISM: Mus musculus

<400> SEQUENCE: 21

```
gtggctacga ggctggtgtt tttagccgcc atgcagagct tttctgagtt ctgggggtcc      60
tggagtcttg ctggcccggc tgcttaaggg tcggagtcca ctggcgagag tgacccaggg     120
cgcgtggcgt cccggaagcc ccgcccggag gaaggctcac tgccgctctg ctttgtgcca     180
cagagggcgg cggggccttg cagcggcgcg ggcgagcgga aaggccgcgg gaggcggcga     240
gccagcggaa ggtgcgaccg gcggagggcg gccatggtcc agccctgaag ccgaacaaaa     300
aaggccaact tcaaaagctg ccaacaatga atggctccaa agatccccct gggtcctatg     360
acttcgacct gatcatcatt ggaggaggct caggaggact ggcagcagct aaggaggcag     420
ccaaatttga caagaaagtg ctggtcttgg attttgtcac accgactcct cttgggacca     480 gatgggtct cggaggaacg tgtgtgaatg tgggttgcat acctaagaag ctgatgcacc     540
aggcagcttt gctcggacaa gctctgaaag actcgcgcaa ctatggctgg aaagtcgaag     600
acacagtgaa gcatgactgg gagaaaatga cggaatctgt gcagagtcac atcggctcgc     660
tgaactgggg ctaccgcgta gctctccggg agaaaaaggt cgtctatgag aatgcttacg     720
ggaggttcat tggtcctcac aggattgtgg cgacaaataa caaaggtaaa gaaaaaatct     780
attcagcaga gcggttcctc atcgccacag gtgagaggcc ccgctacctg ggcatccctg     840
gagacaaaga gtactgcatc agcagtgatg atcttttctc cttgccttac tgcccgggga     900
agaccctagt agttggtgca tcctatgtcg ccttggaatg tgcaggattt ctggctggta     960
tcggcttaga cgtcactgta atggtgcggt ccattctcct tagaggattt gaccaagaca    1020
tggccaacaa aatcggtgaa cacatggaag aacatggtat caagtttata aggcagttcg    1080
tcccaacgaa aattgaacag atcgaagcag gaacaccagg ccgactcagg gtgactgctc    1140
aatccacaaa cagcgaggag accatagagg gcgaatttaa cacagtgttg ctggcggtag    1200
gaagagattc ttgtacgaga actattggct tagagaccgt gggcgtgaag ataaacgaaa    1260
aaaccggaaa gataccgtc acggatgaag agcagaccaa tgtgccttac atctacgcca    1320
tcggtgacat cctggagggg aagctagagc tgactcccgt agccatccag gcggggagat    1380
tgctggctca gaggctgtat ggaggctcca atgtcaaatg tgactatgac aatgtcccaa    1440
cgactgtatt tactcctttg gaatatggct gttgtgcct ctctgaagaa aaagccgtag    1500
agaaatttgg ggaagaaaat attgaagttt accatagttt cttttggcca ttggaatgga    1560
```

-continued

```
cagtcccatc ccgggataac aacaaatgtt atgcaaaaat aatctgcaac cttaaagacg      1620
atgaacgtgt cgtgggcttc cacgtgctgg gtccaaacgc tggagaggtg acgcagggct      1680
ttgcggctgc gctcaagtgt gggctgacta agcagcagct ggacagcacc atcggcatcc      1740
acccggtctg tgcagagata ttcacaacgt tgtcagtgac gaagcgctct gggggagaca      1800
tcctccagtc tggctgctga ggttaagccc cagtgtggat gctgttgcca agactacaga      1860
ccattgcctt gcttccttgc ccacgcccag gtgaagttca ggaaggctct tgggtcctag      1920
gcgccaattc aaggtgctgt cctaaggcca ccgggtccct gggatcttgt gggtaggagg      1980
tggcaggtcg aaggaggctg cagcatcgca ctggggtcac catgacagac tcagactgac      2040
atctggcaga gcatcacagg catgcgtcca tgaagtcact ggcctcaagc ccaagtggtg      2100
ggcagtgaca aagagctgc cgggtctgtt gagctcaacc ttttcctgta gattgtctta      2160
gtctcacttt caagctgtct aatgtcaatt ctgttttttct tttttcctcc atggggttaa      2220
tgatactaga gatagggaat attagcaatc agttttttgtc atggctggtc catctgcaac      2280
agtctttact gtgtggaagt gggtgagatg gcttatgaga gccaaaccaa tttatcccca      2340
gaaagacgaa ttaccctgtg actaaaatac actgtctgct tttactaact ggtgtagcat      2400
tgtctccttt aataagtctt gtgtccaaaa cgagaaaaac cattggccac ttttgcaagt      2460
ttcctgcagt gtgcttagca agggaggtgg cgacttggct aatctacttg aactgcatcg      2520
catggctctt gggtagctta gagcatcgca gggtagaggc agaccagcag tgagtgtctc      2580
tcctggtaca attattgtct ggttctcagt ggaaaacgct taatttgctt taaacttggt      2640 gttttttgtga ggtggattta gtcttaagct gtgtcccata agaactacat tcacaggcaa      2700
gtggctcttc ctcccacacag cctatacatc ttctgaggta attactttca taaggaagct      2760
gttcataacg taagttatta ttattattga acacaggtgg atgtgaagga tttttcattg      2820
aaaaaccaaa tggttttttct tttttttctgt tcagtgagcc cacaggaact ctgtcaggac      2880
agccagtact ctgccggcat ggctgctggg gcgtttacgg tgtagtttag ctcctaggtt      2940
acatgaccgt gaacatgctg gctgaggact acacaaacca ggtttcccac catacacggc      3000
ctggccctgc agcttctttt cttgccctcc cctttgcctg tccccacctg cagtactgag      3060
tggcgtttca cagtaccctt ctgggccacc tcagggaagg gatttgcctg gtgtccagcc      3120
agcagcaccc accctgcccc acgaggctcc ctcacacctg ccccccgtc cttgtgttga      3180 agacagtggg aagaggagaa aggaccaggg aaaccaaggg agttgactgt tcagttttat      3240
ttatttattt tttaagtttt ttttttccttt caagtctgcc agtctctgag atcagaacaa      3300
cagacagtgt agggtaacta atcatgtgat tctcttagtg gaatgaaatg ttctaccccc      3360
acaagaagga gtatacgtca ttgttcatat tctgtaatcg cacaatgtat tgtaatgcaa      3420
attccaattc catgtatttt tattacaatt tttctggaaa aaaatgtgaa ccaataaaag      3480
atgttgatgc acacgcgtgc cttct                                           3505
```

```
<210> SEQ ID NO 22
<211> LENGTH: 3310
<212> TYPE: DNA
<213> ORGANISM: Mus musculus

<400> SEQUENCE: 22
agtttgcttc cgtcaggcct cgcgtccacg cgggaggtgc gggacgccga caccgcgggg       60
cgagaagagc tggtggtttc accttccttg ttcatccgaa caaaaaaggc caacttcaaa      120
```

-continued

```
agctgccaac aatgaatggc tccaaagatc cccctgggtc ctatgacttc gacctgatca    180
tcattggagg aggctcagga ggactggcag cagctaagga ggcagccaaa tttgacaaga    240
aagtgctggt cttggatttt gtcacaccga ctcctcttgg gaccagatgg ggtctcggag    300
gaacgtgtgt gaatgtgggt tgcataccta agaagctgat gcaccaggca gctttgctcg    360
gacaagctct gaaagactcg cgcaactatg gctggaaagt cgaagacaca gtgaagcatg    420
actgggagaa aatgacggaa tctgtgcaga gtcacatcgg ctcgctgaac tggggctacc    480
gcgtagctct ccgggagaaa aaggtcgtct atgagaatgc ttacgggagg ttcattggtc    540
ctcacaggat tgtggcgaca aataacaaag gtaaagaaaa aatctattca gcagagcggt    600
tcctcatcgc cacaggtgag aggccccgct acctgggcat ccctggagac aaagagtact    660
gcatcagcag tgatgatctt ttctccttgc cttactgccc ggggaagacc ctagtagttg    720
gtgcatccta tgtcgccttg aatgtgcag gatttctggc tggtatcggc ttagacgtca    780
ctgtaatggt gcggtccatt ctccttagag gatttgacca agacatggcc aacaaaatcg    840
gtgaacacat ggaagaacat ggtatcaagt ttataaggca gttcgtccca acgaaaattg    900
aacagatcga agcaggaaca ccaggccgac tcagggtgac tgctcaatcc acaaacagcg    960
aggagaccat agagggcgaa tttaacacag tgttgctggc ggtaggaaga gattcttgta   1020
cgagaactat tggcttagag accgtgggcg tgaagataaa cgaaaaaacc ggaaagatac   1080
ccgtcacgga tgaagagcag accaatgtgc cttacatcta cgccatcggt gacatcctgg   1140
aggggaagct agagctgact cccgtagcca tccaggcggg gagattgctg gctcagaggc   1200
tgtatggagg ctccaatgtc aaatgtgact atgacaatgt cccaacgact gtatttactc   1260
ctttggaata tggctgttgt ggcctctctg aagaaaaagc cgtagagaaa tttgggggaag   1320 aaaatattga gtttaccat agtttctttt ggccattgga atggacagtc ccatcccggg   1380
ataacaacaa atgttatgca aaaataatct gcaaccttaa agacgatgaa cgtgtcgtgg   1440
gcttccacgt gctgggtcca aacgctggag aggtgacgca gggctttgcg gctgcgctca   1500
agtgtgggct gactaagcag cagctggaca gcaccatcgg catccacccg gtctgtgcag   1560
agatattcac aacgttgtca gtgacgaagc gctctggggg agacatcctc cagtctggct   1620
gctgaggtta agccccagtg tggatgctgt tgccaagact acagaccatt gccttgcttc   1680
cttgcccacg cccaggtgaa gttcaggaag gctcttgggt cctaggcgcc aattcaaggt   1740
gctgtcctaa ggccaccggg tccctgggat cttgtgggta ggaggtggca ggtcgaagga   1800
ggctgcagca tcgcactggg gtcaccatga cagactcaga ctgacatctg gcagagcatc   1860
acaggcatgc gtccatgaag tcactggcct caagcccaag tggtgggcag tgacagaaga   1920
gctgccgggt ctgttgagct caaccttttc ctgtagattg tcttagtctc actttcaagc   1980
tgtctaatgt caattctgtt tttctttttt cctccatggg gttaatgata ctagagatag   2040
ggaatattag caatcagttt ttgtcatggc tggtccatct gcaacagtct ttactgtgtg   2100
gaagtgggtg agatggctta tgagagccaa accaatttat ccccagaaag acgaattacc   2160
ctgtgactaa aatacactgt ctgcttttac taactggtgt agcattgtct cctttaataa   2220
gtcttgtgtc caaacgagaaaaaccattg gccactttttg caagtttcct gcagtgtgct   2280
tagcaaggga ggtggcgact tggctaatct acttgaactg catcgcatgg ctcttgggta   2340
gcttagagca tcgcagggta gaggcagacc agcagtgagt gtctctcctg gtacaattat   2400
tgtctggttc tcagtggaaa acgcttaatt tgctttaaac ttggtgtttt tgtgaggtgg   2460
atttagtctt aagctgtgtc ccataagaac tacattcaca ggcaagtggc tcttcctcca   2520
```

-continued

```
cacagcctat acatcttctg aggtaattac tttcataagg aagctgttca taacgtaagt    2580
tattattatt attgaacaca ggtggatgtg aaggattttt cattgaaaaa ccaaatggtt    2640
tttctttttt tctgttcagt gagcccacag gaactctgtc aggacagcca gtactctgcc    2700
ggcatggctg ctggggcgtt tacggtgtag tttagctcct aggttacatg accgtgaaca    2760
tgctggctga ggactacaca aaccaggttt cccaccatac acggcctggc cctgcagctt    2820
cttttcttgc cctccccttt gcctgtcccc acctgcagta ctgagtggcg tttcacagta    2880
cccttctggg ccacctcagg gaagggattt gcctggtgtc cagccagcag cacccaccct    2940
gccccacgag gctccctcac acctgccccc ccgtccttgt gttgaagaca gtgggaagag    3000
gagaaaggac cagggaaacc aagggagttg actgttcagt tttatttatt tattttttaa    3060
gttttttttt cctttcaagt ctgccagtct ctgagatcag aacaacagac agtgtagggt    3120
aactaatcat gtgattctct tagtggaatg aaatgttcta ccccccacaag aaggagtata    3180 cgtcattgtt catattctgt aatcgcacaa tgtattgtaa tgcaaattcc aattccatgt    3240
atttttatta caatttttct ggaaaaaaat gtgaaccaat aaaagatgtt gatgcacacg    3300
cgtgccttct                                                          3310

<210> SEQ ID NO 23
<211> LENGTH: 3634
<212> TYPE: DNA
<213> ORGANISM: Mus musculus

<400> SEQUENCE: 23
caggctccac cagtgcttct gcagacctca gagcctggcg gctggcctca taaacagccg     60
tgcggtggac actctactaa gtgccctgca ttgaaggaga agccctggtc accatgccag    120
ttgatgactg ctggctgtac ttcccagctt ctcgaggtag aacctttgtg cagactgtct    180
gggtggcacc cacttgcccc aactgttgct ggtttccagg ttttctccct ccagtccccc    240
ggccaccaca tgtgccccgt gtgctgctga ggggccctcg tggggctgtg cttcctgctt    300
cacgtccctc caagacactc ccctcctcat cccagacgcc ctgtcctact gacccctgta    360
tctgccctcc accctccaca cctgatagta ggcaggaaaa aaatacgcaa tctgagctgc    420
cgaacaaaaa aggccaactt caaaagctgc aacaatgaa tggctccaaa gatcccctg    480 ggtcctatga cttcgacctg atcatcattg aggaggctc aggaggactg gcagcagcta    540
aggaggcagc caaatttgac aagaaagtgc tggtcttgga ttttgtcaca ccgactcctc    600
ttgggaccag atggggtctc ggaggaacgt gtgtgaatgt gggttgcata cctaagaagc    660
tgatgcacca ggcagctttg ctcggacaag ctctgaaaga ctcgcgcaac tatggctgga    720
aagtcgaaga cacagtgaag catgactggg agaaaatgac ggaatctgtg cagagtcaca    780
tcggctcgct gaactggggc taccgcgtag ctctccggga gaaaaaggtc gtctatgaga    840
atgcttacgg gaggttcatt ggtcctcaca ggattgtggc gacaaataac aaaggtaaag    900
aaaaaatcta ttcagcagag cggttcctca tcgccacagg tgagaggccc cgctacctgg    960
gcatccctgg agacaaagag tactgcatca gcagtgatga tctttctcc ttgccttact   1020 gcccggggaa gaccctagta gttggtgcat cctatgtcgc cttggaatgt gcaggatttc   1080
tggctggtat cggcttagac gtcactgtaa tggtgcggtc cattctcctt agaggatttg   1140
accaagacat ggccaacaaa atcggtgaac acatggaaga acatggtatc aagtttataa   1200
ggcagttcgt cccaacgaaa attgaacaga tcgaagcagg aacaccaggc cgactcaggg   1260
```

-continued

```
tgactgctca atccacaaac agcgaggaga ccatagaggg cgaatttaac acagtgttgc   1320
tggcggtagg aagagattct tgtacgagaa ctattggctt agagaccgtg ggcgtgaaga   1380
taaacgaaaa aaccggaaag atacccgtca cggatgaaga gcagaccaat gtgccttaca   1440
tctacgccat cggtgacatc ctggagggga agctagagct gactcccgta gccatccagg   1500
cggggagatt gctggctcag aggctgtatg gaggctccaa tgtcaaatgt gactatgaca   1560
atgtcccaac gactgtattt actcctttgg aatatggctg ttgtggcctc tctgaagaaa   1620
aagccgtaga gaaatttggg gaagaaaata ttgaagttta ccatagtttc ttttggccat   1680
tggaatggac agtcccatcc cgggataaca acaaatgtta tgcaaaaata atctgcaacc   1740
ttaaagacga tgaacgtgtc gtgggcttcc acgtgctggg tccaaacgct ggagaggtga   1800
cgcagggctt tgcggctgcg ctcaagtgtg ggctgactaa gcagcagctg gacagcacca   1860
tcggcatcca cccggtctgt gcagagatat tcacaacgtt gtcagtgacg aagcgctctg   1920
ggggagacat cctccagtct ggctgctgag gttaagcccc agtgtggatg ctgttgccaa   1980
gactacagac cattgccttg cttccttgcc cacgcccagg tgaagttcag gaaggctctt   2040
gggtcctagg cgccaattca aggtgctgtc ctaaggccac cgggtccctg ggatcttgtg   2100
ggtaggaggt ggcaggtcga aggaggctgc agcatcgcac tggggtcacc atgacagact   2160
cagactgaca tctggcagag catcacaggc atgcgtccat gaagtcactg gcctcaagcc   2220
caagtggtgg gcagtgacag aagagctgcc gggtctgttg agctcaacct tttcctgtag   2280
attgtcttag tctcactttc aagctgtcta atgtcaattc tgttttctt ttttcctcca    2340 tggggttaat gatactagag atagggaata ttagcaatca gtttttgtca tggctggtcc   2400
atctgcaaca gtctttactg tgtggaagtg ggtgagatgg cttatgagag ccaaaccaat   2460
ttatccccag aaagacgaat taccctgtga ctaaaataca ctgtctgctt ttactaactg   2520
gtgtagcatt gtctccttta ataagtcttg tgtccaaaac gagaaaaacc attggccact   2580
tttgcaagtt tcctgcagtg tgcttagcaa gggaggtggc gacttggcta atctacttga   2640
actgcatcgc atggctcttg ggtagcttag agcatcgcag ggtagaggca gaccagcagt   2700
gagtgtctct cctggtacaa ttattgtctg gttctcagtg gaaaacgctt aatttgcttt   2760
aaacttggtg tttttgtgag gtggatttag tcttaagctg tgtcccataa gaactacatt   2820
cacaggcaag tggctcttcc tccacacagc ctatacatct tctgaggtaa ttactttcat   2880
aaggaagctg ttcataacgt aagttattat tattattgaa cacaggtgga tgtgaaggat   2940
ttttcattga aaaaccaaat ggttttttct ttttttctgtt cagtgagccc acaggaactc   3000
tgtcaggaca gccagtactc tgccggcatg gctgctgggg cgtttacggt gtagtttagc   3060
tcctaggtta catgaccgtg aacatgctgg ctgaggacta cacaaaccag gtttcccacc   3120
atacacggcc tggccctgca gcttcttttc ttgccctccc ctttgcctgt ccccacctgc   3180
agtactgagt ggcgtttcac agtacccttc tgggccacct cagggaaggg atttgcctgg   3240
tgtccagcca gcagcaccca ccctgcccca cgaggctccc tcacacctgc cccccgtcc    3300 ttgtgttgaa gacagtggga agaggagaaa ggaccaggga aaccaaggga gttgactgtt   3360 cagtttttatt tatttatttt ttaagttttt ttttcctttc aagtctgcca gtctctgaga   3420
tcagaacaac agacagtgta gggtaactaa tcatgtgatt ctcttagtgg aatgaaatgt   3480 tctacccca caagaaggag tatacgtcat tgttcatatt ctgtaatcgc acaatgtatt    3540
gtaatgcaaa ttccaattcc atgtattttt attacaattt ttctggaaaa aaatgtgaac   3600
caataaaaga tgttgatgca cacgcgtgcc ttct                               3634
```

-continued

```
<210> SEQ ID NO 24
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 24
nnnnnnnnnn nnnnnnnnnn gtttttgtac tctcaagatt tagaaataaa tcttgcagaa        60
gctacaaaga taaggcttca tgccgaaatc aacaccctgt cattttatgg cagggtgttt       120
tcgttattta atttttt                                                      137

<210> SEQ ID NO 25
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 25
nnnnnnnnnn nnnnnnnnnn gtttttgtac tctcagaaat gcagaagcta caaagataag        60
gcttcatgcc gaaatcaaca ccctgtcatt ttatggcagg gtgttttcgt tatttaattt       120
ttt                                                                     123

<210> SEQ ID NO 26
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 26
nnnnnnnnnn nnnnnnnnnn gtttttgtac tctcagaaat gcagaagcta caaagataag        60
gcttcatgcc gaaatcaaca ccctgtcatt ttatggcagg gtgttttttt                  110

<210> SEQ ID NO 27
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 27
nnnnnnnnnn nnnnnnnnnn gttttagagc tagaaatagc aagttaaaat aaggctagtc        60
```

-continued

```
cgttatcaac ttgaaaaagt ggcaccgagt cggtgctttt tt                    102

<210> SEQ ID NO 28
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 28
nnnnnnnnnn nnnnnnnnnn gttttagagc tagaaatagc aagttaaaat aaggctagtc       60
cgttatcaac ttgaaaaagt gttttttt                                          88

<210> SEQ ID NO 29
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 29
nnnnnnnnnn nnnnnnnnnn gttttagagc tagaaatagc aagttaaaat aaggctagtc       60
cgttatcatt tttttt                                                       76
```

COMPOSITIONS AND METHODS FOR TREATING RAS-MUTANT CANCERS

CROSS-REFERENCE TO RELATED APPLICATIONS

This application is a U.S. National Stage Application under 35 U.S.C. § 371 of International Patent Application No. PCT/US2020/029513, filed on Apr. 23, 2020, which claims the benefit of and priority to U.S. Provisional Patent Application No. 62/838,065, filed Apr. 24, 2019, the entire contents of each of which are incorporated herein by reference.

SEQUENCE LISTING

The instant application contains a Sequence Listing which has been submitted electronically in ASCII format and is hereby incorporated by reference in its entirety. Said ASCII copy, created on May 18, 2020, is named 115872-0876_SL.txt and is 61,580 bytes in size.

TECHNICAL FIELD

The present technology relates generally to compositions and methods for treating, preventing, and/or ameliorating a RAS-mutant cancer in a subject in need thereof. In particular, the present technology relates to methods for treating, preventing, and/or ameliorating RAS-mutant pancreatic cancer by administration of a therapeutically effective amount of a TXNRD1 inhibitor.

BACKGROUND

The following description of the background of the present technology is provided simply as an aid in understanding the present technology and is not admitted to describe or constitute prior art to the present technology.

About 90% of all pancreatic cancers are pancreatic ductal adenocarcinoma (PDAC), which is one of the deadliest types of cancer. PDAC has only a 7% 5-year survival rate. Detailed genetic profiles have suggested significant variability among cancers. For example, genome sequencing has revealed that the genes that are frequently mutated in PDAC include KRAS, TP53, CDKN2A, SMAD4, MLL3, TGFBR2, ARID1A and SF3B1, EPC1 and ARID2, ATM, ZIM2, MAP2K4, NALCN, SLC16A4, MAGEA6, ROBO2, KDM6A, PREX2, ERBB2, MET, FGFR1, CDK6, PIK3R3, PIK3CA, BRCA1, BRCA2, PALB2, etc. Despite the variability, it is clear that KRAS is mutated in 95% of PDAC cases. See, e.g., Biankin et al., *Nature* 491(7424): 399-405 (2012); Waddell et al., *Nature* 518(7540):495-501 (2015); and Jones et al., *Science* 321(5897): 1801-1806 (2008).

KRAS protein is a GTPase that plays an important role in cellular signal transduction pathways. KRAS protein is considered to act as a binary ON-OFF switch, cycling between an active guanosine triphosphate (GTP)-bound and inactive guanosine diphosphate (GDP)-bound state. In normal quiescent cells, KRAS is mostly found in the GDP-bound inactive state. Cell-surface receptors transiently promote formation of the active KRAS-GTP, in response to extracellular stimuli. The KRAS mutations in PDAC and other types of cancer are typically missense mutations that render KRAS protein constitutively GTP-bound, resulting in overstimulation of signaling pathways that drive cancer growth. The oncogenic mutant KRAS protein drives tumor progression in multiple cancer types. For example, in case of PDAC, the mutant KRAS proteins regulate reprogramming of pancreatic acinar cell to ductal cell intraepithelial neoplasia. KRAS is also required in the growth and maintenance of PDAC and other cancers. See, e.g., Ying et al., *Cell* 149(3):656-70 (2012). Indeed, PDAC is considered to be one of the most "KRAS-addicted" types of cancer.

Accordingly, KRAS is considered an important therapeutic target against PDAC and other KRAS mutant cancers. See, e.g., Waters and Der, Cold Spring Harb PerspectMed. 8(9): a031435 (2018).

SUMMARY OF THE PRESENT TECHNOLOGY

In one aspect, the present disclosure provides methods for treating a RAS-mutant cancer in a subject in need thereof, comprising administering to the subject a therapeutically effective amount of a TXNRD1 inhibitor selected from the group consisting of auranofin, Piperlongumine, D9, TRi-1, TRi-2, Myricetin, PMX464, PX12, brevetoxin-2, manumycin A, ethaselen, aurothioglucose, protoporphyrin IX, an anti-TXNRD1 antibody, and any derivatives thereof. Also disclosed herein are methods for treating a RAS-mutant cancer in a subject in need thereof, comprising administering to the subject a therapeutically effective amount of an inhibitory nucleic acid that inhibits TXNRD1 expression. In some embodiments, the inhibitory nucleic acid comprises a sequence selected from the group consisting of TCTAATATCATTAACACCATGG (SEQ ID NO: 1; human shTXNRD1), TAAATAAAACTGAATATGGTCA (SEQ ID NO: 2; human shTXNRD1), TTAATAATAACTTATGATATTA (SEQ ID NO: 3; human shTXNRD1), TTTGTAACAAAAATACATGGAA (SEQ ID NO: 4; human shTXNRD1), TTTAAATGAAAATCCTTCACAT (SEQ ID NO: 5; human shTXNRD1), TTTTAAATGAAAATCCTTCACA (SEQ ID NO: 6; human shTXNRD1), TAAGAAAAGAGAATCACAACAT (SEQ ID NO: 7; human shTXNRD1), TTTTCATTTATCTTCACCCCTA (SEQ ID NO: 8; human shTXNRD1), TTAGAAAGAAATAGATACCCAA (SEQ ID NO: 9; human shTXNRD1), TAATAATAACTTATGATATTAA (SEQ ID NO: 10; human shTXNRD1), TTTAGTCACAGGGTAATTCGTC (SEQ ID NO: 11; murine shTxnrd1), and TTCGTCACTGACAACGTTGTGA (SEQ ID NO: 12; murine shTxnrd1), or any complement thereof. The RAS-mutant cancer may be lung cancer (e.g., lung adenocarcinoma), mucinous adenoma, pancreatic cancer (e.g., PDAC), colorectal cancer, skin cancer (e.g., melanoma), endometrial cancer, testicular germ cell cancer, or adrenal gland cancer. In certain embodiments, the RAS-mutant cancer comprises a KRAS, NRAS, or HRAS mutation selected from the group consisting of G12C, G12D, G12V, G12A, G12S, G12R, G13D, G13C, G13S, G13R, G13A, G13V, Q61H, Q61L, Q61R, Q61K, Q61P, and Q61E. Additionally or alternatively, in some embodiments, the KRAS, NRAS, or HRAS mutation is detected via DNA sequencing.

Additionally or alternatively, in some embodiments of the methods disclosed herein, the subject displays elevated expression levels of RAS protein (e.g., KRAS, HRAS, NRAS) in cancer cells prior to treatment. In any of the embodiments of the methods disclosed herein, the subject exhibits one or more signs or symptoms selected from among pain in the upper abdomen that radiates towards the back, loss of appetite or unintended weight loss, depression, new-onset diabetes, blood clots, fatigue, yellowing of skin and the whites of eyes (jaundice), bloating, nausea, and vomiting.

Additionally or alternatively, in some embodiments of the methods disclosed herein, the subject harbors one or more point mutations in TP53, CDKN2A, SMAD4, MLL3, TGFBR2, ARID1A, SF3B1, EPC1, ARID2, ATM, ZIM2, MAP2K4, NALCN, SLC16A4, MAGEA6, ROBO2, KDM6A, PREX2, ERBB2, MEL, FGFR1, CDK6, PIK3R3, PIK3CA, BRCA1, BRCA2, or PALB2. In some embodiments, the subject is human.

In any of the embodiments of the methods disclosed herein, the TXNRD1 inhibitor or the inhibitory nucleic acid that inhibits TXNRD1 expression may be administered orally, topically, intranasally, systemically, intravenously, subcutaneously, intraperitoneally, intradermally, intraocularly, iontophoretically, transmucosally, or intramuscularly. In some embodiments, the TXNRD1 inhibitor or the inhibitory nucleic acid is administered daily for 6 weeks or more. In other embodiments, the TXNRD1 inhibitor or the inhibitory nucleic acid is administered daily for 12 weeks or more.

Additionally or alternatively, in some embodiments, the methods further comprise separately, sequentially or simultaneously administering one or more additional therapeutic agents to the subject. Examples of the additional therapeutic agents include, but are not limited to, paclitaxel, gemcitabine, AMG 510, 5-FU (fluorouracil), and irinotecan.

In another aspect, the present disclosure provides a method for monitoring the therapeutic efficacy of a TXNRD1 inhibitor in a subject diagnosed with a RAS-mutant cancer comprising: (a) detecting TXNRD1 protein levels in a test sample obtained from the subject after the subject has been administered the TXNRD1 inhibitor; and (b) determining that the TXNRD1 inhibitor is effective when the TXNRD1 protein levels in the test sample are reduced compared to that observed in a control sample obtained from the subject prior to administration of the TXNRD1 inhibitor. Examples of TXNRD1 inhibitors include auranofin, Piperlongumine, D9, TRi-1, TRi-2, Myricetin, PMX464, PX12, brevetoxin-2, manumycin A, ethaselen, aurothioglucose, protoporphyrin IX, an anti-TXNRD1 antibody, an inhibitory nucleic acid that inhibits TXNRD1 expression, or any derivatives thereof. In some embodiments, the inhibitory RNA is a shRNA, an antisense oligonucleotide, or a sgRNA.

In one aspect, the present disclosure provides a method for inhibiting RAS-mutant cell proliferation in a subject in need thereof, comprising administering to the subject a therapeutically effective amount of at least one TXNRD1 inhibitor, wherein the at least one TXNRD1 inhibitor is selected from the group consisting of auranofin, Piperlongumine, D9, TRi-1, TRi-2, Myricetin, PMX464, PX12, brevetoxin-2, manumycin A, ethaselen, aurothioglucose, protoporphyrin IX, an anti-TXNRD1 antibody, an inhibitory nucleic acid that inhibits TXNRD1 expression, and any derivatives thereof, and wherein the subject suffers from a disease or condition characterized by elevated expression levels and/or increased activity of RAS (e.g., KRAS, HRAS, NRAS) and/or TXNRD1. In some embodiments, the inhibitory nucleic acid comprises a nucleic acid sequence selected from the group consisting of TCTAATATCATTAACAC-CATGG (SEQ ID NO: 1; human shTXNRD1), TAAATAAAACTGAATATGGTCA (SEQ ID NO: 2; human shTXNRD1), TTAATAATAACTTATGATATTA (SEQ ID NO: 3; human shTXNRD1), TTTGTAACAAAAATA-CATGGAA (SEQ ID NO: 4; human shTXNRD1), TTTAAATGAAAATCCTTCACAT (SEQ ID NO: 5; human shTXNRD1), TTTTAAATGAAAATCCTTCACA (SEQ ID NO: 6; human shTXNRD1), TAAGAAAAGAGAAT-CACAACAT (SEQ ID NO: 7; human shTXNRD1), TTTT-CATTTATCTTCACCCCTA (SEQ ID NO: 8; human shTXNRD1), TTAGAAAGAAATAGATACCCAA (SEQ ID NO: 9; human shTXNRD1), TAATAATAACTTATGA-TATTAA (SEQ ID NO: 10; human shTXNRD1), TTTAGT-CACAGGGTAATTCGTC (SEQ ID NO: 11; murine shTxnrd1), and TTCGTCACTGACAACGTTGTGA (SEQ ID NO: 12; murine shTxnrd1).

In any and all embodiments of the methods disclosed herein, TXNRD1 and/or RAS (e.g., KRAS, HRAS, NRAS) expression levels are detected via RNA-seq, northern blotting, microarrays, dot or slot blots, fluorescent in situ hybridization, Reverse transcription polymerase chain reaction (RT-PCR), ribonuclease protection assay (RPA), real-time quantitative RT-PCR, high-performance liquid chromatography (HPLC), liquid chromatography-mass spectrometry (LC/MS), enzyme-linked immunosorbent assay (ELISA), immunoprecipitation, immunoelectrophoresis, immunostaining, immunohistochemistry, or western blotting.

Additionally or alternatively, in some embodiments of the methods disclosed herein, the method further comprises administering to the subject a therapeutically effective amount of gemcitabine. In any of the preceding embodiments of the methods disclosed herein, the method further comprises administering to the subject a therapeutically effective amount of a $KRAS^{G12C}$ inhibitor, optionally wherein the $KRAS^{G12C}$ inhibitor is AMG 510.

BRIEF DESCRIPTION OF THE DRAWINGS

FIG. 3B shows a bar graph demonstrating validation of candidate genes obtained from FIG. 3A. Competitive proliferation assays were performed in mPDAC cells, mHCC cells, and nontransformed immortalized mouse embryonic fibroblasts (iMEF). These cells were transduced with a Venus$^+$ virus carrying an inducible shRNA. The following controls shRNAs were used: Ren.713 (a non-targeting shRNA serving as a negative control), Rpa3.561 (a positive control for growth inhibition in all proliferating cells), Kras.247 (a positive control for mPDAC-specific growth inhibition). G418-selected Venus$^+$ cells were mixed with untransduced cells and cultured in the presence of doxycycline to induce shRNA. The percentage of Venus$^+$ and dsRed$^+$ (shRNA-expressing) cells was determined at different time points (T0: day 0; T12: day 12). Changes served as readout of growth inhibitory effects of the expressed shRNA.

FIGS. 7A-7D show the antiproliferative effects of TXNRD1 inhibitor Auranofin in KRAS-mutant pancreatic cancer cells and potential synergistic inhibitory effects when combined with Gemcitabine. FIG. 7A shows dose-dependent effects of Auranofin, Gemcitabine, and their combination on MIAPaCa-2 (KRAS$^{G12C}$) and PSN1 (KRAS$^{G12R}$) pancreatic cancer cell lines. FIG. 7B shows percent growth inhibition at each concentration of Auranofin and Gemcitabine in MIAPaCa-2 (KRAS$^{G12C}$) and PSN1 (KRAS$^{G12R}$)

Figure 7A:
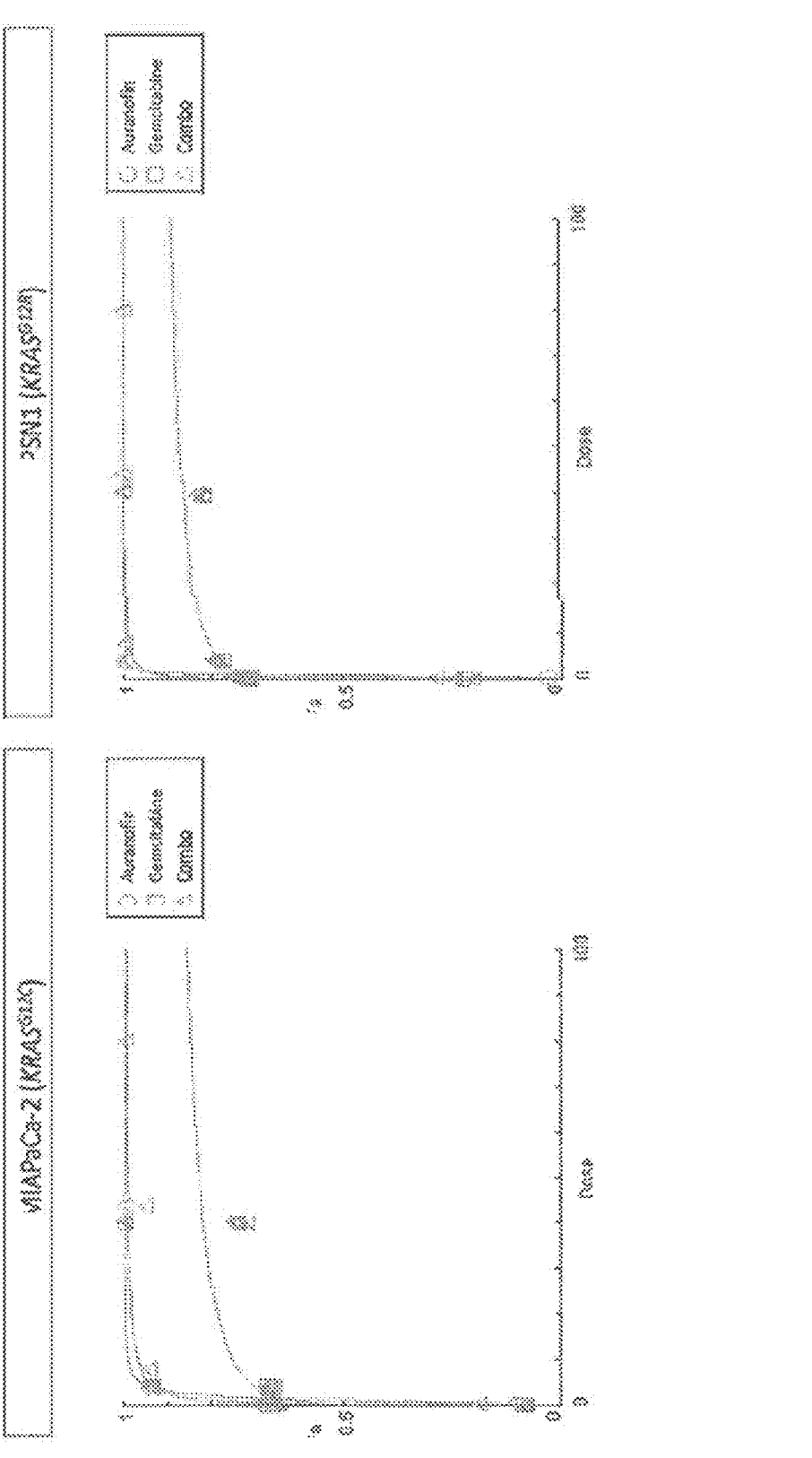
Figure 7B:
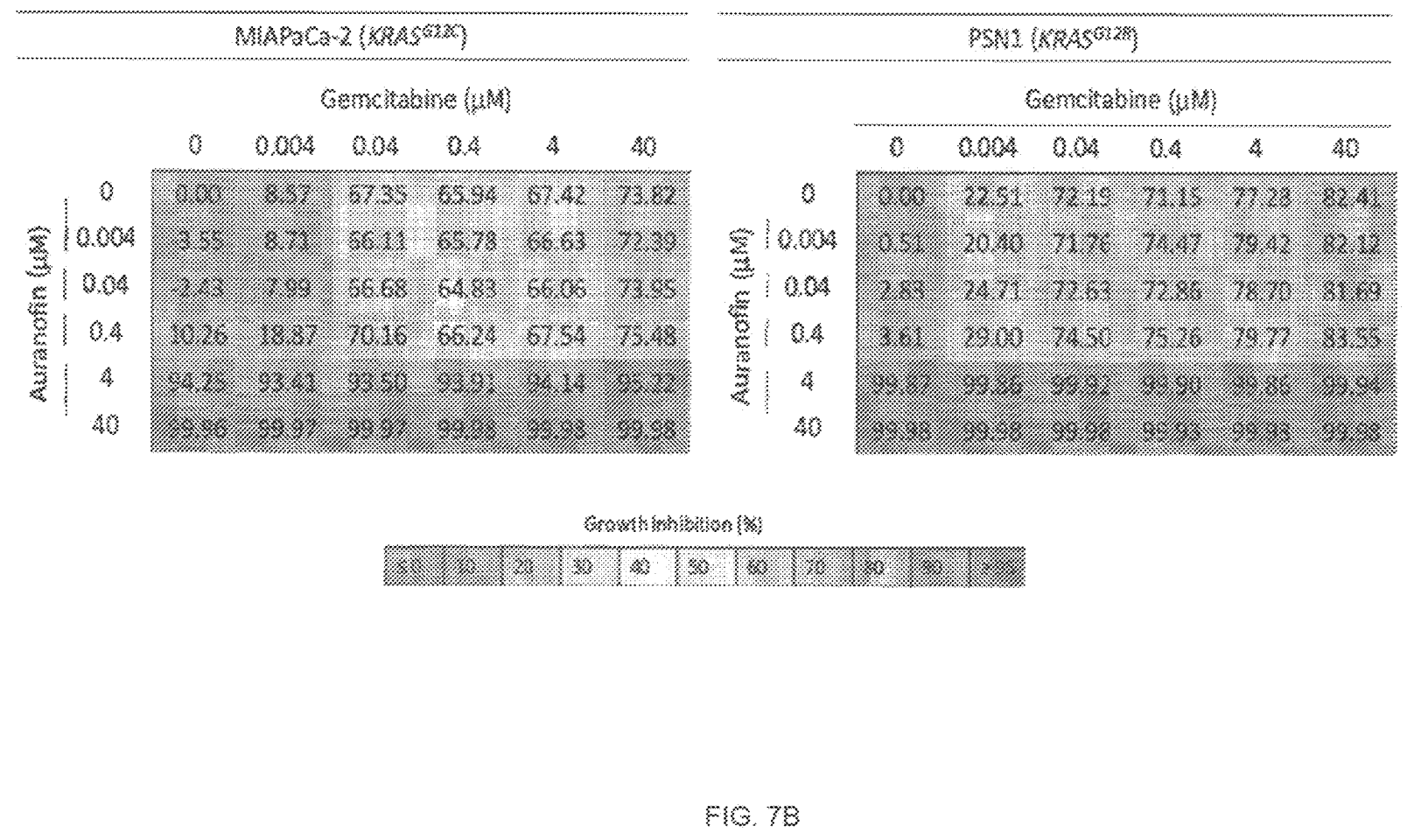
Figure 7C:
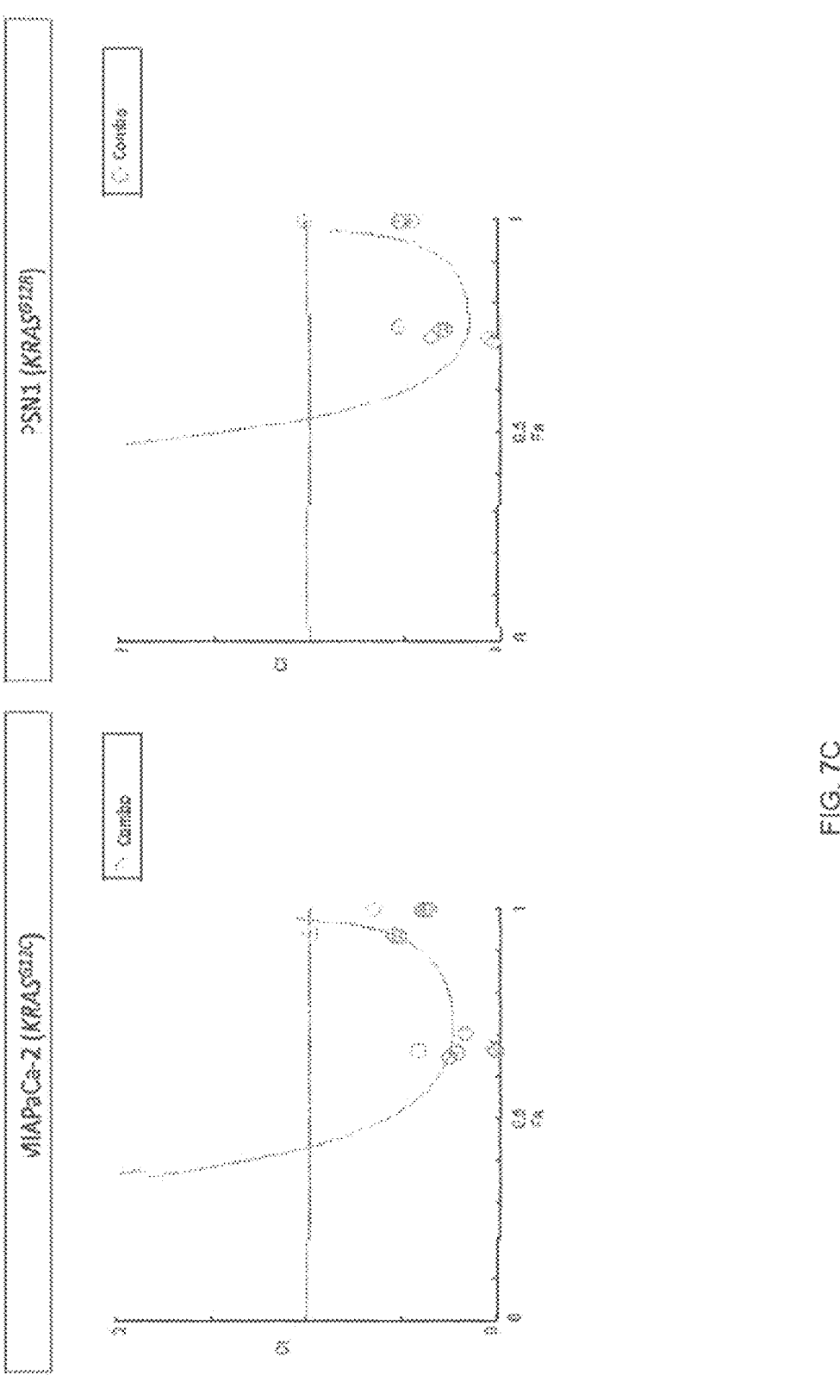
Figure 7D:
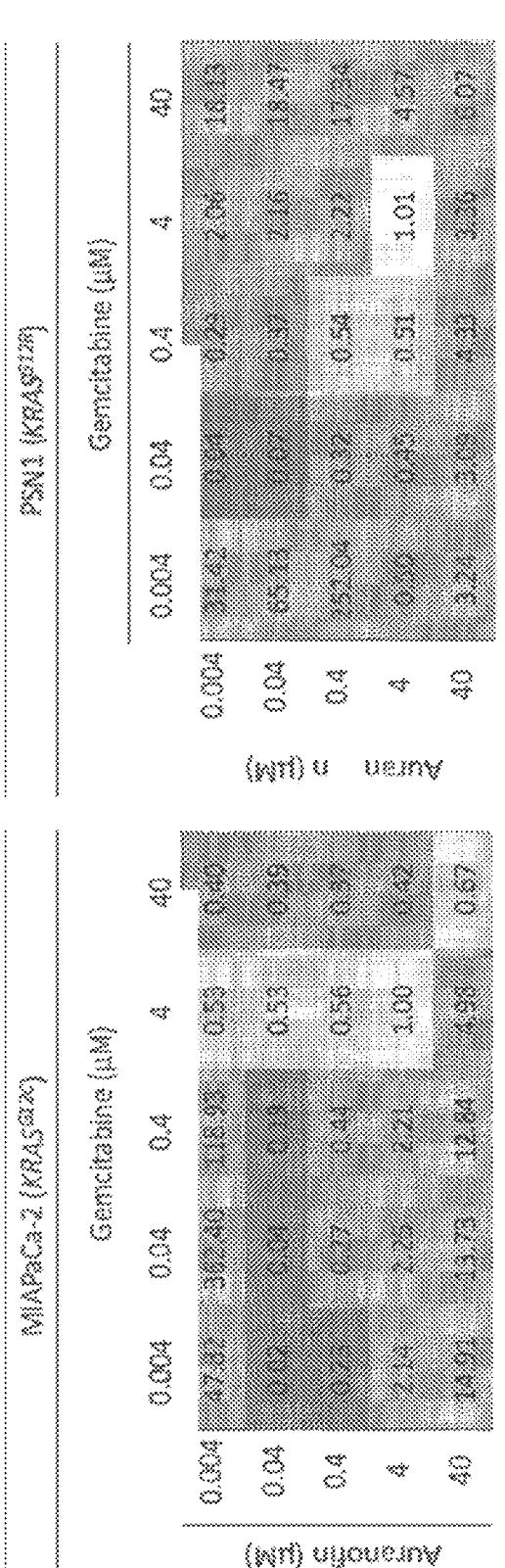
Figure 7D:

7                                                                    8 cells from FIG. 7A. Data presented as mean of three independent experiments (n=3). FIG. 7C shows Combination Index (CI) plots for MIAPaCa-2 (KRAS$^{G12C}$) and PSN1 (KRAS$^{G12R}$) cells treated with Auranofin in combination with Gemcitabine. According to FIG. 7C, CI values of <1 indicated synergism between Auranofin and Gemcitabine. FIG. 7D shows Combination Index (CI) scores for MIAPaCa-2 (KRAS$^{G12C}$) and PSN1 (KRAS$^{G12R}$) cells treated with Auranofin in combination with Gemcitabine at the indicated concentrations. Each CI score represents data from at least three independent experiments.

Figure 8A:
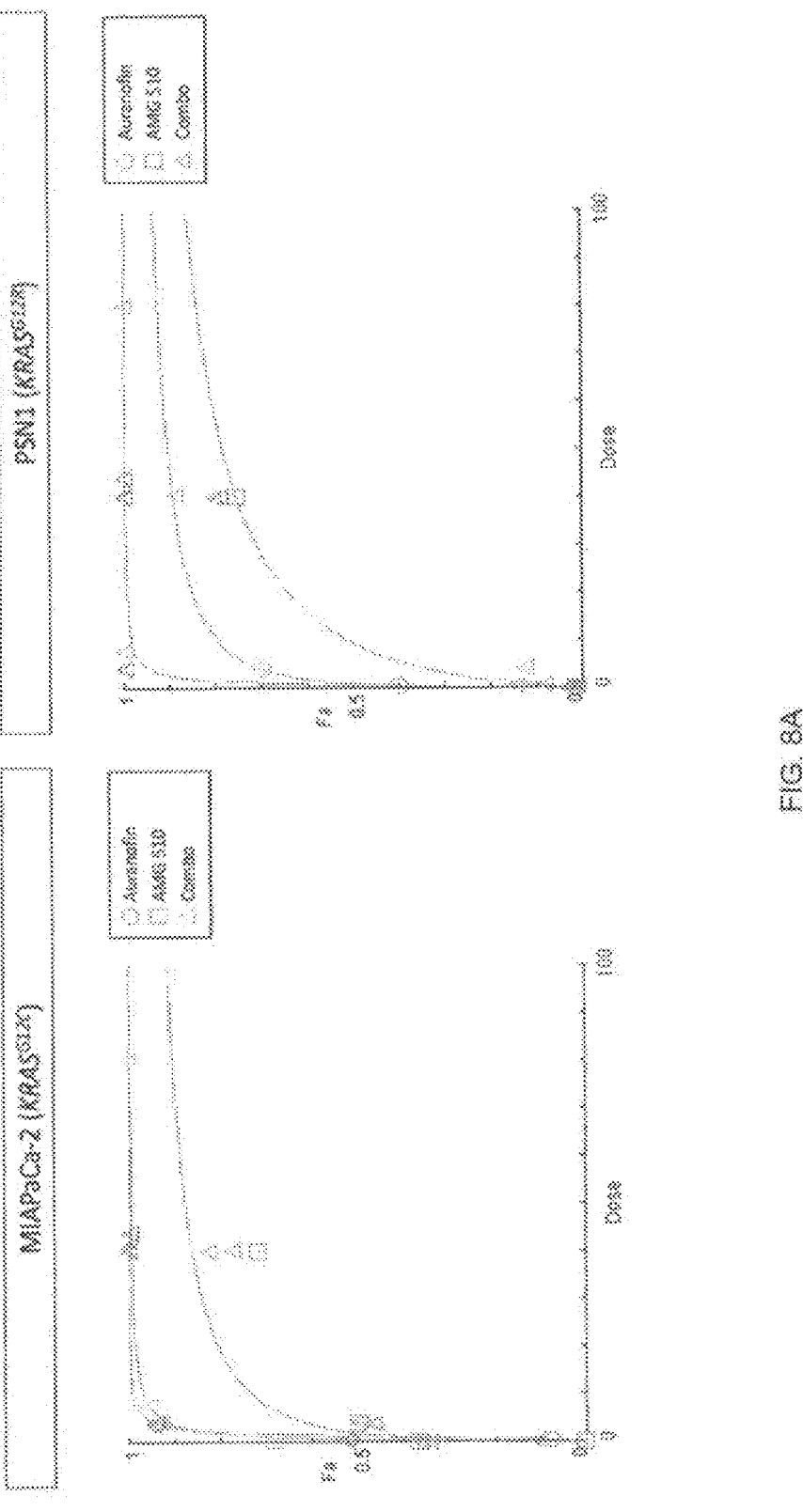
Figure 8B:
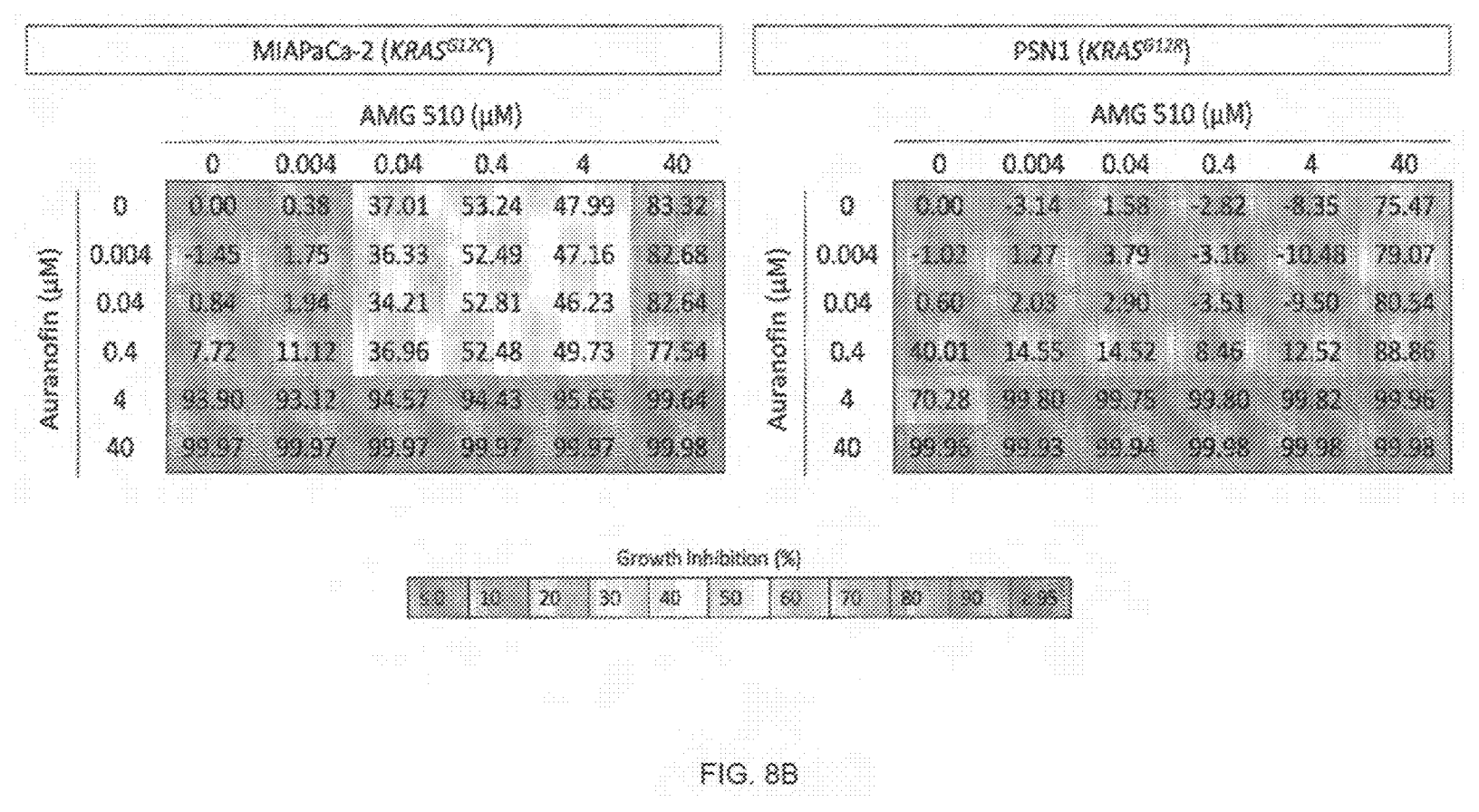
Figure 8C:
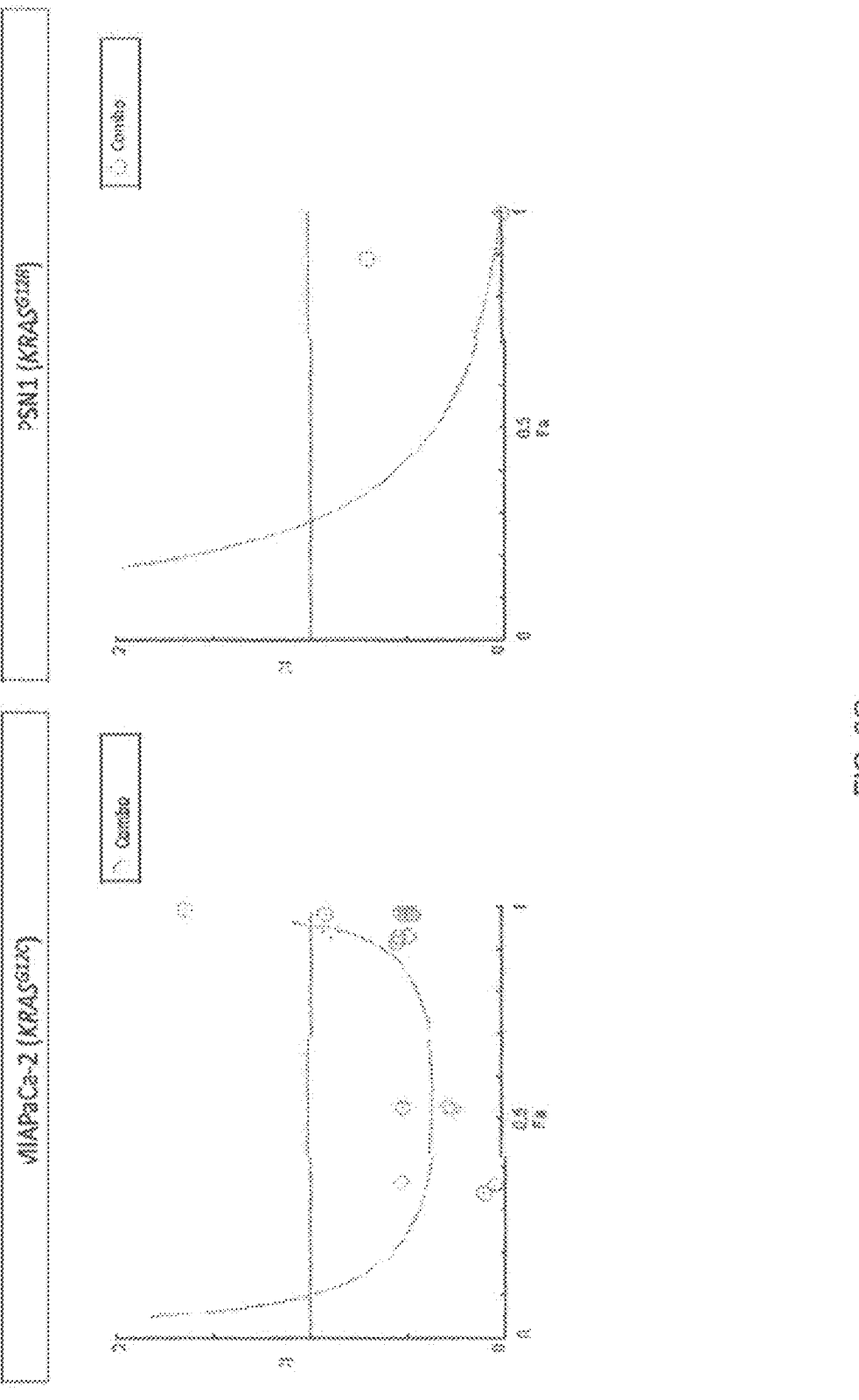
Figure 8D:
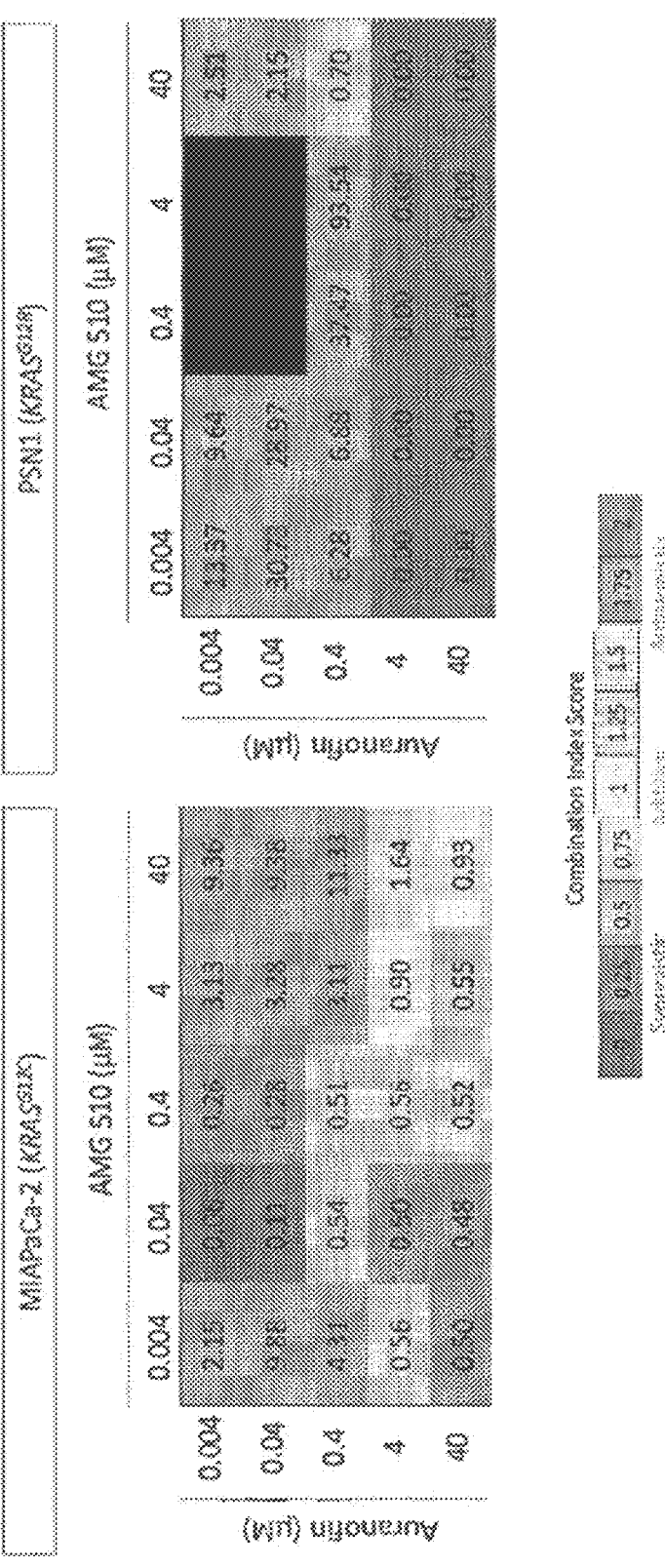

FIGS. 8A-8D show the antiproliferative effects of TXNRD1 inhibitor Auranofin in KRAS-mutant pancreatic cancer cells and potential synergistic inhibitory effects when combined with KRAS$^{G12C}$ inhibitor AMG 510. FIG. 8A shows dose-dependent effects of Auranofin, AMG 510, and their combination on MIAPaCa-2 (KRAS$^{G12C}$) and PSN1 (KRAS$^{G12R}$) pancreatic cancer cell lines. FIG. 8B shows percent growth inhibition at each concentration of Auranofin and AMG 510 in MIAPaCa-2 (KRAS$^{G12C}$) and PSN1 (KRAS$^{G12R}$) cells from FIG. 8A. Data presented as mean of three independent experiments (n=3). FIG. 8C shows CI plots presenting CI values of <1 indicated synergism between Auranofin and AMG 510. FIG. 8D shows Combination Index (CI) scores for MIAPaCa-2 (KRAS$^{G12C}$) and PSN1 (KRAS$^{G12R}$) cells treated with Auranofin in combination with AMG 510 at the indicated concentrations. Each CI score represents data from at least three independent experiments.

Figure 9:
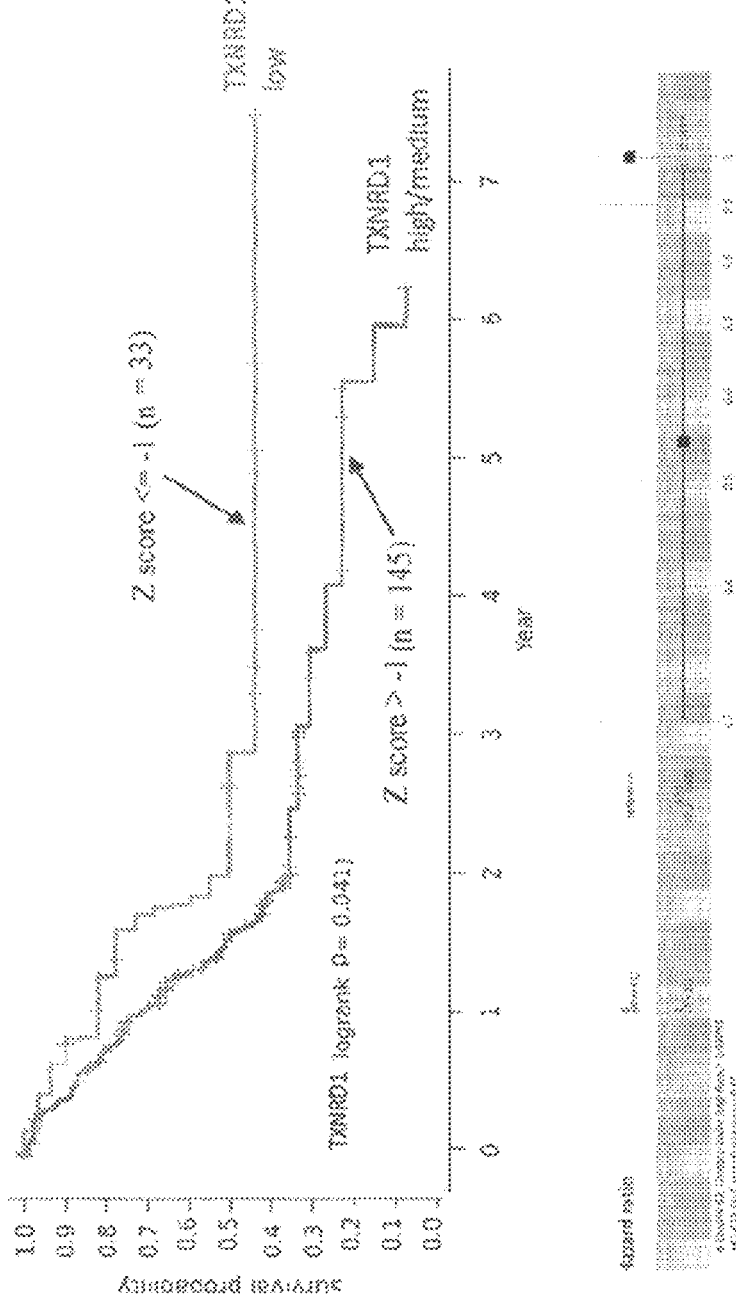

FIG. 9 shows overall survival in patients with pancreatic adenocarcinoma who have TXNRD1 mRNA upregulation. 178 patients were separated to two groups, TXNRD1 low and TXNRD1 high/medium. Proportion cutoff (0-100%) for high/medium and low is >15.87% (Z score >−1, n=145) and <=15.87% (Z score<=−1, n=33), respectively. Data analysis is based on available TCGA data.

Figure 10:
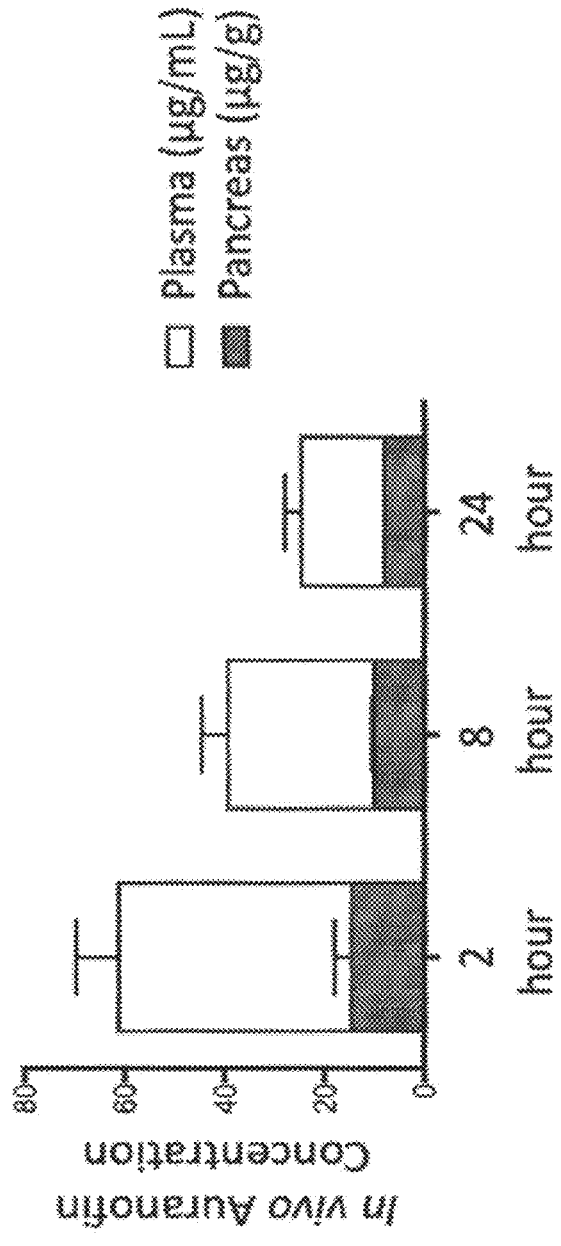

FIG. 10 shows plasma and pancreas gold concentration in NCR nu/nu mice following a single intraperitoneal injection dose of 10 mg/kg auranofin suspension. Three serial samples (2h, 4h, 24h) collected over 24 hours (n=3).

DETAILED DESCRIPTION

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, microbiology and recombinant DNA are used. See, e.g., Sambrook and Russell eds. (2001) *Molecular Cloning: A Laboratory Manual*, 3rd edition; the series Ausubel et al., eds. (2007) *Current Protocols in Molecular Biology*; the series *Methods in Enzymology* (Academic Press, Inc., N.Y.); MacPherson et al., (1991) *PCR 1: A Practical Approach* (IRL Press at Oxford University Press); MacPherson et al., (1995) PCR 2: A Practical Approach; Harlow and Lane eds. (1999) Antibodies, *A Laboratory Manual*; Freshney (2005) *Culture of Animal Cells: A Manual of Basic Technique*, 5th edition; Gait ed. (1984) Oligonucleotide Synthesis; U.S. Pat. No. 4,683,195; Hames and Higgins eds. (1984) *Nucleic Acid Hybridization; Anderson* (1999) *Nucleic Acid Hybridization; Hames and Higgins eds. (1984) Transcription and Translation; Immobilized Cells and Enzymes* (IRL Press (1986)); Perbal (1984) *A Practical Guide to Molecular Cloning*; Miller and Calos eds. (1987) *Gene Transfer Vec-*

*tors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al., eds (1996) *Weir's Handbook of Experimental Immunology*.

The present disclosure is based, in part, on the discovery that TXNRD1 is a therapeutic target for treating RAS-mutant pancreatic cancer, and that pharmacological inhibition of TXNRD1 in pancreatic cancer cells was effective in treating RAS mutant pancreatic cancer.

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. As used herein, "antibodies" (includes intact immunoglobulins) and "antigen binding fragments" specifically bind to a molecule of interest (or a group of highly similar molecules of interest) to the substantial exclusion of binding to other molecules (for example, antibodies and antibody fragments that have a binding constant for the molecule of interest that is at least $10^3$ M$^{-1}$ greater, at least $10^4$ M$^{-1}$ greater or at least $10^5$ M$^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology*, 3$^{rd}$ Ed., W.H. Freeman & Co., New York, 1997.

More particularly, antibody refers to a polypeptide ligand comprising at least a light chain immunoglobulin variable region or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Typically, an immunoglobulin has heavy (H) chains and light (L) chains interconnected by disulfide bonds. There are two types of light chain, lambda ($\lambda$) and kappa ($\kappa$). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds TXNRD1 protein will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). "Immunoglobulin-related compositions" as used herein, refers to antibodies (including monoclonal antibodies, polyclonal antibodies, humanized antibodies, chimeric antibodies, recombinant antibodies, multi-specific antibodies, bispecific antibodies, etc.,) as well as antibody fragments. An antibody or antigen binding fragment thereof specifically binds to an antigen.

As used herein, the term "antibody-related polypeptide" means antigen-binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included in the technology are any combinations of variable region(s) and hinge region, $CH_1$, $CH_2$, and $CH_3$ domains. Antibody-related molecules useful in the present methods, e.g., but are not limited to, Fab, Fab' and F(ab')$_2$, Fd, single-chain Fvs (scFv), single-chain antibodies, disulfide-linked Fvs (sdFv)

and fragments comprising either a $V_L$ or $V_H$ domain. Examples include: (i) a Fab fragment, a monovalent fragment consisting of the $V_L$, $V_H$, CL and $CH_1$ domains; (ii) a F(ab')$_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., *Nature* 341: 544-546, 1989), which consists of a $V_H$ domain; and (vi) an isolated complementarity determining region (CDR). As such "antibody fragments" or "antigen binding fragments" can comprise a portion of a full length antibody, generally the antigen binding or variable region thereof. Examples of antibody fragments or antigen binding fragments include Fab, Fab', F(ab')$_2$, and Fv fragments; diabodies; linear antibodies; single-chain antibody molecules; and multi-specific antibodies formed from antibody fragments.

The term "antigen binding fragment" refers to a fragment of the whole immunoglobulin structure which possesses a part of a polypeptide responsible for binding to antigen. Examples of the antigen binding fragment useful in the present technology include scFv, (scFv)$_2$, scFvFc, Fab, Fab' and F(ab')$_2$, but are not limited thereto.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H$ $V_L$). By using a linker that is too short to allow pairing between the two domains on the same chain, the domains are forced to pair with the complementary domains of another chain and create two antigen binding sites. Diabodies are described more fully in, e.g., EP 404,097; WO 93/11161; and Hollinger et al., *Proc. Natl. Acad. Sci. USA*, 90: 6444-6448 (1993).

As used herein, the terms "single-chain antibodies" or "single-chain Fv (scFv)" refer to an antibody fusion molecule of the two domains of the Fv fragment, $V_L$ and $V_H$. Single-chain antibody molecules may comprise a polymer with a number of individual molecules, for example, dimer, trimer or other polymers. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single-chain Fv (scFv)). Bird et al. (1988) *Science* 242:423-426 and Huston et al. (1988) *Proc. Natl. Acad Sci. USA* 85:5879-5883. Such single-chain antibodies can be prepared by recombinant techniques or enzymatic or chemical cleavage of intact antibodies.

Any of the above-noted antibody fragments are obtained using conventional techniques known to those of skill in the art, and the fragments are screened for binding specificity and neutralization activity in the same manner as are intact antibodies.

The terms "complementary" or "complementarity" as used herein with reference to polynucleotides (i.e., a sequence of nucleotides such as an oligonucleotide or a target nucleic acid) refer to the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5." Certain bases not commonly found in naturally-occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerate, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complementary sequence can also be an RNA sequence complementary to the DNA sequence or its complementary sequence, and can also be a cDNA.

As used herein, the term "consensus FR" means a framework (FR) antibody region in a consensus immunoglobulin sequence. The FR regions of an antibody do not contact the antigen.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a RAS-mutant cancer. As used herein, a "therapeutically effective amount" of a composition refers to composition levels in which the physiological effects of a disease or condition are ameliorated or eliminated. A therapeutically effective amount can be given in one or more administrations.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same nucleobase or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+ PDB+GenBank CDS translations+SwissProtein+SPupdate+ PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, the term "hypervariable region" refers to the amino acid residues of an antibody which are responsible for antigen-binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest,* 5th Ed. Public Health Service, National Institutes of Health, Bethesda, MD (1991)) and/or those residues from a "hypervariable loop" (e.g., residues 26-32 (L1), 50-52 (L2) and 91-96 (L3) in the $V_L$, and 26-32 (H1), 52A-55 (H2) and 96-101 (H3) in the $V_H$ (Chothia and Lesk *J. Mol. Biol.* 196:901-917 (1987)).

The term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropriately stringent conditions to form a duplex or heteroduplex through formation of hydrogen bonds between complementary base pairs. Nucleic acid hybridization techniques are well known in the art. See, e.g., Sambrook, et al., 1989, *Molecular Cloning: A Laboratory Manual,* Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point (Tm) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual,* Second Edition, Cold Spring Harbor Press, Plainview, N.Y.; Ausubel, F. M. et al., 1994, *Current Protocols in Molecular Biology,* John Wiley & Sons, Secaucus, N.J. In some embodiments, specific hybridization occurs under stringent hybridization conditions. An oligonucleotide or polynucleotide (e.g., a probe or a primer) that is specific for a target nucleic acid will "hybridize" to the target nucleic acid under suitable conditions.

As used herein, "oligonucleotide" refers to a molecule that has a sequence of nucleic acid bases on a backbone comprised mainly of identical monomer units at defined intervals. The bases are arranged on the backbone in such a way that they can bind with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group at the 2' position. Oligonucleotides may also include derivatives, in which the hydrogen of the hydroxyl group is replaced with organic groups, e.g., an allyl group. One or more bases of the oligonucleotide may also be modified to include a phosphorothioate bond (e.g., one of the two oxygen atoms in the phosphate backbone which is not involved in the internucleotide bridge, is replaced by a sulfur atom) to increase resistance to nuclease degradation. The exact size of the oligonucleotide will depend on many factors, which in turn depend on the ultimate function or use of the oligonucleotide. The oligonucleotide may be generated in any manner, including, for example, chemical synthesis, DNA replication, restriction endonuclease digestion of plasmids or phage DNA, reverse transcription, PCR, or a combination thereof. The oligonucleotide may be modified e.g., by addition of a methyl group, a biotin or digoxigenin moiety, a fluorescent tag or by using radioactive nucleotides.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences (20$^{th}$ edition, ed. A. Gennaro, 2000, Lippincott, Williams & *Wilkins*, Philadelphia, Pa.).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, "prevention," "prevent," or "preventing" of a disorder or condition refers to one or more compounds that, in a statistical sample, reduces the occurrence of the disorder or condition in the treated sample relative to an untreated control sample, or delays the onset of one or more symptoms of the disorder or condition relative to the untreated control sample. As used herein, preventing a RAS-mutant cancer, includes preventing or delaying the initiation of symptoms of a RAS-mutant cancer. As used herein, prevention of a RAS-mutant cancer also includes preventing a recurrence of one or more signs or symptoms of a RAS-mutant cancer.

As used herein, the term "sample" refers to clinical samples obtained from a subject. Biological samples may include tissues, cells, protein or membrane extracts of cells, mucus, sputum, bone marrow, bronchial alveolar lavage (BAL), bronchial wash (BW), and biological fluids (e.g., ascites fluid or cerebrospinal fluid (CSF)) isolated from a subject, as well as tissues, cells and fluids (blood, plasma, saliva, urine, serum etc.) present within a subject.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, the terms "subject," "individual," or "patient" are used interchangeably and refer to an individual organism, a vertebrate, a mammal, or a human. In certain embodiments, the individual, patient or subject is a human.

As used herein, the terms "target sequence" and "target nucleic acid sequence" refer to a specific nucleic acid sequence to be modulated (e.g., inhibited or downregulated).

The term "TXNRD1 inhibitor" as used herein refers to an agent that inhibits gene expression or biological activity of TXNRD1. Examples of TXNRD1 biological activity include, but are not limited to, enzymatic activity, substrate binding activity, homo- or hetero-dimerization activity, and binding to a cellular structure. Several different isoforms of thioredoxin reductase 1 exist. The TXNRD1 inhibitors of the present disclosure inhibit at least one biological activity of at least one isoform. Examples of TXNRD1 inhibitors include, but are not limited to, auranofin, Piperlongumine, D9, TRi-1, TRi-2, Myricetin, PMX464, PX12, brevetoxin-2, manumycin A, ethaselen, aurothioglucose, protoporphyrin IX, shRNAs or siRNAs against TXNRD1, anti-sense oligonucleotides against TXNRD1, anti-TXNRD1 antibodies, or any derivatives thereof.

"Treating", "treat", or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment or prevention of medical diseases and conditions as described are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.
TXNRD1 Inhibitors of the Present Technology TXNRD1 protein (also known as, thioredoxin reductase 1, GRIM-12, TR, TR1, TRXR1, or TXNR) is a member of the pyridine nucleotide oxidoreductase family, and is a component of the thioredoxin (Trx) system. TXNRD1 is a flavoenzyme, which reduces thioredoxins, as well as other substrates, and plays a key role in redox homoeostasis and selenium metabolism. TXNRD1 protein functions as a homodimer containing FAD, and has a selenocysteine (Sec) at the active site.

In one aspect, the present disclosure provides compositions for treating a RAS-mutant cancer. In some embodiments, the TXNRD1 inhibitor reduces gene expression and/or activity levels of TXNRD1. In some embodiments, the TXNRD1 inhibitor reduces a TXNRD1 activity selected from the group consisting of enzymatic activity, substrate binding activity, homo- or hetero-dimerization activity, and binding to a cellular structure.

In one aspect, the present disclosure provides pharmacological inhibitors including, but not limited to, auranofin, Piperlongumine, D9, TRi-1, TRi-2, Myricetin, PMX464, PX12, brevetoxin-2, manumycin A, ethaselen, aurothioglucose, and protoporphyrin IX. Anti-TXNRD1 antibodies or any derivatives thereof, may also be used in the methods disclosed herein.

In another aspect, the present disclosure provides inhibitory RNAs (e.g., sgRNAs, antisense RNAs or shRNAs) that inhibit TXNRD1 expression and/or activity levels. Examples of such inhibitory RNAs include those with sequences comprising TCTAATATCATTAACACCATGG (SEQ ID NO: 1; human shTXNRD1), TAAATAAAACT-GAATATGGTCA (SEQ ID NO: 2; human shTXNRD1), TTAATAATAACTTATGATATTA (SEQ ID NO: 3; human shTXNRD1), TTTGTAACAAAAATACATGGAA (SEQ ID NO: 4; human shTXNRD1), TTTAAATGAAAATCCTT-CACAT (SEQ ID NO: 5; human shTXNRD1), TTTTAAAT-GAAAATCCTTCACA (SEQ ID NO: 6; human shTXNRD1), TAAGAAAAGAGAATCACAACAT (SEQ ID NO: 7; human shTXNRD1), TTTTCATTTATCTT-CACCCCTA (SEQ ID NO: 8; human shTXNRD1), TTAGAAAGAAATAGATACCCAA (SEQ ID NO: 9; human shTXNRD1), TAATAATAACTTATGATATTAA (SEQ ID NO: 10; human shTXNRD1), TTTAGT-CACAGGGTAATTCGTC (SEQ ID NO: 11; murine shTxnrd1), and TTCGTCACTGACAACGTTGTGA (SEQ ID NO: 12; murine shTxnrd1), or any complement thereof.

The present disclosure provides an antisense nucleic acid comprising a nucleic acid sequence that is complementary to and specifically hybridizes with a portion of any one of

```
NM_182729.2 Homo sapiens thioredoxin reductase 1 (TXNRD1), transcript
variant 1, mRNA
                                                          (SEQ ID NO: 13)
     1 agaccctcac gtgatgacaa cagctagcaa agttctgtag ctactgcctt agggcatagt 61 ctaatttctt cagtaaaaac acacttattc caaatttggt tccagaattg ccttaaattg 121 tttttgctct gttcttaggt tgggggcggc tatgagcagg cagaggatgt ggtgtcaccc 181 aattaggagc tctcagctta cgaggcaatt agcataggtt gccagggctg cacgaggagt 241 ggatttctgc tttgtcattc tgactctggc agttagcccg cccgctcggc gcagggcgtg 301 gcttctcgta gccattagga aacagcaacc ctttcacctc agttttcttc actccggcat 361 ttgcagcaga gcgaaaggtg gtcgagtcct gaaggagggc ctgatgtctt catcattctc 421 aaattcttag gacggtcggg ccctggaagg aacgctctcg gaattggccg cggaaaccga 481 tctgcccgtt gtgtttgtga aacagagaaa gataggcggc catggtccaa ccttgaaggc 541 ttatcaggag ggcagacttc aaaagctact aaaaatgaac ggccctgaag atcttcccaa 601 gtcctatgac tatgacctta tcatcattgg aggtggctca ggaggtctgg cagctgctaa 661 ggaggcagcc caatatggca agaaggtgat ggtcctggac tttgtcactc ccacccctct 721 tggaactaga tggggtctcg gaggaacatg tgtgaatgtg ggttgcatac ctaaaaaact 781 gatgcatcaa gcagctttgt taggacaagc cctgcaagac tctcgaaatt atggatggaa 841 agtcgaggag acagttaagc atgattggga cagaatgata gaagctgtac agaatcacat 901 tggctctttg aattggggct accgagtagc tctgcgggag aaaaaagtcg tctatgagaa 961 tgcttatggg caatttattg gtcctcacag gattaaggca acaaataata aaggcaaaga 1021 aaaaatttat tcagcagaga gatttctcat tgccactggt gaaagaccac gttacttggg 1081 catccctggt gacaaagaat actgcatcag cagtgatgat cttttctcct tgccttactg 1141 cccgggtaag accctggttg ttggagcatc ctatgtcgct ttggagtgcg ctggatttct 1201 tgctggtatt ggtttagacg tcactgttat ggttaggtcc attcttctta gaggatttga 1261 ccaggacatg gccaacaaaa ttggtgaaca catggaagaa catggcatca agtttataag
```

-continued

```
1321 acagttcgta ccaattaaag ttgaacaaat tgaagcaggg acaccaggcc gactcagagt 1381 agtagctcag tccaccaata gtgaggaaat cattgaagga gaatataata cggtgatgct 1441 ggcaatagga agagatgctt gcacaagaaa aattggctta gaaaccgtag gggtgaagat 1501 aaatgaaaag actggaaaaa tacctgtcac agatgaagaa cagaccaatg tgccttacat 1561 ctatgccatt ggcgatatat tggaggataa ggtggagctc accccagttg caatccaggc 1621 aggaagattg ctggctcaga ggctctatgc aggttccact gtcaagtgtg actatgaaaa 1681 tgttccaacc actgtattta ctcctttgga atatggtgct tgtggccttt ctgaggagaa 1741 agctgtggag aagtttgggg aagaaaatat tgaggtttac catagttact tttggccatt 1801 ggaatggacg attccgtcaa gagataacaa caaatgttat gcaaaaataa tctgtaatac 1861 taaagacaat gaacgtgttg tgggctttca cgtactgggt ccaaatgctg gagaagttac 1921 acaaggcttt gcagctgcgc tcaaatgtgg actgaccaaa aagcagctgg acagcacaat 1981 tggaatccac cctgtctgtg cagaggtatt cacaacattg tctgtgacca agcgctctgg 2041 ggcaagcatc ctccaggctg gctgctgagg ttaagcccca gtgtggatgc tgttgccaag 2101 actgcaaacc actggctcgt ttccgtgccc aaatccaagg cgaagttttc tagagggttc 2161 ttgggctctt ggcacctgcg tgtcctgtgc ttaccaccgc ccaaggcccc cttggatctc 2221 ttggatagga gttggtgaat agaaggcagg cagcatcaca ctggggtcac tgacagactt 2281 gaagctgaca tttggcaggg catcgaaggg atgcatccat gaagtcacca gtctcaagcc 2341 catgtggtag gcggtgatgg aacaactgtc aaatcagttt tagcatgacc tttccttgtg 2401 gattttctta ttctcgttgt caagttttct agggttgaat ttttttcttt tttctccatg 2461 gtgttaatga tattagagat gaaaaacgtt agcagttgat ttttgtccaa aagcaagtca 2521 tggctagagt atccatgcaa ggtgtcttgt tgcatggaag ggatagtttg gctcccttgg 2581 aggctatgta ggcttgtccc gggaaagaga actgtcctgc agctgaaatg gactgttctt 2641 tactgacctg ctcagcagtt tcttctctca tatattccca aaacaagtac atctgcgatc 2701 aactctagcc aaatttgccc ctgtgtgcta catgatggat gattattatt ttaaggtctg 2761 tttaggaagg gaaatggcta cttggccagc cattgcctgg catttggtag tatagtatga 2821 ttctcaccat tatttgtcat ggaggcagac atacaccaga aatgggggag aaacagtaca 2881 tatctttctg tctttagttt attgtgtgct ggtctaagca agctgagatc atttgcaatg 2941 gaaaacacgt aacttgttta aaagtttttc tggtagcttt agctttatgc taaaaaaaat 3001 aatgacattg ggtatctatt tctttctaag actacattag taggaaaata agtcttttca 3061 tgcttatgat ttagctgttt tgtggtaatt gctttttaaa ggaagttatt aatatcataa 3121 gttattatta atattttgaa cacaggtgga tgtgaaggat tttcatttaa aaaccaagtg 3181 gttttgactt tttctgttga atgaacaact gtgccttgtg gaattttttgc agaagtgttt 3241 atgctttgtt agcatttcaa cttgcattat tataaagagg tattaatgcc tcagttatgt 3301 gtttgtcaat gtactggctg aggattctat ctcagctgtc ttttctaact gtgtaggttg 3361 agttttgaac acgtgcttgt ggacatcagg cctcctgcca gcagttcttg aagcttcttt 3421 ttcattcctg ctactctacc tgtatttctc agttgcagca ctgagtggtc aaaatacatt 3481 tctgggccac ctcagggaac ccatgcatct gcctggcatt taggcagcag agcccctgac 3541 cgtcccccac agggctctgc ctcacgtcct catctcattt ggctgtgtaa agaaatggga 3601 aaagggaaaa ggagagagca attgaggcag ttgaccatat tcagttttat ttatttattt 3661 ttaatttgtt tttttctcca agtccaccag tctctgaaat tagaacagta ggcggtatga 3721 gataatcagg cctaatcatg ttgtgattct cttttcttag tggagtggaa tgttctatcc
```

-continued

```
3781 ccacaagaag gattatatct tatagacttg tcttgttcag attctgtatt tacccatttt 3841 attgaaacat atactaagtt ccatgtattt ttgttacaaa tcttctgaaa aaaaacaaaa 3901 caatgtgaaa cattaaaatt aaaaggcatt aataatatcc acgtgtgcct tcttactgaa 3961 aaaaaaaaa
```

NM_182742.2 *Homo sapiens* thioredoxin reductase 1 (TXNRD1), transcript
variant 2, mRNA (SEQ ID NO: 14)

```
   1 agaccctcac gtgatgacaa cagctagcaa agttctgtag ctactgcctt agggcatagt 61 ctaatttctt cagtaaaaac acacttattc caaatttggt tccagaattg ccttaaattg 121 tttttgctct gttcttaggt tgggggcggc tatgagcagg cagaggatgt ggtgtcaccc 181 aattaggagc tctcagctta cgaggcaatt agcataggtt gccagggctg cacgaggagt 241 ggatttctgc tttgtcattc tgactctggc agttagcccg cccgctcggc gcagggcgtg 301 gcttctcgta gccattagga aacagcaacc ctttcacctc agttttcttc actccggcat 361 ttgcagcaga gcgaaaggtg gtcgagtcct gaaggagggc ctgatgtctt catcattctc 421 aaattcttgt aagctctgcg tcgggtgaaa ccagacaaag ccgcgagccc agggatggga 481 gcacgcgggg gacggcctgc cggcggggac gacagcattg cgcctgggtg cagcagtgtg 541 cgtctcgggg aagggaagat attttaaggc gtgtctgagc agacggggag gcttttccaa 601 acccaggcag cttcgtggcg tgtgcggttt cgacccggtc acacaaagct tcagcatgtc 661 atgtggctta tcaggagggc agacttcaaa agctactaaa aatgaacggc cctgaagatc 721 ttcccaagtc ctatgactat gaccttatca tcattggagg tggctcagga ggtctggcag 781 ctgctaagga ggcagcccaa tatggcaaga aggtgatggt cctggacttt gtcactccca 841 cccctcttgg aactagatgg ggtctcggag aacatgtgt gaatgtgggt tgcataccta 901 aaaaactgat gcatcaagca gctttgttag acaagccct gcaagactct cgaaattatg 961 gatggaaagt cgaggagaca gttaagcatg attgggacag aatgatagaa gctgtacaga 1021 atcacattgg ctctttgaat tggggctacc gagtagctct gcgggagaaa aaagtcgtct 1081 atgagaatgc ttatgggcaa tttattggtc ctcacaggat taaggcaaca aataataaag 1141 gcaaagaaaa aatttattca gcagagagat ttctcattgc cactggtgaa agaccacgtt 1201 acttgggcat ccctggtgac aaagaatact gcatcagcag tgatgatctt ttctccttgc 1261 cttactgccc gggtaagacc ctggttgttg gagcatccta tgtcgctttg gagtgcgctg 1321 gatttcttgc tggtattggt ttagacgtca ctgttatggt taggtccatt cttcttagag 1381 gatttgacca ggacatggcc aacaaaattg gtgaacacat ggaagaacat ggcatcaagt 1441 ttataagaca gttcgtacca attaaagttg aacaaattga agcagggaca ccaggccgac 1501 tcagagtagt agctcagtcc accaatagtg aggaaatcat tgaaggagaa tataatacgg 1561 tgatgctggc aataggaaga gatgcttgca caagaaaaat tggcttagaa accgtagggg 1621 tgaagataaa tgaaaagact ggaaaaatac ctgtcacaga tgaagaacag accaatgtgc 1681 cttacatcta tgccattggc gatatattgg aggataaggt ggagctcacc ccagttgcaa 1741 tccaggcagg aagattgctg gctcagaggc tctatgcagg ttccactgtc aagtgtgact 1801 atgaaaatgt tccaaccact gtatttactc ctttggaata tggtgcttgt ggcctttctg 1861 aggagaaagc tgtggagaag tttgggggaag aaaatattga ggtttaccat agttactttt 1921 ggccattgga atggacgatt ccgtcaagag ataacaacaa atgttatgca aaaataatct 1981 gtaatactaa agacaatgaa cgtgttgtgg gctttcacgt actgggtcca aatgctggag 2041 aagttacaca aggctttgca gctgcgctca aatgtggact gaccaaaaag cagctggaca

```

-continued

```
2101 gcacaattgg aatccaccct gtctgtgcag aggtattcac aacattgtct gtgaccaagc 2161 gctctggggc aagcatcctc caggctggct gctgaggtta agccccagtg tggatgctgt 2221 tgccaagact gcaaaccact ggctcgtttc cgtgcccaaa tccaaggcga agttttctag 2281 agggttcttg ggctcttggc acctgcgtgt cctgtgctta ccaccgccca aggccccctt 2341 ggatctcttg gataggagtt ggtgaataga aggcaggcag catcacactg gggtcactga 2401 cagacttgaa gctgacattt ggcagggcat cgaagggatg catccatgaa gtcaccagtc 2461 tcaagcccat gtggtaggcg gtgatggaac aactgtcaaa tcagttttag catgaccttt 2521 ccttgtggat tttcttattc tcgttgtcaa gttttctagg gttgaatttt tttctttttt 2581 ctccatggtg ttaatgatat tagagatgaa aaacgttagc agttgatttt tgtccaaaag 2641 caagtcatgg ctagagtatc catgcaaggt gtcttgttgc atggaaggga tagtttggct 2701 cccttggagg ctatgtaggc ttgtcccggg aaagagaact gtcctgcagc tgaaatggac 2761 tgttctttac tgacctgctc agcagtttct tctctcatat attcccaaaa caagtacatc 2821 tgcgatcaac tctagccaaa tttgcccctg tgtgctacat gatggatgat tattatttta 2881 aggtctgttt aggaagggaa atggctactt ggccagccat tgcctggcat ttggtagtat 2941 agtatgattc tcaccattat ttgtcatgga ggcagacata caccagaaat gggggagaaa 3001 cagtacatat ctttctgtct ttagtttatt gtgtgctggt ctaagcaagc tgagatcatt 3061 tgcaatggaa aacacgtaac ttgtttaaaa gttttttctgg tagctttagc tttatgctaa 3121 aaaaaataat gacattgggt atctatttct ttctaagact acattagtag gaaaataagt 3181 cttttcatgc ttatgattta gctgttttgt ggtaattgct ttttaaagga agttattaat 3241 atcataagtt attattaata ttttgaacac aggtggatgt gaaggatttt catttaaaaa 3301 ccaagtggtt ttgacttttt ctgttgaatg aacaactgtg ccttgtggaa tttttgcaga 3361 agtgtttatg ctttgttagc atttcaactt gcattattat aaagaggtat taatgcctca 3421 gttatgtgtt tgtcaatgta ctggctgagg attctatctc agctgtcttt tctaactgtg 3481 taggttgagt tttgaacacg tgcttgtgga catcaggcct cctgccagca gttcttgaag 3541 cttcttttc attcctgcta ctctacctgt atttctcagt tgcagcactg agtggtcaaa 3601 atacatttct gggccacctc agggaaccca tgcatctgcc tggcatttag gcagcagagc 3661 ccctgaccgt cccccacagg gctctgcctc acgtcctcat ctcatttggc tgtgtaaaga 3721 aatgggaaaa gggaaaagga gagagcaatt gaggcagttg accatattca gttttattta 3781 tttattttta atttgttttt ttctccaagt ccaccagtct ctgaaattag aacagtaggc 3841 ggtatgagat aatcaggcct aatcatgttg tgattctctt ttcttagtgg agtggaatgt 3901 tctatcccca caagaaggat tatatcttat agacttgtct tgttcagatt ctgtatttac 3961 ccattttatt gaaacatata ctaagttcca tgtattttttg ttacaaatct tctgaaaaaa 4021 aacaaaacaa tgtgaaacat taaaattaaa aggcattaat aatatccacg tgtgccttct 4081 tactgaaaaa aaaaaa
```

*Homo sapiens* thioredoxin reductase 1 (TXNRD1), transcript variant 3, mRNA
NCBI Reference Sequence: NM_182743.2

(SEQ ID NO: 15)

```
   1 agaccctcac gtgatgacaa cagctagcaa agttctgtag ctactgcctt agggcatagt 61 ctaatttctt cagtaaaaac acacttattc caaatttggt tccagaattg ccttaaattg 121 tttttgctct gttcttaggt tggggggcggc tatgagcagg cagaggatgt ggtgtcaccc 181 aattaggagc tctcagctta cgaggcaatt agcataggtt gccagggctg cacgaggagt 241 ggatttctgc tttgtcattc tgactctggc agttagcccg cccgctcggc gcagggcgtg
```

-continued

```
 301 gcttctcgta gccattagga aacagcaacc ctttcacctc agttttcttc actccggcat 361 ttgcagcaga gcgaaaggtg gtcgagtcct gaaggagggc ctgatgtctt catcattctc 421 aaattcttgc ttatcaggag ggcagacttc aaaagctact aaaaatgaac ggccctgaag 481 atcttcccaa gtcctatgac tatgacctta tcatcattgg aggtggctca ggaggtctgg 541 cagctgctaa ggaggcagcc caatatggca agaaggtgat ggtcctggac tttgtcactc 601 ccacccctct tggaactaga tggggtctcg gaggaacatg tgtgaatgtg ggttgcatac 661 ctaaaaaact gatgcatcaa gcagctttgt taggacaagc cctgcaagac tctcgaaatt 721 atggatggaa agtcgaggag acagttaagc atgattggga cagaatgata gaagctgtac 781 agaatcacat tggctctttg aattggggct accgagtagc tctgcgggag aaaaaagtcg 841 tctatgagaa tgcttatggg caatttattg gtcctcacag gattaaggca acaaataata 901 aaggcaaaga aaaaatttat tcagcagaga gatttctcat tgccactggt gaaagaccac 961 gttacttggg catccctggt gacaaagaat actgcatcag cagtgatgat cttttctcct 1021 tgccttactg cccgggtaag accctggttg ttggagcatc ctatgtcgct ttggagtgcg 1081 ctggatttct tgctggtatt ggtttagacg tcactgttat ggttaggtcc attcttctta 1141 gaggatttga ccaggacatg gccaacaaaa ttggtgaaca catggaagaa catggcatca 1201 agtttataag acagttcgta ccaattaaag ttgaacaaat tgaagcaggg acaccaggcc 1261 gactcagagt agtagctcag tccaccaata gtgaggaaat cattgaagga gaatataata 1321 cggtgatgct ggcaatagga agagatgctt gcacaagaaa aattggctta gaaaccgtag 1381 gggtgaagat aaatgaaaag actggaaaaa tacctgtcac agatgaagaa cagaccaatg 1441 tgccttacat ctatgccatt ggcgatatat ggaggataaa ggtggagctc accccagttg 1501 caatccaggc aggaagattg ctggctcaga ggctctatgc aggttccact gtcaagtgtg 1561 actatgaaaa tgttccaacc actgtattta ctcctttgga atatggtgct tgtggccttt 1621 ctgaggagaa agctgtggag aagtttgggg aagaaaatat tgaggtttac catagttact 1681 tttggccatt ggaatggaca attccgtcaa gagataacaa caaatgttat gcaaaaataa 1741 tctgtaatac taaagacaat gaacgtgttg tgggctttca cgtactgggt ccaaatgctg 1801 gagaagttac acaaggcttt gcagctgcgc tcaaatgtgg actgaccaaa aagcagctgg 1861 acagcacaat tggaatccac cctgtctgtg cagaggtatt cacaacattg tctgtgacca 1921 agcgctctgg ggcaagcatc ctccaggctg ctgctgagg ttaagcccca gtgtggatgc 1981 tgttgccaag actgcaaacc actggctcgt ttccgtgccc aaatccaagg cgaagttttc 2041 tagagggttc ttgggctctt ggcacctgcg tgtcctgtgc ttaccaccgc ccaaggcccc 2101 cttggatctc ttggatagga gttggtgaat agaaggcagg cagcatcaca ctggggtcac 2161 tgacagactt gaagctgaca tttggcaggg catcgaaggg atgcatccat gaagtcacca 2221 gtctcaagcc catgtggtag gcggtgatgg aacaactgtc aaatcagttt tagcatgacc 2281 tttccttgtg gattttctta ttctcgttgt caagttttct agggttgaat ttttttcttt 2341 tttctccatg gtgttaatga tattagagat gaaaaacgtt agcagttgat ttttgtccaa 2401 aagcaagtca tggctagagt atccatgcaa ggtgtcttgt tgcatggaag ggatagtttg 2461 gctcccttgg aggctatgta ggcttgtccc gggaaagaga actgtcctgc agctgaaatg 2521 gactgttctt tactgacctg ctcagcagtt tcttctctca tatattccca aaacaagtac 2581 atctgcgatc aactctagcc aaatttgccc ctgtgtgcta catgatggat gattattatt 2641 ttaaggtctg tttaggaagg gaaatggcta cttggccagc cattgcctgg catttggtag
```

-continued

```
2701 tatagtatga ttctcaccat tatttgtcat ggaggcagac atacaccaga aatgggggag 2761 aaacagtaca tatctttctg tctttagttt attgtgtgct ggtctaagca agctgagatc 2821 atttgcaatg gaaaacacgt aacttgttta aaagtttttc tggtagcttt agctttatgc 2881 taaaaaaaat aatgacattg ggtatctatt tctttctaag actacattag taggaaaata 2941 agtcttttca tgcttatgat ttagctgttt tgtggtaatt gctttttaaa ggaagttatt 3001 aatatcataa gttattatta atattttgaa cacaggtgga tgtgaaggat tttcatttaa 3061 aaaccaagtg gttttgactt tttctgttga atgaacaact gtgccttgtg gaatttttgc 3121 agaagtgttt atgctttgtt agcatttcaa cttgcattat tataaagagg tattaatgcc 3181 tcagttatgt gtttgtcaat gtactggctg aggattctat ctcagctgtc ttttctaact 3241 gtgtaggttg agttttgaac acgtgcttgt ggacatcagg cctcctgcca gcagttcttg 3301 aagcttcttt ttcattcctg ctactctacc tgtatttctc agttgcagca ctgagtggtc 3361 aaaatacatt tctgggccac ctcagggaac ccatgcatct gcctggcatt taggcagcag 3421 agcccctgac cgtcccccac agggctctgc ctcacgtcct catctcattt ggctgtgtaa 3481 agaaatggga aaagggaaaa ggagagagca attgaggcag ttgaccatat tcagttttat 3541 ttatttattt ttaatttgtt tttttctcca agtccaccag tctctgaaat tagaacagta 3601 ggcggtatga gataatcagg cctaatcatg ttgtgattct cttttcttag tggagtggaa 3661 tgttctatcc ccacaagaag gattatatct tatagacttg tcttgttcag attctgtatt 3721 tacccatttt attgaaacat atactaagtt ccatgtattt ttgttacaaa tcttctgaaa 3781 aaaaacaaaa caatgtgaaa cattaaaatt aaaaggcatt aataatatcc acgtgtgcct 3841 tcttactgaa aaaaaaaaa
```

*Homo sapiens* thioredoxin reductase 1 (TXNRD1), transcript variant 4, mRNA
NCBI Reference Sequence: NM_003330.3

(SEQ ID NO: 16)

```
   1 agaccctcac gtgatgacaa cagctagcaa agttctgtag ctactgcctt agggcatagt 61 ctaatttctt cagtaaaaac acacttattc caaatttggt tccagaattg ccttaaattg 121 tttttgctct gttcttaggt tgggggcggc tatgagcagg cagaggatgt ggtgtcaccc 181 aattaggagc tctcagctta cgaggcaatt agcataggtt gccagggctg cacgaggagt 241 ggatttctgc tttgtcattc tgactctggc agttagcccg cccgctcggc gcagggcgtg 301 gcttctcgta gccattagga aacagcaacc ctttcacctc agttttcttc actccggcat 361 ttgcagcaga gcgaaaggtg gtcgagtcct gaaggagggc ctgatgtctt catcattctc 421 aaattcttgt aagctctgcg tcgggtgaaa ccagacaaag ccgcgagccc agggatggga 481 gcacgcgggg gacggcctgc cggcggggac gacagcattg cgcctgggtg cagcagtgtg 541 cgtctcgggg aagggaagat attttaaggc gtgtctgagc agacggggag gcttttccaa 601 acccaggcag cttcgtggcg tgtgcggttt cgacccggtc acacaaagct tcagcatgtc 661 atgtgaggac ggtcgggccc tggaaggaac gctctcggaa ttggccgcgg aaaccgatct 721 gcccgttgtg tttgtgaaac agagaaagat aggcggccat ggtccaacct tgaaggctta 781 tcaggagggc agacttcaaa agctactaaa aatgaacggc cctgaagatc ttcccaagtc 841 ctatgactat gaccttatca tcattggagg tggctcagga ggtctggcag ctgctaagga 901 ggcagcccaa tatggcaaga aggtgatggt cctggacttt gtcactccca cccctcttgg 961 aactagatgg ggtctcggag gaacatgtgt gaatgtgggt tgcataccta aaaaactgat 1021 gcatcaagca gctttgttag acaagccct gcaagactct cgaaattatg gatggaaagt 1081 cgaggagaca gttaagcatg attgggacag aatgatagaa gctgtacaga atcacattgg
```

```
1141 ctctttgaat tggggctacc gagtagctct gcgggagaaa aaagtcgtct atgagaatgc 1201 ttatgggcaa tttattggtc ctcacaggat taaggcaaca aataataaag gcaaagaaaa 1261 aatttattca gcagagagat ttctcattgc cactggtgaa agaccacgtt acttgggcat 1321 ccctggtgac aaagaatact gcatcagcag tgatgatctt ttctccttgc cttactgccc 1381 gggtaagacc ctggttgttg gagcatccta tgtcgctttg gagtgcgctg atttcttgc 1441 tggtattggt ttagacgtca ctgttatggt taggtccatt cttcttagag gatttgacca 1501 ggacatggcc aacaaaattg gtgaacacat ggaagaacat ggcatcaagt ttataagaca 1561 gttcgtacca attaaagttg aacaaattga agcagggaca ccaggccgac tcagagtagt 1621 agctcagtcc accaatagtg aggaaatcat tgaaggagaa tataatacgg tgatgctggc 1681 aataggaaga gatgcttgca caagaaaaat tggcttagaa accgtagggg tgaagataaa 1741 tgaaaagact ggaaaaatac ctgtcacaga tgaagaacag accaatgtgc cttacatcta 1801 tgccattggc gatatattgg aggataaggt ggagctcacc ccagttgcaa tccaggcagg 1861 aagattgctg gctcagaggc tctatgcagg ttccactgtc aagtgtgact atgaaaatgt 1921 tccaaccact gtatttactc ctttggaata tggtgcttgt ggcctttctg aggagaaagc 1981 tgtggagaag tttgggggaag aaaatattga ggtttaccat agttactttt ggccattgga 2041 atggacgatt ccgtcaagag ataacaacaa atgttatgca aaaataatct gtaatactaa 2101 agacaatgaa cgtgttgtgg gctttcacgt actgggtcca aatgctggag aagttacaca 2161 aggctttgca gctgcgctca aatgtggact gaccaaaaag cagctggaca gcacaattgg 2221 aatccaccct gtctgtgcag aggtattcac aacattgtct gtgaccaagc gctctggggc 2281 aagcatcctc caggctggct gctgaggtta agccccagtg tggatgctgt tgccaagact 2341 gcaaaccact ggctcgtttc cgtgcccaaa tccaaggcga gtttttctag agggttcttg 2401 ggctcttggc acctgcgtgt cctgtgctta ccaccgccca aggcccctt ggatctcttg 2461 gataggagtt ggtgaataga aggcaggcag catcacactg gggtcactga cagacttgaa 2521 gctgacattt ggcagggcat cgaagggatg catccatgaa gtcaccagtc tcaagcccat 2581 gtggtaggcg gtgatggaac aactgtcaaa tcagttttag catgaccttt ccttgtggat 2641 tttcttattc tcgttgtcaa gttttctagg gttgaatttt tttctttttt ctccatggtg 2701 ttaatgatat tagagatgaa aaacgttagc agttgatttt tgtccaaaag caagtcatgg 2761 ctagagtatc catgcaaggt gtcttgttgc atggaaggga tagtttggct cccttggagg 2821 ctatgtaggc ttgtcccggg aaagagaact gtcctgcagc tgaaatggac tgttctttac 2881 tgacctgctc agcagtttct tctctcatat attcccaaaa caagtacatc tgcgatcaac 2941 tctagccaaa tttgcccctg tgtgctacat gatggatgat tattatttta aggtctgttt 3001 aggaagggaa atggctactt ggccagccat tgcctggcat ttggtagtat agtatgattc 3061 tcaccattat ttgtcatgga ggcagacata caccagaaat gggggagaaa cagtacatat 3121 ctttctgtct ttagtttatt gtgtgctggt ctaagcaagc tgagatcatt tgcaatggaa 3181 aacacgtaac ttgtttaaaa gtttttctgg tagctttagc tttatgctaa aaaaaataat 3241 gacattgggt atctatttct ttctaagact acattagtag gaaaataagt cttttcatgc 3301 ttatgattta gctgttttgt ggtaattgct ttttaaagga agttattaat atcataagtt 3361 attattaata ttttgaacac aggtggatgt gaaggatttt catttaaaaa ccaagtggtt 3421 ttgacttttt ctgttgaatg aacaactgtg ccttgtggaa tttttgcaga agtgtttatg 3481 ctttgttagc atttcaactt gcattattat aaagaggtat taatgcctca gttatgtgtt 3541 tgtcaatgta ctggctgagg attctatctc agctgtcttt tctaactgtg taggttgagt
```

-continued

```
3601 tttgaacacg tgcttgtgga catcaggcct cctgccagca gttcttgaag cttctttttc 3661 attcctgcta ctctacctgt atttctcagt tgcagcactg agtggtcaaa atacatttct 3721 gggccacctc agggaaccca tgcatctgcc tggcatttag gcagcagagc ccctgaccgt 3781 cccccacagg gctctgcctc acgtcctcat ctcatttggc tgtgtaaaga aatgggaaaa 3841 gggaaaagga gagagcaatt gaggcagttg accatattca gttttatta ttattttta 3901 atttgttttt ttctccaagt ccaccagtct ctgaaattag aacagtaggc ggtatgagat 3961 aatcaggcct aatcatgttg tgattctctt ttcttagtgg agtggaatgt tctatcccca 4021 caagaaggat tatatcttat agacttgtct tgttcagatt ctgtatttac ccattttatt 4081 gaaacatata ctaagttcca tgtatttttg ttacaaatct tctgaaaaaa aacaaaacaa 4141 tgtgaaacat taaaattaaa aggcattaat aatatccacg tgtgccttct tactgaaaaa 4201 aaaaaa
```

Homo sapiens thioredoxin reductase 1 (TXNRD1), transcript variant 5, mRNA
NCBI Reference Sequence: NM_001261445.1

(SEQ ID NO: 17)

```
   1 agaccctcac gtgatgacaa cagctagcaa agttctgtag ctactgcctt agggcatagt 61 ctaatttctt cagtaaaaac acacttattc caaatttggt tccagaattg ccttaaattg 121 tttttgctct gttcttaggt tgggggcggc tatgagcagg cagaggatgt ggtgtcaccc 181 aattaggagc tctcagctta cgaggcaatt agcataggtt gccagggctg cacgaggagt 241 ggatttctgc tttgtcattc tgactctggc agttagcccg cccgctcggc gcagggcgtg 301 gcttctcgta gccattagga aacagcaacc ctttcacctc agttttcttc actccggcat 361 ttgcagcaga gcgaaaggtg gtcgagtcct gaaggagggc ctgatgtctt catcattctc 421 aaattcttgt aagctctgcg tcgggtgaaa ccagacaaag ccgcgagccc agggatggga 481 gcacgcgggg gacggcctgc cggcggggac gacagcattg cgcctgggtg cagcagtgtg 541 cgtctcgggg aagggaagat attttaaggc gtgtctgagc agacggggag gcttttccaa 601 acccaggcag cttcgtggcg tgtgcggttt cgacccggtc acacaaagct tcagcatgtc 661 atgtggtagg tgaggccggc gcctgtaggc tggcggtttc cttcctcttg gtctttgtag 721 agacagtttg cagaacagcg gagaaaatgg aggacggtcg ggccctggaa ggaacgctct 781 cggaattggc cgcggaaacc gatctgcccg ttgtgtttgt gaaacagaga aagataggcg 841 gccatggtcc aaccttgaag gcttatcagg agggcagact tcaaaagcta ctaaaaatga 901 acggccctga agatcttccc aagtcctatg actatgacct tatcatcatt ggaggtggct 961 caggaggtct ggcagctgct aaggaggcag cccaatatgg caagaaggtg atggtcctgg 1021 actttgtcac tcccacccct cttggaacta gatggggtct cggaggaaca tgtgtgaatg 1081 tgggttgcat acctaaaaaa ctgatgcatc aagcagcttt gttaggacaa gccctgcaag 1141 actctcgaaa ttatggatgg aaagtcgagg agacagttaa gcatgattgg gacagaatga 1201 tagaagctgt acagaatcac attggctctt tgaattgggg ctaccgagta gctctgcggg 1261 agaaaaaagt cgtctatgag aatgcttatg gcaatttat ggtcctcac aggattaagg 1321 caacaaataa taaaggcaaa gaaaaaattt attcagcaga gagatttctc attgccactg 1381 gtgaaagacc acgttacttg ggcatccctg gtgacaaaga atactgcatc agcagtgatg 1441 atctttttctc cttgccttac tgcccgggta gaccctggt tgttggagca tcctatgtcg 1501 ctttggagtg cgctggattt cttgctggta ttggtttaga cgtcactgtt atggttaggt 1561 ccattcttct tagaggattt gaccaggaca tggccaacaa aattggtgaa cacatggaag 1621 aacatggcat caagtttata agacagttcg taccaattaa agttgaacaa attgaagcag
```

-continued

```
1681 ggacaccagg ccgactcaga gtagtagctc agtccaccaa tagtgaggaa atcattgaag 1741 gagaatataa tacggtgatg ctggcaatag gaagagatgc ttgcacaaga aaaattggct 1801 tagaaaccgt aggggtgaag ataaatgaaa agactggaaa aatacctgtc acagatgaag 1861 aacagaccaa tgtgccttac atctatgcca ttggcgatat attggaggat aaggtggagc 1921 tcaccccagt tgcaatccag gcaggaagat tgctggctca gaggctctat gcaggttcca 1981 ctgtcaagtg tgactatgaa aatgttccaa ccactgtatt tactcctttg gaatatggtg 2041 cttgtggcct ttctgaggag aaagctgtgg agaagtttgg ggaagaaaat attgaggttt 2101 accatagtta cttttggcca ttggaatgga cgattccgtc aagagataac aacaaatgtt 2161 atgcaaaaat aatctgtaat actaaagaca atgaacgtgt tgtgggcttt cacgtactgg 2221 gtccaaatgc tggagaagtt acacaaggct ttgcagctgc gctcaaatgt ggactgacca 2281 aaaagcagct ggacagcaca attggaatcc accctgtctg tgcagaggta ttcacaacat 2341 tgtctgtgac caagcgctct ggggcaagca tcctccaggc tggctgctga ggttaagccc 2401 cagtgtggat gctgttgcca agactgcaaa ccactggctc gtttccgtgc ccaaatccaa 2461 ggcgaagttt tctagagggt tcttgggctc ttggcacctg cgtgtcctgc gcttaccacc 2521 gcccaaggcc cccttggatc tcttggatag gagttggtga atagaaggca ggcagcatca 2581 cactggggtc actgacagac ttgaagctga catttggcag ggcatcgaag ggatgcatcc 2641 atgaagtcac cagtctcaag cccatgtggt aggcggtgat ggaacaactg tcaaatcagt 2701 tttagcatga cctttccttg tggattttct tattctcgtt gtcaagtttt ctagggttga 2761 attttttct tttttctcca tggtgttaat gatattagag atgaaaaacg ttagcagttg 2821 attttgtcc aaaagcaagt catggctaga gtatccatgc aaggtgtctt gttgcatgga 2881 agggatagtt tggctccctt ggaggctatg taggcttgtc ccgggaaaga gaactgtcct 2941 gcagctgaaa tggactgttc tttactgacc tgctcagcag tttcttctct catatattcc 3001 caaaacaagt acatctgcga tcaactctag ccaaatttgc ccctgtgtgc tacatgatgg 3061 atgattatta tttttaaggtc tgtttaggaa gggaaatggc tacttggcca gccattgcct 3121 ggcatttggt agtatagtat gattctcacc attatttgtc atggaggcag acatacacca 3181 gaaatggggg agaaacagta catatctttc tgtctttagt ttattgtgtg ctggtctaag 3241 caagctgaga tcatttgcaa tggaaaacac gtaacttgtt taaaagtttt tctggtagct 3301 ttagctttat gctaaaaaaa ataatgacat tgggtatcta tttctttcta agactacatt 3361 agtaggaaaa taagtctttt catgcttatg atttagctgt tttgtggtaa ttgcttttta 3421 aaggaagtta ttaatatcat aagttattat taatattttg aacacaggtg gatgtgaagg 3481 attttcattt aaaaaccaag tggttttgac tttttctgtt gaatgaacaa ctgtgccttg 3541 tggaatttt gcagaagtgt ttatgctttg ttagcatttc aacttgcatt attataaaga 3601 ggtattaatg cctcagttat gtgtttgtca atgtactggc tgaggattct atctcagctg 3661 tcttttctaa ctgtgtaggt tgagtttga acacgtgctt gtggacatca ggcctcctgc 3721 cagcagttct tgaagcttct ttttcattcc tgctactcta cctgtatttc tcagttgcag 3781 cactgagtgg tcaaaataca tttctgggcc acctcaggga acccatgcat ctgcctggca 3841 tttaggcagc agagcccctg accgtccccc acagggctct gcctcacgtc ctcatctcat 3901 ttggctgtgt aaagaaatgg gaaaagggaa aaggagagag caattgaggc agttgaccat 3961 attcagtttt atttatttat ttttaatttg ttttttttctc caagtccacc agtctctgaa 4021 attagaacag taggcggtat gagataatca ggcctaatca tgttgtgatt ctcttttctt
```

-continued

```
4081 agtggagtgg aatgttctat ccccacaaga aggattatat cttatagact tgtcttgttc 4141 agattctgta tttacccatt ttattgaaac atatactaag ttccatgtat ttttgttaca 4201 aatcttctga aaaaaaacaa aacaatgtga aacattaaaa ttaaaaggca ttaataatat 4261 ccacgtgtgc cttcttactg aaaaaaaaaa a
```

*Homo sapiens* thioredoxin reductase 1 (TXNRD1), transcript variant 6, mRNA
NCBI Reference Sequence: NM_001261446.1

(SEQ ID NO: 18)

```
   1 agaccctcac gtgatgacaa cagctagcaa agttctgtag ctactgcctt agggcatagt 61 ctaatttctt cagtaaaaac acacttattc caaatttggt tccagaattg ccttaaattg 121 tttttgctct gttcttaggt tgggggcggc tatgagcagg cagaggatgt ggtgtcaccc 181 aattaggagc tctcagctta cgaggcaatt agcataggtt gccagggctg cacgaggagt 241 ggatttctgc tttgtcattc tgactctggc agttagcccg cccgctcggc gcagggcgtg 301 gcttctcgta gccattagga aacagcaacc ctttcacctc agttttcttc actccggcat 361 ttgcagcaga gcgaaaggtg gtcgagtcct gaaggagggc ctgatgtctt catcattctc 421 aaattcttag gacggtcggg ccctggaagg aacgctctcg gaattggccg cggaaaccga 481 tctgcccgtt gtgtttgtga aacagagaaa gataggcggc catggtccaa ccttgaagga 541 ggcagcccaa tatggcaaga aggtgatggt cctggacttt gtcactccca cccctcttgg 601 aactagatgg ggtctcggag gaacatgtgt gaatgtgggt tgcataccta aaaaactgat 661 gcatcaagca gctttgttag gacaagccct gcaagactct cgaaattatg gatggaaagt 721 cgaggagaca gttaagcatg attgggacag aatgatagaa gctgtacaga atcacattgg 781 ctctttgaat tggggctacc gagtagctct gcgggagaaa aaagtcgtct atgagaatgc 841 ttatgggcaa tttattggtc ctcacaggat taaggcaaca aataataaag gcaaagaaaa 901 aatttattca gcagagagat ttctcattgc cactggtgaa agaccacgtt acttgggcat 961 ccctggtgac aaagaatact gcatcagcag tgatgatctt ttctccttgc cttactgccc 1021 gggtaagacc ctggttgttg gagcatccta tgtcgctttg gagtgcgctg gatttcttgc 1081 tggtattggt ttagacgtca ctgttatggt taggtccatt cttcttagag gatttgacca 1141 ggacatggcc aacaaaattg gtgaacacat ggaagaacat ggcatcaagt ttataagaca 1201 gttcgtacca attaaagttg aacaaattga agcagggaca ccaggccgac tcagagtagt 1261 agctcagtcc accaatagtg aggaaatcat tgaaggagaa tataatacgg tgatgctggc 1321 aataggaaga gatgcttgca caagaaaaat tggcttagaa accgtagggg tgaagataaa 1381 tgaaaagact ggaaaaatac ctgtcacaga tgaagaacag accaatgtgc cttacatcta 1441 tgccattggc gatatattgg aggataaggt ggagctcacc ccagttgcaa tccaggcagg 1501 aagattgctg gctcagaggc tctatgcagg ttccactgtc aagtgtgact atgaaaatgt 1561 tccaaccact gtatttactc ctttggaata tggtgcttgt ggcctttctg aggagaaagc 1621 tgtggagaag tttgggggaag aaaatattga ggtttaccat agttactttt ggccattgga 1681 atggacgatt ccgtcaagag ataacaacaa atgttatgca aaaataatct gtaatactaa 1741 agacaatgaa cgtgttgtgg gctttcacgt actgggtcca aatgctggag aagttacaca 1801 aggctttgca gctgcgctca aatgtggact gaccaaaaag cagctggaca gcacaattgg 1861 aatccaccct gtctgtgcag aggtattcac aacattgtct gtgaccaagc gctctggggc 1921 aagcatcctc caggctggct gctgaggtta agccccagtg tggatgctgt tgccaagact 1981 gcaaaccact ggctcgtttc cgtgcccaaa tccaaggcga agttttctag agggttcttg 2041 ggctcttggc acctgcgtgt cctgtgctta ccaccgccca aggcccccctt ggatctcttg
```

-continued

```
2101 gataggagtt ggtgaataga aggcaggcag catcacactg gggtcactga cagacttgaa 2161 gctgacattt ggcagggcat cgaagggatg catccatgaa gtcaccagtc tcaagcccat 2221 gtggtaggcg gtgatggaac aactgtcaaa tcagttttag catgaccttt ccttgtggat 2281 tttcttattc tcgttgtcaa gttttctagg gttgaatttt tttctttttt ctccatggtg 2341 ttaatgatat tagagatgaa aaacgttagc agttgatttt tgtccaaaag caagtcatgg 2401 ctagagtatc catgcaaggt gtcttgttgc atggaaggga tagtttggct cccttggagg 2461 ctatgtaggc ttgtcccggg aaagagaact gtcctgcagc tgaaatggac tgttctttac 2521 tgacctgctc agcagtttct tctctcatat attcccaaaa caagtacatc tgcgatcaac 2581 tctagccaaa tttgcccctg tgtgctacat gatggatgat tattatttta aggtctgttt 2641 aggaagggaa atggctactt ggccagccat tgcctggcat ttggtagtat agtatgattc 2701 tcaccattat ttgtcatgga ggcagacata caccagaaat gggggagaaa cagtacatat 2761 ctttctgtct ttagtttatt gtgtgctggt ctaagcaagc tgagatcatt tgcaatggaa 2821 aacacgtaac ttgtttaaaa gttttctgg tagctttagc tttatgctaa aaaaaataat 2881 gacattgggt atctatttct ttctaagact acattagtag gaaaataagt cttttcatgc 2941 ttatgattta gctgttttgt ggtaattgct ttttaaagga agttattaat atcataagtt 3001 attattaata ttttgaacac aggtggatgt gaaggatttt catttaaaaa ccaagtggtt 3061 ttgacttttt ctgttgaatg aacaactgtg ccttgtggaa tttttgcaga agtgtttatg 3121 ctttgttagc atttcaactt gcattattat aaagaggtat taatgcctca gttatgtgtt 3181 tgtcaatgta ctggctgagg attctatctc agctgtcttt tctaactgtg taggttgagt 3241 tttgaacacg tgcttgtgga catcaggcct cctgccagca gttcttgaag cttctttttc 3301 attcctgcta ctctacctgt atttctcagt tgcagcactg agtggtcaaa atacatttct 3361 gggccacctc agggaaccca tgcatctgcc tggcatttag gcagcagagc ccctgaccgt 3421 cccccacagg gctctgcctc acgtcctcat ctcatttggc tgtgtaaaga aatgggaaaa 3481 gggaaaagga gagagcaatt gaggcagttg accatattca gttttatta tttattttta 3541 atttgttttt ttctccaagt ccaccagtct ctgaaattag aacagtaggc ggtatgagat 3601 aatcaggcct aatcatgttg tgattctctt ttcttagtgg agtggaatgt tctatcccca 3661 caagaaggat tatatcttat agacttgtct tgttcagatt ctgtatttac ccattttatt 3721 gaaacatata ctaagttcca tgtattttg ttacaaatct tctgaaaaaa aacaaaacaa 3781 tgtgaaacat taaaattaaa aggcattaat aatatccacg tgtgccttct tactgaaaaa 3841 aaaaaa
```

*Homo sapiens* thioredoxin reductase 1 (TXNRD1), transcript variant 7, mRNA
NCBI Reference Sequence: NM_001093771.3

(SEQ ID NO: 19)

```
   1 agttcccaca gggccttgtg cgacatgggc tgcgccgagg gcaaggcagt ggcggcggcc 61 gccccaacgg agctgcagac gaaaggcaag aacggcgatg gccgccgtag gtcagctaaa 121 gatcatcacc ctggtaaaac tttgccagag aacccagcag gattcaccag cacggccact 181 gcagactcca gagccctgct tcaggcctat atagatggtc actctgtggt catcttcagt 241 aggtccacat gcacacgctg tactgaggta aagaagttat ttaaatctct gtgtgttcct 301 tattttgtgc ttgaacttga tcaaacagag gacggtcggg ccctggaagg aacgctctcg 361 gaattggccg cggaaaccga tctgcccgtt gtgtttgtga acagagaaa gataggcggc 421 catggtccaa ccttgaaggc ttatcaggag ggcagacttc aaaagctact aaaaatgaac 481 ggccctgaag atcttcccaa gtcctatgac tatgacctta tcatcattgg aggtggctca
```

-continued

```
 541 ggaggtctgg cagctgctaa ggaggcagcc caatatggca agaaggtgat ggtcctggac 601 tttgtcactc ccacccctct tggaactaga tggggtctcg gaggaacatg tgtgaatgtg 661 ggttgcatac ctaaaaaact gatgcatcaa gcagctttgt taggacaagc cctgcaagac 721 tctcgaaatt atggatggaa agtcgaggag acagttaagc atgattggga cagaatgata 781 gaagctgtac agaatcacat tggctctttg aattggggct accgagtagc tctgcgggag 841 aaaaaagtcg tctatgagaa tgcttatggg caatttattg gtcctcacag gattaaggca 901 acaaataata aaggcaaaga aaaaatttat tcagcagaga gatttctcat tgccactggt 961 gaaagaccac gttacttggg catccctggt gacaaagaat actgcatcag cagtgatgat 1021 cttttctcct tgccttactg cccgggtaag accctggttg ttggagcatc ctatgtcgct 1081 ttggagtgcg ctggatttct tgctggtatt ggtttagacg tcactgttat ggttaggtcc 1141 attcttctta gaggatttga ccaggacatg gccaacaaaa ttggtgaaca catggaagaa 1201 catggcatca agtttataag acagttcgta ccaattaaag ttgaacaaat tgaagcaggg 1261 acaccaggcc gactcagagt agtagctcag tccaccaata gtgaggaaat cattgaagga 1321 gaatataata cggtgatgct ggcaatagga agagatgctt gcacaagaaa aattggctta 1381 gaaaccgtag gggtgaagat aaatgaaaag actggaaaaa tacctgtcac agatgaagaa 1441 cagaccaatg tgccttacat ctatgccatt ggcgatatat tggaggataa ggtggagctc 1501 accccagttg caatccaggc aggaagattg ctggctcaga ggctctatgc aggttccact 1561 gtcaagtgtg actatgaaaa tgttccaacc actgtattta ctcctttgga atatggtgct 1621 tgtggccttt ctgaggagaa agctgtggag aagtttgggg aagaaaatat tgaggtttac 1681 catagttact tttggccatt ggaatggacg attccgtcaa gagataacaa caaatgttat 1741 gcaaaaataa tctgtaatac taaagacaat gaacgtgttg tgggctttca cgtactgggt 1801 ccaaatgctg agaagttac acaaggcttt gcagctgcgc tcaaatgtgg actgaccaaa 1861 aagcagctgg acagcacaat tggaatccac cctgtctgtg cagaggtatt cacaacattg 1921 tctgtgacca agcgctctgg ggcaagcatc ctccaggctg gctgctgagg ttaagccccca 1981 gtgtggatgc tgttgccaag actgcaaacc actggctcgt ttccgtgccc aaatccaagg 2041 cgaagttttc tagagggttc ttgggctctt ggcacctgcg tgtcctgtgc ttaccaccgc 2101 ccaaggcccc cttggatctc ttggatagga gttggtgaat agaaggcagg cagcatcaca 2161 ctggggtcac tgacagactt gaagctgaca tttggcaggg catcgaaggg atgcatccat 2221 gaagtcacca gtctcaagcc catgtggtag gcggtgatgg aacaactgtc aaatcagttt 2281 tagcatgacc tttccttgtg gattttctta ttctcgttgt caagtttttct agggttgaat 2341 ttttttcttt tttctccatg gtgttaatga tattagagat gaaaaacgtt agcagttgat 2401 ttttgtccaa aagcaagtca tggctagagt atccatgcaa ggtgtcttgt tgcatggaag 2461 ggatagtttg gctcccttgg aggctatgta ggcttgtccc gggaaagaga actgtcctgc 2521 agctgaaatg gactgttctt tactgacctg ctcagcagtt cttctctca tatattccca 2581 aaacaagtac atctgcgatc aactctagcc aaatttgccc ctgtgtgcta catgatggat 2641 gattattatt ttaaggtctg tttaggaagg gaaatggcta cttggccagc cattgcctgg 2701 catttggtag tatagtatga ttctcaccat tatttgtcat ggaggcagac atacaccaga 2761 aatggggggag aaacagtaca tatctttctg tctttagttt attgtgtgct ggtctaagca 2821 agctgagatc atttgcaatg gaaaacacgt aacttgttta aaagttttttc tggtagcttt 2881 agctttatgc taaaaaaaat aatgacattg ggtatctatt tctttctaag actacattag 2941 taggaaaata agtctttttca tgcttatgat ttagctgttt tgtggtaatt gcttttttaaa
```

-continued

```
3001 ggaagttatt aatatcataa gttattatta atattttgaa cacaggtgga tgtgaaggat 3061 tttcatttaa aaaccaagtg gttttgactt tttctgttga atgaacaact gtgccttgtg 3121 gaatttttgc agaagtgttt atgctttgtt agcatttcaa cttgcattat tataaagagg 3181 tattaatgcc tcagttatgt gtttgtcaat gtactggctg aggattctat ctcagctgtc 3241 ttttctaact gtgtaggttg agttttgaac acgtgcttgt ggacatcagg cctcctgcca 3301 gcagttcttg aagcttcttt ttcattcctg ctactctacc tgtatttctc agttgcagca 3361 ctgagtggtc aaaatacatt tctgggccac ctcagggaac ccatgcatct gcctggcatt 3421 taggcagcag agcccctgac cgtcccccac agggctctgc ctcacgtcct catctcattt 3481 ggctgtgtaa agaaatggga aaagggaaaa ggagagagca attgaggcag ttgaccatat 3541 tcagttttat ttatttattt ttaatttgtt tttttctcca agtccaccag tctctgaaat 3601 tagaacagta ggcggtatga gataatcagg cctaatcatg ttgtgattct cttttcttag 3661 tggagtggaa tgttctatcc ccacaagaag gattatatct tatagacttg tcttgttcag 3721 attctgtatt tacccatttt attgaaacat atactaagtt ccatgtattt ttgttacaaa 3781 tcttctgaaa aaaacaaaa caatgtgaaa cattaaaatt aaaaggcatt aataatatcc 3841 acgtgtgcct tcttactgaa
```

*Mus musculus* thioredoxin reductase 1 (Txnrd1), transcript variant 1, mRNA
NCBI Reference Sequence: NM_001042513.1

(SEQ ID NO: 20)

```
   1 agtttgcttc cgtcaggcct cgcgtccacg cgggaggtgc gggacgccga caccgcgggg 61 cgagaagagc tggtggtttc accttccttg ttcatagggc ggcggggcct tgcagcggcg 121 cgggcgagcg gaaaggccgc gggaggcggc gagccagcgg aaggtgcgac cggcggaggg 181 cggccatggt ccagcccctga agccgaacaa aaaaggccaa cttcaaaagc tgccaacaat 241 gaatggctcc aaagatcccc ctgggtccta tgacttcgac ctgatcatca ttggaggagg 301 ctcaggagga ctggcagcag ctaaggaggc agccaaattt gacaagaaag tgctggtctt 361 ggattttgtc acaccgactc ctcttgggac cagatggggt ctcggaggaa cgtgtgtgaa 421 tgtgggttgc atacctaaga agctgatgca ccaggcagct ttgctcggac aagctctgaa 481 agactcgcgc aactatggct ggaaagtcga agacacagtg aagcatgact gggagaaaat 541 gacggaatct gtgcagagtc acatcggctc gctgaactgg ggctaccgcg tagctctccg 601 ggagaaaaag gtcgtctatg agaatgctta cgggaggttc attggtcctc acaggattgt 661 ggcgacaaat aacaaaggta agaaaaaat ctattcagca gagcggttcc tcatcgccac 721 aggtgagagg ccccgctacc tgggcatccc tggagacaaa gagtactgca tcagcagtga 781 tgatcttttc tccttgcctt actgcccggg gaagacccta gtagttggtg catcctatgt 841 cgccttggaa tgtgcaggat ttctggctgg tatcggctta gacgtcactg taatggtgcg 901 gtccattctc cttagaggat ttgaccaaga catggccaac aaaatcggtg aacacatgga 961 agaacatggt atcaagttta taaggcagtt cgtcccaacg aaaattgaac agatcgaagc 1021 aggaacacca ggccgactca gggtgactgc tcaatccaca aacagcgagg agaccataga 1081 gggcgaattt aacacagtgt tgctggcggt aggaagagat tcttgtacga gaactattgg 1141 cttagagacc gtgggcgtga agataaacga aaaaccggaa gatacccg tcacggatga 1201 agagcagacc aatgtgcctt acatctacgc catcggtgac atcctggagg ggaagctaga 1261 gctgactccc gtagccatcc aggcggggag attgctggct cagaggctgt atggaggctc 1321 caatgtcaaa tgtgactatg acaatgtccc aacgactgta tttactcctt tggaatatgg 1381 ctgttgtggc ctctctgaag aaaaagccgt agagaaattt ggggaagaaa atattgaagt
```

-continued

```
1441 ttaccatagt ttcttttggc cattggaatg gacagtccca tcccgggata acaacaaatg 1501 ttatgcaaaa ataatctgca accttaaaga cgatgaacgt gtcgtgggct tccacgtgct 1561 gggtccaaac gctggagagg tgacgcaggg ctttgcggct gcgctcaagt gtgggctgac 1621 taagcagcag ctggacagca ccatcggcat ccacccggtc tgtgcagaga tattcacaac 1681 gttgtcagtg acgaagcgct ctgggggaga catcctccag tctggctgct gaggttaagc 1741 cccagtgtgg atgctgttgc caagactaca gaccattgcc ttgcttcctt gcccacgccc 1801 aggtgaagtt caggaaggct cttgggtcct aggcgccaat tcaaggtgct gtcctaaggc 1861 caccgggtcc ctgggatctt gtgggtagga ggtggcaggt cgaaggaggc tgcagcatcg 1921 cactggggtc accatgacag actcagactg acatctggca gagcatcaca ggcatgcgtc 1981 catgaagtca ctggcctcaa gcccaagtgg tgggcagtga cagaagagct gccgggtctg 2041 ttgagctcaa ccttttcctg tagattgtct tagtctcact ttcaagctgt ctaatgtcaa 2101 ttctgttttt cttttttcct ccatggggtt aatgatacta gagataggga atattagcaa 2161 tcagtttttg tcatggctgg tccatctgca acagtcttta ctgtgtggaa gtgggtgaga 2221 tggcttatga gagccaaacc aatttatccc cagaaagacg aattaccctg tgactaaaat 2281 acactgtctg cttttactaa ctggtgtagc attgtctcct ttaataagtc ttgtgtccaa 2341 aacgagaaaa accattggcc acttttgcaa gtttcctgca gtgtgcttag caagggaggt 2401 ggcgacttgg ctaatctact tgaactgcat cgcatggctc ttgggtagct tagagcatcg 2461 cagggtagag gcagaccagc agtgagtgtc tctcctggta caattattgt ctggttctca 2521 gtggaaaacg cttaatttgc tttaaacttg gtgtttttgt gaggtggatt tagtcttaag 2581 ctgtgtccca taagaactac attcacaggc aagtggctct tcctccacac agcctataca 2641 tcttctgagg taattacttt cataaggaag ctgttcataa cgtaagttat tattattatt 2701 gaacacaggt ggatgtgaag gatttttcat tgaaaaacca aatggttttt cttttttct 2761 gttcagtgag cccacaggaa ctctgtcagg acagccagta ctctgccggc atggctgctg 2821 gggcgtttac ggtgtagttt agctcctagg ttacatgacc gtgaacatgc tggctgagga 2881 ctacacaaac caggtttccc accatacacg gcctggccct gcagcttctt ttcttgccct 2941 cccctttgcc tgtccccacc tgcagtactg agtggcgttt cacagtaccc ttctgggcca 3001 cctcagggaa gggatttgcc tggtgtccag ccagcagcac ccaccctgcc ccacgaggct 3061 ccctcacacc tgccccccccg tccttgtgtt gaagacagtg ggaagaggag aaaggaccag 3121 ggaaaccaag ggagttgact gttcagtttt atttatttat tttttaagtt ttttttttcct 3181 ttcaagtctg ccagtctctg agatcagaac aacagacagt gtagggtaac taatcatgtg 3241 attctcttag tggaatgaaa tgttctaccc ccacaagaag gagtatacg cattgttcat 3301 attctgtaat cgcacaatgt attgtaatgc aaattccaat tccatgtatt tttattacaa 3361 tttttctgga aaaaaatgtg aaccaataaa agatgttgat gcacacgcgt gccttct
```

*Mus musculus* thioredoxin reductase 1 (Txnrd1), transcript variant 3, mRNA
NCBI Reference Sequence: NM_001042514.1

(SEQ ID NO: 21)

```
   1 gtggctacga ggctggtgtt tttagccgcc atgcagagct tttctgagtt ctgggggtcc 61 tggagtcttg ctggcccggc tgcttaaggg tcggagtcca ctggcgagag tgacccaggg 121 cgcgtggcgt cccggaagcc ccgcccggag gaaggctcac tgccgctctg ctttgtgcca 181 cagagggcgg cggggccttg cagcggcgcg ggcgagcgga aaggccgcgg gaggcggcga 241 gccagcggaa ggtgcgaccg gcggagggcg gccatggtcc agccctgaag ccgaacaaaa 301 aaggccaact tcaaaagctg ccaacaatga atggctccaa agatccccct gggtcctatg
```

-continued

```
 361  acttcgacct gatcatcatt ggaggaggct caggaggact ggcagcagct aaggaggcag 421  ccaaatttga caagaaagtg ctggtcttgg attttgtcac accgactcct cttgggacca 481  gatggggtct cggaggaacg tgtgtgaatg tgggttgcat acctaagaag ctgatgcacc 541  aggcagcttt gctcggacaa gctctgaaag actcgcgcaa ctatggctgg aaagtcgaag 601  acacagtgaa gcatgactgg gagaaaatga cggaatctgt gcagagtcac atcggctcgc 661  tgaactgggg ctaccgcgta gctctccggg agaaaaaggt cgtctatgag aatgcttacg 721  ggaggttcat tggtcctcac aggattgtgg cgacaaataa caaaggtaaa gaaaaaatct 781  attcagcaga gcggttcctc atcgccacag gtgagaggcc ccgctacctg ggcatccctg 841  gagacaaaga gtactgcatc agcagtgatg atctttctc cttgccttac tgcccgggga 901  agaccctagt agttggtgca tcctatgtcg ccttggaatg tgcaggattt ctggctggta 961  tcggcttaga cgtcactgta atggtgcggt ccattctcct tagaggattt gaccaagaca 1021  tggccaacaa aatcggtgaa cacatggaag aacatggtat caagtttata aggcagttcg 1081  tcccaacgaa aattgaacag atcgaagcag gaacaccagg ccgactcagg gtgactgctc 1141  aatccacaaa cagcgaggag accatagagg gcgaatttaa cacagtgttg ctggcggtag 1201  gaagagattc ttgtacgaga actattggct tagagaccgt gggcgtgaag ataaacgaaa 1261  aaaccggaaa gatacccgtc acggatgaag agcagaccaa tgtgccttac atctacgcca 1321  tcggtgacat cctggagggg aagctagagc tgactcccgt agccatccag gcggggagat 1381  tgctggctca gaggctgtat ggaggctcca atgtcaaatg tgactatgac aatgtcccaa 1441  cgactgtatt tactcctttg gaatatggct gttgtggcct ctctgaagaa aaagccgtag 1501  agaaatttgg ggaagaaaat attgaagttt accatagttt cttttggcca ttggaatgga 1561  cagtcccatc ccgggataac aacaaatgtt atgcaaaaat aatctgcaac cttaaagacg 1621  atgaacgtgt cgtgggcttc cacgtgctgg gtccaaacgc tggagaggtg acgcagggct 1681  ttgcggctgc gctcaagtgt gggctgacta agcagcagct ggacagcacc atcggcatcc 1741  acccggtctg tgcagagata ttcacaacgt tgtcagtgac gaagcgctct gggggagaca 1801  tcctccagtc tggctgctga ggttaagccc cagtgtggat gctgttgcca agactacaga 1861  ccattgcctt gcttccttgc ccacgcccag gtgaagttca ggaaggctct tgggtcctag 1921  gcgccaattc aaggtgctgt cctaaggcca ccgggtccct gggatcttgt gggtaggagg 1981  tggcaggtcg aaggaggctg cagcatcgca ctggggtcac catgacagac tcagactgac 2041  atctggcaga gcatcacagg catgcgtcca tgaagtcact ggcctcaagc ccaagtggtg 2101  ggcagtgaca aagagctgc cgggtctgtt gagctcaacc ttttcctgta gattgtctta 2161  gtctcacttt caagctgtct aatgtcaatt ctgttttct ttttcctcc atggggttaa 2221  tgatactaga gatagggaat attagcaatc agttttgtc atggctggtc catctgcaac 2281  agtctttact gtgtggaagt gggtgagatg gcttatgaga gccaaaccaa tttatcccca 2341  gaaagacgaa ttaccctgtg actaaaatac actgtctgct tttactaact ggtgtagcat 2401  tgtctccttt aataagtctt gtgtccaaaa cgagaaaaac cattggccac tttttgcaagt 2461  ttcctgcagt gtgcttagca agggaggtgg cgacttggct aatctacttg aactgcatcg 2521  catggctctt gggtagctta gagcatcgca gggtagaggc agaccagcag tgagtgtctc 2581  tcctggtaca attattgtct ggttctcagt ggaaaacgct taatttgctt taaacttggt 2641  gtttttgtga ggtggattta gtcttaagct gtgtcccata agaactacat tcacaggcaa 2701  gtggctcttc ctccacacag cctatacatc ttctgaggta attactttca taaggaagct
```

-continued

```
2761 gttcataacg taagttatta ttattattga acacaggtgg atgtgaagga ttttttcattg 2821 aaaaaccaaa tggttttttct tttttttctgt tcagtgagcc cacaggaact ctgtcaggac 2881 agccagtact ctgccggcat ggctgctggg gcgtttacgg tgtagtttag ctcctaggtt 2941 acatgaccgt gaacatgctg gctgaggact acacaaacca ggtttcccac catacacggc 3001 ctggccctgc agcttctttt cttgccctcc cctttgcctg tccccacctg cagtactgag 3061 tggcgtttca cagtacccctt ctgggccacc tcaggaagg gatttgcctg gtgtccagcc 3121 agcagcaccc accctgcccc acgaggctcc ctcacacctg cccccccgtc cttgtgttga 3181 agacagtggg aagaggagaa aggaccaggg aaaccaaggg agttgactgt tcagtttttat 3241 ttatttattt tttaagtttt tttttccttt caagtctgcc agtctctgag atcagaacaa 3301 cagacagtgt agggtaacta atcatgtgat tctcttagtg gaatgaaatg ttctaccccc 3361 acaagaagga gtatacgtca ttgttcatat tctgtaatcg cacaatgtat tgtaatgcaa 3421 attccaattc catgtatttt tattacaatt tttctggaaa aaaatgtgaa ccaataaaag 3481 atgttgatgc acacgcgtgc cttct
```

*Mus musculus* thioredoxin reductase 1 (Txnrd1), transcript variant 2, mRNA
NCBI Reference Sequence: NM_015762.2

(SEQ ID NO: 22)

```
   1 agtttgcttc cgtcaggcct cgcgtccacg cgggaggtgc gggacgccga caccgcgggg 61 cgagaagagc tggtggtttc accttccttg ttcatccgaa caaaaaggc caacttcaaa 121 agctgccaac aatgaatggc tccaaagatc cccctgggtc ctatgacttc gacctgatca 181 tcattggagg aggctcagga ggactggcag cagctaagga ggcagccaaa tttgacaaga 241 aagtgctggt cttggatttt gtcacaccga ctcctcttgg gaccagatgg ggtctcggag 301 gaacgtgtgt gaatgtgggt tgcataccta agaagctgat gcaccaggca gctttgctcg 361 gacaagctct gaaagactcg cgcaactatg gctggaaagt cgaagacaca gtgaagcatg 421 actgggagaa aatgacggaa tctgtgcaga gtcacatcgg ctcgctgaac tggggctacc 481 gcgtagctct ccgggagaaa aaggtcgtct atgagaatgc ttacgggagg ttcattggtc 541 ctcacaggat tgtggcgaca aataacaaag gtaaagaaaa aatctattca gcagagcggt 601 tcctcatcgc cacaggtgag aggccccgct acctgggcat ccctggagac aaagagtact 661 gcatcagcag tgatgatctt ttctccttgc cttactgccc ggggaagacc ctagtagttg 721 gtgcatccta tgtcgccttg gaatgtgcag gatttctggc tggtatcggc ttagacgtca 781 ctgtaatggt gcggtccatt ctccttagag gatttgacca agacatggcc aacaaaatcg 841 gtgaacacat ggaagaacat ggtatcaagt ttataaggca gttcgtccca acgaaaattg 901 aacagatcga agcaggaaca ccaggccgac tcagggtgac tgctcaatcc acaaacagcg 961 aggagaccat agagggcgaa tttaacacag tgttgctggc ggtaggaaga gattcttgta 1021 cgagaactat tggcttagag accgtgggcg tgaagataaa cgaaaaaacc ggaaagatac 1081 ccgtcacgga tgaagagcag accaatgtgc cttacatcta cgccatcggt gacatcctgg 1141 aggggaagct agagctgact cccgtagcca tccaggcggg gagattgctg gctcagaggc 1201 tgtatggagg ctccaatgtc aaatgtgact atgacaatgt cccaacgact gtatttactc 1261 ctttggaata tggctgttgt ggcctctctg aagaaaaagc cgtagagaaa tttgggggaag 1321 aaaatattga agtttaccat agtttctttt ggccattgga atggacagtc ccatcccggg 1381 ataacaacaa atgttatgca aaaataatct gcaaccttaa agacgatgaa cgtgtcgtgg 1441 gcttccacgt gctgggtcca aacgctggag aggtgacgca gggctttgcg gctgcgctca 1501 agtgtgggct gactaagcag cagctggaca gcaccatcgg catccacccg gtctgtgcag
```

-continued

```
1561 agatattcac aacgttgtca gtgacgaagc gctctggggg agacatcctc cagtctggct 1621 gctgaggtta agccccagtg tggatgctgt tgccaagact acagaccatt gccttgcttc 1681 cttgcccacg cccaggtgaa gttcaggaag gctcttgggt cctaggcgcc aattcaaggt 1741 gctgtcctaa ggccaccggg tccctgggat cttgtgggta ggaggtggca ggtcgaagga 1801 ggctgcagca tcgcactggg gtcaccatga cagactcaga ctgacatctg gcagagcatc 1861 acaggcatgc gtccatgaag tcactggcct caagcccaag tggtgggcag tgacagaaga 1921 gctgccgggt ctgttgagct caaccttttc ctgtagattg tcttagtctc actttcaagc 1981 tgtctaatgt caattctgtt tttctttttt cctccatggg gttaatgata ctagagatag 2041 ggaatattag caatcagttt ttgtcatggc tggtccatct gcaacagtct ttactgtgtg 2101 gaagtgggtg agatggctta tgagagccaa accaatttat ccccagaaag acgaattacc 2161 ctgtgactaa aatacactgt ctgcttttac taactggtgt agcattgtct cctttaataa 2221 gtcttgtgtc caaaacgaga aaaaccattg gccacttttg caagtttcct gcagtgtgct 2281 tagcaaggga ggtggcgact tggctaatct acttgaactg catcgcatgg ctcttgggta 2341 gcttagagca tcgcagggta gaggcagacc agcagtgagt gtctctcctg gtacaattat 2401 tgtctggttc tcagtggaaa acgcttaatt tgctttaaac ttggtgtttt tgtgaggtgg 2461 atttagtctt aagctgtgtc ccataagaac tacattcaca ggcaagtggc tcttcctcca 2521 cacagcctat acatcttctg aggtaattac tttcataagg aagctgttca taacgtaagt 2581 tattattatt attgaacaca ggtggatgtg aaggattttt cattgaaaaa ccaaatggtt 2641 tttctttttt tctgttcagt gagcccacag gaactctgtc aggacagcca gtactctgcc 2701 ggcatggctg ctggggcgtt tacggtgtag tttagctcct aggttacatg accgtgaaca 2761 tgctggctga ggactacaca aaccaggttt cccaccatac acggcctggc cctgcagctt 2821 cttttcttgc cctccccttt gcctgtcccc acctgcagta ctgagtggcg tttcacagta 2881 cccttctggg ccacctcagg gaagggattt gcctggtgtc cagccagcag cacccaccct 2941 gccccacgag gctccctcac acctgccccc ccgtccttgt gttgaagaca gtgggaagag 3001 gagaaaggac cagggaaacc aagggagttg actgttcagt tttatttatt tattttttaa 3061 gtttttttt cctttcaagt ctgccagtct ctgagatcag aacaacagac agtgtagggt 3121 aactaatcat gtgattctct tagtggaatg aaatgttcta cccccacaag aaggagtata 3181 cgtcattgtt catattctgt aatcgcacaa tgtattgtaa tgcaaattcc aattccatgt 3241 attttatta caattttct ggaaaaaaat gtgaaccaat aaaagatgtt gatgcacacg 3301 cgtgccttct
```

*Mus musculus* thioredoxin reductase 1 (Txnrd1), transcript variant 4, mRNA
NCBI Reference Sequence: NM_001042523.1

(SEQ ID NO: 23)

```
   1 caggctccac cagtgcttct gcagacctca gagcctggcg gctggcctca taaacagccg 61 tgcggtggac actctactaa gtgccctgca ttgaaggaga agccctggtc accatgccag 121 ttgatgactg ctggctgtac ttcccagctt ctcgaggtag aacctttgtg cagactgtct 181 gggtggcacc cacttgcccc aactgttgct ggtttccagg ttttctccct ccagtccccc 241 ggccaccaca tgtgccccgt gtgctgctga ggggccctcg tggggctgtg cttcctgctt 301 cacgtccctc caagacactc ccctcctcat cccagacgcc ctgtcctact gaccctgta 361 tctgccctcc accctccaca cctgatagta ggcaggaaaa aaatacgcaa tctgagctgc 421 cgaacaaaaa aggccaactt caaaagctgc caacaatgaa tggctccaaa gatccccctg 481 ggtcctatga cttcgacctg atcatcattg gaggaggctc aggaggactg gcagcagcta
```

-continued

```
 541 aggaggcagc caaatttgac aagaaagtgc tggtcttgga ttttgtcaca ccgactcctc 601 ttgggaccag atggggtctc ggaggaacgt gtgtgaatgt gggttgcata cctaagaagc 661 tgatgcacca ggcagctttg ctcggacaag ctctgaaaga ctcgcgcaac tatggctgga 721 aagtcgaaga cacagtgaag catgactggg agaaaatgac ggaatctgtg cagagtcaca 781 tcggctcgct gaactggggc taccgcgtag ctctccggga gaaaaaggtc gtctatgaga 841 atgcttacgg gaggttcatt ggtcctcaca ggattgtggc gacaaataac aaaggtaaag 901 aaaaaatcta ttcagcagag cggttcctca tcgccacagg tgagaggccc cgctacctgg 961 gcatccctgg agacaaagag tactgcatca gcagtgatga tcttttctcc ttgccttact 1021 gcccggggaa gaccctagta gttggtgcat cctatgtcgc cttggaatgt gcaggatttc 1081 tggctggtat cggcttagac gtcactgtaa tggtgcggtc cattctcctt agaggatttg 1141 accaagacat ggccaacaaa atcggtgaac acatggaaga acatggtatc aagtttataa 1201 ggcagttcgt cccaacgaaa attgaacaga tcgaagcagg aacaccaggc cgactcaggg 1261 tgactgctca atccacaaac agcgaggaga ccatagaggg cgaatttaac acagtgttgc 1321 tggcggtagg aagagattct tgtacgagaa ctattggctt agagaccgtg ggcgtgaaga 1381 taaacgaaaa aaccggaaag atacccgtca cggatgaaga gcagaccaat gtgccttaca 1441 tctacgccat cggtgacatc ctggagggga agctagagct gactcccgta gccatccagg 1501 cggggagatt gctggctcag aggctgtatg gaggctccaa tgtcaaatgt gactatgaca 1561 atgtcccaac gactgtattt actcctttgg aatatggctg ttgtggcctc tctgaagaaa 1621 aagccgtaga gaaatttggg gaagaaaata ttgaagttta ccatagtttc ttttggccat 1681 tggaatggac agtcccatcc cgggataaca acaaatgtta tgcaaaaata atctgcaacc 1741 ttaaagacga tgaacgtgtc gtgggcttcc acgtgctggg tccaaacgct ggagaggtga 1801 cgcagggctt tgcggctgcg ctcaagtgtg ggctgactaa gcagcagctg gacagcacca 1861 tcggcatcca cccggtctgt gcagagatat tcacaacgtt gtcagtgacg aagcgctctg 1921 ggggagacat cctccagtct ggctgctgag gttaagcccc agtgtggatg ctgttgccaa 1981 gactacagac cattgccttg cttccttgcc cacgcccagg tgaagttcag gaaggctctt 2041 gggtcctagg cgccaattca aggtgctgtc ctaaggccac cgggtccctg ggatcttgtg 2101 ggtaggaggt ggcaggtcga aggaggctgc agcatcgcac tggggtcacc atgacagact 2161 cagactgaca tctggcagag catcacaggc atgcgtccat gaagtcactg gcctcaagcc 2221 caagtggtgg gcagtgacag aagagctgcc gggtctgttg agctcaacct tttcctgtag 2281 attgtcttag tctcactttc aagctgtcta atgtcaattc tgttttttctt ttttcctcca 2341 tggggttaat gatactagag atagggaata ttagcaatca gttttttgtca tggctggtcc 2401 atctgcaaca gtctttactg tgtggaagtg ggtgagatgg cttatgagag ccaaaccaat 2461 ttatccccag aaagacgaat taccctgtga ctaaaataca ctgtctgctt ttactaactg 2521 gtgtagcatt gtctcctttta ataagtcttg tgtccaaaac gagaaaaacc attggccact 2581 tttgcaagtt tcctgcagtg tgcttagcaa gggaggtggc gacttggcta atctacttga 2641 actgcatcgc atggctcttg ggtagcttag agcatcgcag ggtagaggca gaccagcagt 2701 gagtgtctct cctggtacaa ttattgtctg gttctcagtg gaaaacgctt aatttgcttt 2761 aaacttggtg tttttgtgag gtggatttag tcttaagctg tgtcccataa gaactacatt 2821 cacaggcaag tggctcttcc tccacacagc ctatacatct tctgaggtaa ttactttcat 2881 aaggaagctg ttcataacgt aagttattat tattattgaa cacaggtgga tgtgaaggat 2941 ttttcattga aaaaccaaat ggttttttctt tttttctgtt cagtgagccc acaggaactc
```

-continued

```
3001 tgtcaggaca gccagtactc tgccggcatg gctgctgggg cgtttacggt gtagtttagc 3061 tcctaggtta catgaccgtg aacatgctgg ctgaggacta cacaaaccag gtttcccacc 3121 atacacggcc tggccctgca gcttcttttc ttgccctccc ctttgcctgt ccccacctgc 3181 agtactgagt ggcgtttcac agtacccttc tgggccacct cagggaaggg atttgcctgg 3241 tgtccagcca gcagcaccca ccctgcccca cgaggctccc tcacacctgc ccccccgtcc 3301 ttgtgttgaa gacagtggga agaggagaaa ggaccaggga aaccaaggga gttgactgtt 3361 cagttttatt tatttatttt ttaagttttt ttttcctttc aagtctgcca gtctctgaga 3421 tcagaacaac agacagtgta gggtaactaa tcatgtgatt ctcttagtgg aatgaaatgt 3481 tctacccca caagaaggag tatacgtcat tgttcatatt ctgtaatcgc acaatgtatt 3541 gtaatgcaaa ttccaattcc atgtattttt attacaattt ttctggaaaa aaatgtgaac 3601 caataaaaga tgttgatgca cacgcgtgcc ttct
```

(i.e., TXNRD1 mRNA isoforms), thereby reducing or inhibiting TXNRD1 expression. The antisense nucleic acid may be antisense RNA, or antisense DNA. Antisense nucleic acids based on the known TXNRD1 gene sequence can be readily designed and engineered using methods known in the art. In some embodiments, the antisense nucleic acid comprises the nucleic acid sequence of any one of SEQ ID NOs: 1-12, or a complement thereof.

Antisense nucleic acids are molecules which are complementary to a sense nucleic acid strand, e.g., complementary to the coding strand of a double-stranded DNA molecule (or cDNA) or complementary to an mRNA sequence. Accordingly, an antisense nucleic acid can form hydrogen bonds with a sense nucleic acid. The antisense nucleic acid can be complementary to an entire TXNRD1 coding strand, or to a portion thereof, e.g., all or part of the protein coding region (or open reading frame). In some embodiments, the antisense nucleic acid is an oligonucleotide which is complementary to only a portion of the coding region of TXNRD1 mRNA. In certain embodiments, an antisense nucleic acid molecule can be complementary to a noncoding region of the TXNRD1 coding strand. In some embodiments, the noncoding region refers to the 5' and 3' untranslated regions that flank the coding region and are not translated into amino acids. For example, the antisense oligonucleotide can be complementary to the region surrounding the translation start site of TXNRD1. An antisense oligonucleotide can be, for example, about 5, 10, 15, 20, 25, 30, 35, 40, 45 or 50 nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or modified nucleotides designed to increase the biological stability of the molecules or to increase the physical stability of the duplex formed between the antisense and sense nucleic acids, e.g., phosphorothioate derivatives and acridine substituted nucleotides. Examples of modified nucleotides which can be used to generate the antisense nucleic acid include 5-fluorouracil, 5-bromouracil, 5-chlorouracil, 5-hodouracil, hypoxanthine, xanthine, 4-acetylcytosine, 5-(carboxyhydroxylmethyl)uracil, 5-carboxymethylaminomethyl-2-thouridine, 5-carboxymethylaminometh-yluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-metnylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopenten-yladenine, uracil-5-oxyacetic acid (v), wybutosine, pseudouracil, queosine, 2-thiocytosine, 5-methyl-2-thiouracil, 2-thlouracil, 4-thiouracil, 5-methyluracil, uracil-5-oxyacetic acid methylester, uracil-5-cxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules may be administered to a subject or generated in situ such that they hybridize with or bind to cellular mRNA and/or genomic DNA encoding the protein of interest to thereby inhibit expression of the protein, e.g., by inhibiting transcription and/or translation. The hybridization can occur via Watson-Crick base pairing to form a stable duplex, or in the case of an antisense nucleic acid molecule which binds to DNA duplexes, through specific interactions in the major groove of the double helix.

In some embodiments, the antisense nucleic acid molecules are modified such that they specifically bind to receptors or antigens expressed on a selected cell surface, e.g., by linking the antisense nucleic acid molecules to peptides or antibodies which bind to cell surface receptors or antigens. In some embodiments, the antisense nucleic acid molecule is an alpha-anomeric nucleic acid molecule. An alpha-anomeric nucleic acid molecule forms specific double-stranded hybrids with complementary RNA in which, contrary to the usual β-units, the strands run parallel to each other (Gaultier et al., *Nucleic Acids. Res.* 15:6625-6641(1987)). The antisense nucleic acid molecule can also comprise a 2'-O-methylribonucleotide (Inoue et al., *Nucleic Acids Res.* 15:6131-6148 (1987)) or a chimeric RNA-DNA analogue (Inoue et al., *FEBS Lett.* 215:327-330 (1987)).

The present disclosure also provides a short hairpin RNA (shRNA) or small interfering RNA (siRNA) comprising a nucleic acid sequence that is complementary to and specifically hybridizes with a portion of any one of SEQ ID NOs:

13-23 (TXNRD1 mRNA isoforms), thereby reducing or inhibiting TXNRD1 expression. In some embodiments, the shRNA or siRNA is about 18, 19, 20, 21, 22, 23, 24, 25, 26, 27, 28 or 29 base pairs in length. Double-stranded RNA (dsRNA) can induce sequence-specific post-transcriptional gene silencing (e.g., RNA interference (RNAi)) in many organisms such as *C. elegans, Drosophila*, plants, mammals, oocytes and early embryos. RNAi is a process that interferes with or significantly reduces the number of protein copies made by an mRNA. For example, a double-stranded siRNA or shRNA molecule is engineered to complement and hybridize to a mRNA of a target gene. Following intracellular delivery, the siRNA or shRNA molecule associates with an RNA-induced silencing complex (RISC), which then binds and degrades a complementary target mRNA (such as TXNRD1 mRNA). In some embodiments, the shRNA or siRNA comprises the nucleic acid sequence of any one of SEQ ID NOs: 1-12.

The present disclosure also provides a ribozyme comprising a nucleic acid sequence that is complementary to and specifically hybridizes with a portion of any one of SEQ ID NOs: 13-23 (TXNRD1 mRNA isoforms), thereby reducing or inhibiting TXNRD1 expression. Ribozymes are catalytic RNA molecules with ribonuclease activity which are capable of cleaving a complementary single-stranded nucleic acid, such as an mRNA. Thus, ribozymes (e.g., hammerhead ribozymes (described in Haselhoff and Gerlach, *Nature* 334:585-591 (1988))) can be used to catalytically cleave TXNRD1 transcripts, thereby inhibiting translation of TXNRD1.

A ribozyme having specificity for a TXNRD1-encoding nucleic acid can be designed based upon a TXNRD1 nucleic acid sequence disclosed herein. For example, a derivative of a Tetrahymena L-19 IVS RNA can be constructed in which the nucleotide sequence of the active site is complementary to the nucleotide sequence to be cleaved in a TXNRD1-encoding mRNA. See, e.g., U.S. Pat. Nos. 4,987,071 and 5,116,742. Alternatively, TXNRD1 mRNA can be used to select a catalytic RNA having a specific ribonuclease activity from a pool of RNA molecules. See, e.g., Bartel and Szostak (1993) *Science* 261:1411-1418, incorporated herein by reference.

The present disclosure also provides a synthetic guide RNA (sgRNA) comprising a nucleic acid sequence that is complementary to and specifically hybridizes with a portion of any one of SEQ ID NOs: 13-23 (TXNRD1 mRNA isoforms). Guide RNAs for use in CRISPR-Cas systems are typically generated as a single guide RNA comprising a crRNA segment and a tracrRNA segment. The crRNA segment and a tracrRNA segment can also be generated as separate RNA molecules. The crRNA segment comprises the targeting sequence that binds to a portion of any one of SEQ ID NOs: 13-23 (TXNRD1 mRNA isoforms), and a stem portion that hybridizes to a tracrRNA. The tracrRNA segment comprises a nucleotide sequence that is partially or completely complementary to the stem sequence of the crRNA and a nucleotide sequence that binds to the CRISPR enzyme. In some embodiments, the crRNA segment and the tracrRNA segment are provided as a single guide RNA. In some embodiments, the crRNA segment and the tracrRNA segment are provided as separate RNAs. The combination of the CRISPR enzyme with the crRNA and tracrRNA make up a functional CRISPR-Cas system. Exemplary CRISPR-Cas systems for targeting nucleic acids, are described, for example, in WO2015/089465.

In some embodiments, a synthetic guide RNA is a single RNA represented as comprising the following elements:

5'-X1-X2-Y-Z-3' where X1 and X2 represent the crRNA segment, where X1 is the targeting sequence that binds to a portion of any one of SEQ ID NOs: 13-23, X2 is a stem sequence the hybridizes to a tracrRNA, Z represents a tracrRNA segment comprising a nucleotide sequence that is partially or completely complementary to X2, and Y represents a linker sequence. In some embodiments, the linker sequence comprises two or more nucleotides and links the crRNA and tracrRNA segments. In some embodiments, the linker sequence comprises 2, 3, 4, 5, 6, 7, 8, 9, 10 or more nucleotides. In some embodiments, the linker is the loop of the hairpin structure formed when the stem sequence hybridized with the tracrRNA.

In some embodiments, a synthetic guide RNA is provided as two separate RNAs where one RNA represents a crRNA segment: 5'-X1-X2-3' where X1 is the targeting sequence that binds to a portion of any one of SEQ ID NOs: 13-23, X2 is a stem sequence the hybridizes to a tracrRNA, and one RNA represents a tracrRNA segment, Z, that is a separate RNA from the crRNA segment and comprises a nucleotide sequence that is partially or completely complementary to X2 of the crRNA.

Exemplary crRNA stem sequences and tracrRNA sequences are provided, for example, in WO/2015/089465, which is incorporated by reference herein. In general, a stem sequence includes any sequence that has sufficient complementarity with a complementary sequence in the tracrRNA to promote formation of a CRISPR complex at a target sequence, wherein the CRISPR complex comprises the stem sequence hybridized to the tracrRNA. In general, degree of complementarity is with reference to the optimal alignment of the stem and complementary sequence in the tracrRNA, along the length of the shorter of the two sequences. Optimal alignment may be determined by any suitable alignment algorithm, and may further account for secondary structures, such as self-complementarity within either the stem sequence or the complementary sequence in the tracrRNA. In some embodiments, the degree of complementarity between the stem sequence and the complementary sequence in the tracrRNA along the length of the shorter of the two when optimally aligned is about or more than about 25%, 30%, 40%, 50%, 60%, 70%, 80%, 90%, 95%, 97.5%, 99%, or higher. In some embodiments, the stem sequence is about or more than about 5, 6, 7, 8, 9, 10, 11, 12, 13, 14, 15, 16, 17, 18, 19, 20, 25, 30, 40, 50, or more nucleotides in length. In some embodiments, the stem sequence and complementary sequence in the tracrRNA are contained within a single RNA, such that hybridization between the two produces a transcript having a secondary structure, such as a hairpin. In some embodiments, the tracrRNA has additional complementary sequences that form hairpins. In some embodiments, the tracrRNA has at least two or more hairpins. In some embodiments, the tracrRNA has two, three, four or five hairpins. In some embodiments, the tracrRNA has at most five hairpins.

In a hairpin structure, the portion of the sequence 5' of the final "N" and upstream of the loop corresponds to the crRNA stem sequence, and the portion of the sequence 3' of the loop corresponds to the tracrRNA sequence. Further non-limiting examples of single polynucleotides comprising a guide sequence, a stem sequence, and a tracr sequence are as follows (listed 5' to 3'), where "N" represents a base of a guide sequence (e.g. a modified oligonucleotide provided herein), the first block of lower case letters represent stem sequence, and the second block of lower case letters represent the tracrRNA sequence, and the final poly-T sequence represents the transcription terminator: (a) NNNNNNNNNNNNNNNNNNNNgttttttgtactctcaagatttaGAAAtaaatcttgcagaagctacaaagataa ggcttcatgccgaaat-caacaccctgtcattttatggcagggtgttttcgttatttaaTTTTTT (SEQ ID NO: 24); (b) NNNNNNNNNNNNNNNNN-NNNNgttttgtactctcaGAAAtgcagaagctacaaagataaggctt-catgccg aaatcaacaccctgtcattttatggcagggtgttttcgttatttaaT-TTTTT (SEQ ID NO: 25); (c) NNNNNNNNNNNNNNNNNNNNNNgttttgtactctcaG-AAAtgcagaagctacaaagataaggcttcatgccg aaatcaacaccctgtcat-tttatggcagggtgtTTTTTT (SEQ ID NO: 26); (d) NNNNNNNNNNNNNNNNNNNNNgttt-tagagctaGAAAtagcaagttaaaataaggctagtccgttatcaactt gaaaaagtggcaccgagtcggtgcTTTTTT (SEQ ID NO: 27); (e) NNNNNNNNNNNNNNNNNNNNNgttt-tagagctaGAAATAGcaagttaaaataaggctagtccgttatcaac ttgaaaaagtgTTTTTTT (SEQ ID NO: 28); and (f) NNNNNNNNNNNNNNNNNNNNNgttt-tagagctagAAATAGcaagttaaaataaggctagtccgttatcaTT TTTTTT (SEQ ID NO: 29).

Selection of suitable oligonucleotides for use in as a targeting sequence in a CRISPR Cas system depends on several factors including the particular CRISPR enzyme to be used and the presence of corresponding proto-spacer adjacent motifs (PAMs) downstream of the target sequence in the target nucleic acid. The PAM sequences direct the cleavage of the target nucleic acid by the CRISPR enzyme. In some embodiments, a suitable PAM is 5'-NRG or 5'-NN-GRR (where N is any Nucleotide) for SpCas9 or SaCas9 enzymes (or derived enzymes), respectively. Generally, the PAM sequences should be present between about 1 to about 10 nucleotides of the target sequence to generate efficient cleavage of the target nucleic acid. Thus, when the guide RNA forms a complex with the CRISPR enzyme, the complex locates the target and PAM sequence, unwinds the DNA duplex, and the guide RNA anneals to the complementary sequence on the opposite strand. This enables the Cas9 nuclease to create a double-strand break. In some embodiments, the sgRNA comprises the nucleic acid sequence of any one of SEQ ID NOs: 1-12.

A variety of CRISPR enzymes are available for use in conjunction with the disclosed guide RNAs of the present disclosure. In some embodiments, the CRISPR enzyme is a Type II CRISPR enzyme. In some embodiments, the CRISPR enzyme catalyzes DNA cleavage. In some embodiments, the CRISPR enzyme catalyzes RNA cleavage. In some embodiments, the CRISPR enzyme is any Cas9 protein, for instance any naturally-occurring bacterial Cas9 as well as any chimeras, mutants, homologs or orthologs. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified variants thereof. In some embodiments, the CRISPR enzyme cleaves both strands of the target nucleic acid at the Protospacer Adjacent Motif (PAM) site. In some embodiments, the CRISPR enzyme is a nickase, which cleaves only one strand of the target nucleic acid. In some embodiments, the CRISPR enzyme is a dCas9 tagged with additional enzyme activities, which suppress or activate the expression of genes of interest.

Pharmaceutical Compositions

In one aspect, the present disclosure provides pharmaceutical compositions comprising a TXNRD1 inhibitor.

The pharmaceutical compositions of the present disclosure may be prepared by any of the methods known in the pharmaceutical arts. The amount of active ingredient that can be combined with a carrier material to produce a single dosage form will vary depending upon the host being treated and the particular mode of administration. The amount of active ingredient that can be combined with a carrier material to produce a single dosage form will generally be that amount of the compound that produces a therapeutic effect. Generally, the amount of active compound will be in the range of about 0.1 to 99 percent, more typically, about 5 to 70 percent, and more typically, about 10 to 30 percent.

In some embodiments, pharmaceutical compositions of the present technology may contain one or more pharmaceutically-acceptable carriers, which as used herein, generally refers to a pharmaceutically-acceptable composition, such as a liquid or solid filler, diluent, excipient, manufacturing aid (e.g., lubricant, talc magnesium, calcium or zinc stearate, or steric acid), or solvent encapsulating material, useful for introducing the active agent into the body.

Examples of suitable aqueous and non-aqueous carriers that may be employed in the pharmaceutical compositions of the present technology include, for example, water, ethanol, polyols (such as glycerol, propylene glycol, polyethylene glycol, and the like), vegetable oils (such as olive oil), and injectable organic esters (such as ethyl oleate), and suitable mixtures thereof. Proper fluidity can be maintained, for example, by the use of coating materials, such as lecithin, by the maintenance of the required particle size in the case of dispersions, and by the use of surfactants.

In some embodiments, the formulations may include one or more of sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; alginic acid; buffering agents, such as magnesium hydroxide and aluminum hydroxide; pyrogen-free water; isotonic saline; Ringer's solution; ethyl alcohol; pH buffered solutions; polyesters, polycarbonates and/or polyanhydrides; preservatives; glidants; fillers; and other non-toxic compatible substances employed in pharmaceutical formulations.

Various auxiliary agents, such as wetting agents, emulsifiers, lubricants (e.g., sodium lauryl sulfate and magnesium stearate), coloring agents, release agents, coating agents, sweetening agents, flavoring agents, preservative agents, and antioxidants can also be included in the pharmaceutical composition of the present technology. Some examples of pharmaceutically-acceptable antioxidants include: water soluble antioxidants, such as ascorbic acid, cysteine hydrochloride, sodium bisulfate, sodium metabisulfite, sodium sulfite, and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like. In some embodiments, the pharmaceutical formulation includes an excipient selected from, for example, celluloses, liposomes, lipid nanoparticles, micelle-forming agents (e.g., bile acids), and polymeric carriers, e.g., polyesters and polyanhydrides. Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof. Prevention of the action of microorganisms on the active compounds may be ensured by the inclusion of various antibacterial and antifungal agents, such as, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption, such as aluminum monostearate and gelatin.

Therapeutic Methods

The following discussion is presented by way of example only, and is not intended to be limiting.

One aspect of the present technology includes methods of treating a disease or condition characterized by elevated expression levels and/or increased activity of TXNRD1. Additionally or alternatively, in some embodiments, the present technology includes methods of treating a RAS-mutant cancer. The three major isoforms of RAS (KRAS, NRAS, and HRAS) together are mutated in about 20% of human cancers, primarily in the active site at residues G12, G13, and Q61 near the g-phosphate of the guanosine triphosphate (GTP) substrate (See Marcus & Mattos, *Clin Cancer Res* 21(8): 1810-1818 (2015)). In certain embodiments, the RAS-mutant cancer comprises a KRAS, NRAS, or HRAS mutation selected from the group consisting of G12C, G12D, G12V, G12A, G12S, G12R, G13D, G13C, G13S, G13R, G13A, G13V, Q61H, Q61L, Q61R, Q61K, Q61P, and Q61E.

In some embodiments, the present technology includes methods of treating a RAS-mutant pancreatic cancer. In one aspect, the present disclosure provides a method for inhibiting proliferation of a RAS-mutant cancer in a subject in need thereof, comprising administering to the subject a therapeutically effective amount of at least one TXNRD1 inhibitor disclosed herein, and wherein the subject suffers from a RAS-mutant cancer characterized by elevated expression levels and/or increased activity of TXNRD1.

In some embodiments, the subject is diagnosed as having, suspected as having, or at risk of having a disease or condition characterized by elevated expression levels and/or increased activity of TXNRD1. Additionally or alternatively, in some embodiments, the subject is diagnosed as having a RAS-mutant cancer. In certain embodiments, the RAS-mutant cancer comprises a KRAS, NRAS, or HRAS mutation selected from the group consisting of G12C, G12D, G12V, G12A, G12S, G12R, G13D, G13C, G13S, G13R, G13A, G13V, Q61H, Q61L, Q61R, Q61K, Q61P, and Q61E. In some embodiments, the subject is diagnosed as having lung cancer (e.g., lung adenocarcinoma), mucinous adenoma, pancreatic cancer (e.g., PDAC), colorectal cancer, skin cancer (e.g., melanoma), endometrial cancer, testicular germ cell cancer, or adrenal gland cancer. In some embodiments, the subject is diagnosed as having pancreatic cancer. In some embodiments, the subject is diagnosed as having a RAS-mutant pancreatic cancer.

In therapeutic applications, compositions or medicaments comprising a TXNRD1 inhibitor disclosed herein are administered to a subject suspected of, or already suffering from such a disease or condition (such as, a subject diagnosed with a disease or condition characterized by elevated expression levels and/or increased activity of TXNRD1 and/or a subject diagnosed with a RAS-mutant cancer and/or a subject diagnosed with pancreatic cancer), in an amount sufficient to cure, or at least partially arrest, the symptoms of the disease, including its complications and intermediate pathological phenotypes in development of the disease.

Subjects suffering from a disease or condition characterized by elevated expression levels and/or increased activity of TXNRD1 and/or a subject diagnosed with a RAS-mutant cancer can be identified by any or a combination of diagnostic or prognostic assays known in the art.

In some embodiments, the subject may exhibit one or more mutations in KRAS. In addition, the subject may exhibit one or more mutations in at least one of TP53, CDKN2A, SMAD4, MLL3, TGFBR2, ARID1A and SF3B1, EPC1 and ARID2, ATM, ZIM2, MAP2K4, NALCN, SLC16A4, MAGEA6, ROBO2, KDM6A, PREX2, ERBB2, MET, FGFR1, CDK6, PIK3R3, PIK3CA, BRCA1, BRCA2, PALB2, etc. Biankin et al., *Nature* 491(7424): 399-405 (2012); and Waddell et al., *Nature* 518(7540):495-501 (2015). Additionally or alternatively, the subject may exhibit at least one mutation in one or more of a core set of twelve cellular signaling pathways and processes. Jones et al., *Science* 321(5897): 1801-1806 (2008).

In some embodiments, subjects with a disease or condition characterized by elevated expression levels and/or increased activity of TXNRD1, and/or subjects suffering from a RAS-mutant pancreatic cancer that are treated with the TXNRD1 inhibitor will show amelioration or elimination of one or more of the following symptoms: pain in the upper abdomen that radiates towards the back, loss of appetite or unintended weight loss, depression, new-onset diabetes, blood clots, fatigue, yellowing of skin and the whites of eyes (jaundice), bloating, nausea, and vomiting.

In certain embodiments, subjects with a disease or condition characterized by elevated expression levels of TXNRD1 and/or increased activity levels of TXNRD1, and/or subjects suffering from a RAS-mutant cancer, and/or subjects suffering from pancreatic cancer that are treated with the TXNRD1 inhibitor will show reduced RAS-mutant cell proliferation and/or increased survival compared to untreated subjects with RAS-mutant cancer. In certain embodiments, subjects with a disease or condition characterized by elevated expression levels of TXNDR1 and/or increased activity of TXNRD1, and/or subjects suffering from a RAS-mutant cancer, and/or subjects suffering from pancreatic cancer that are treated with the TXNRD1 inhibitor will show reduced TXNRD1 and/or RAS expression levels and/or reduced TXNRD1 and/or RAS activity levels compared to untreated subjects with RAS-mutant cancer.

In one aspect, the present disclosure provides a method for monitoring the therapeutic efficacy of a TXNRD1 inhibitor in a subject diagnosed with a RAS-mutant cancer comprising: (a) detecting TXNRD1 protein levels in a test sample obtained from the subject after the subject has been administered the TXNRD1 inhibitor; and (b) determining that the TXNRD1 inhibitor is effective when the TXNRD1 protein levels in the test sample are reduced compared to that observed in a control sample obtained from the subject prior to administration of the TXNRD1 inhibitor. The TXNRD1 inhibitor may be auranofin, Piperlongumine, D9, TRi-1, TRi-2, Myricetin, PMX464, PX12, Brevetoxin-2, Manumycin A, Ethaselen, Aurothioglucose, Protoporphyrin IX, inhibitory RNAs against TXNRD1, anti-TXNRD1 antibodies, or any derivatives thereof. The test sample may be tissues, cells or biological fluids (blood, plasma, saliva, urine, serum etc.) present within a subject. Alternatively, RAS (e.g., KRAS, HRAS, NRAS) and/or TXARD1 expression levels may be used to determine the efficacy of the TXNRD1 inhibitor in the subject (see Example 6 described herein). Accordingly, in certain embodiments, the method further comprises detecting expression levels of RAS (e.g., KRAS, HRAS, NRAS) and/or TXNRD1 in the subject, wherein a decrease in RAS (e.g., KRAS, HRAS, NRAS) and/or TXARD1 expression levels relative to those observed in the subject prior to treatment is indicative of the thera- peutic efficacy of the TXNRD1 inhibitor. Additionally or alternatively, in certain embodiments, the method further comprises detecting activity of RAS (e.g., KRAS, HRAS, NRAS) and/or TXNRD1 protein in the subject, wherein a decrease in RAS (e.g., KRAS, HRAS, NRAS) and/or TXNRD1 activity relative to those observed in the subject prior to treatment is indicative of the therapeutic efficacy of the TXNRD1 inhibitor. In certain embodiments, the RAS-mutant cancer comprises a KRAS, NRAS, or HRAS muta- tion selected from the group consisting of G12C, G12D, G12V, G12A, G12S, G12R, G13D, G13C, G13S, G13R, G13A, G13V, Q61H, Q61L, Q61R, Q61K, Q61P, and Q61E. In certain embodiments, the KRAS, NRAS, or HRAS muta- tion is detected via DNA sequencing.

In any and all embodiments of the methods disclosed herein, TXNRD1 and/or RAS (e.g., KRAS, HRAS, NRAS) expression levels are detected via RNA-seq, northern blot- ting, microarrays, dot or slot blots, fluorescent in situ hybrid- ization, Reverse transcription polymerase chain reaction (RT-PCR), ribonuclease protection assay (RPA), real-time quantitative RT-PCR, high-performance liquid chromatog- raphy (HPLC), liquid chromatography-mass spectrometry (LC/MS), enzyme-linked immunosorbent assay (ELISA), immunoprecipitation, immunoelectrophoresis, immunos- taining, immunohistochemistry, or western blotting.

Prophylactic Methods

In one aspect, the present technology provides a method for preventing or delaying the onset of a disease or condition characterized by elevated expression levels and/or increased activity of TXNRD1. Additionally or alternatively, in some aspects, the present technology provides a method for pre- venting or delaying the onset a RAS-mutant cancer. In certain embodiments, the RAS-mutant cancer comprises a KRAS, NRAS, or HRAS mutation selected from the group consisting of G12C, G12D, G12V, G12A, G12S, G12R, G13D, G13C, G13S, G13R, G13A, G13V, Q61H, Q61L, Q61R, Q61K, Q61P, and Q61E. The RAS-mutant cancer may be lung cancer (e.g., lung adenocarcinoma), mucinous adenoma, pancreatic cancer (e.g., PDAC), colorectal cancer, skin cancer (e.g., melanoma), endometrial cancer, testicular germ cell cancer, or adrenal gland cancer.

Subjects at risk or susceptible to a disease or condition characterized by elevated expression levels and/or increased activity of TXNRD1, and/or subjects at risk or susceptible to a RAS-mutant cancer, and/or subjects at risk or susceptible to pancreatic cancer include those that exhibit one or more mutations in RAS (e.g., KRAS, HRAS, NRAS). In addition, the subjects may exhibit one or more point mutations in one or more of TP53, CDKN2A, SMAD4, MLL3, TGFBR2, ARID1A and SF3B1, EPC1 and ARID2, ATM, ZIM2, MAP2K4, NALCN, SLC16A4, MAGEA6, ROBO2, KDM6A, PREX2, ERBB2, MET, FGFR1, CDK6, PIK3R3, PIK3CA, BRCA1, BRCA2, PALB2, etc. Biankin et al., *Nature* 491(7424): 399-405 (2012); and Waddell et al., *Nature* 518(7540):495-501 (2015). Additionally or alterna- tively, the subjects may exhibit at least one mutation in one or more of a core set of twelve cellular signaling pathways and processes. Jones et al., *Science* 321(5897): 1801-1806 (2008). Such subjects can be identified by, e.g., any or a combination of diagnostic or prognostic assays known in the art. In certain embodiments, the RAS-mutant cancer com- prises a KRAS, NRAS, or HRAS mutation selected from the group consisting of G12C, G12D, G12V, G12A, G12S, G12R, G13D, G13C, G13S, G13R, G13A, G13V, Q61H, Q61L, Q61R, Q61K, Q61P, and Q61E.

In prophylactic applications, pharmaceutical composi- tions or medicaments comprising a TXNRD1 inhibitor dis- closed herein are administered to a subject susceptible to, or otherwise at risk of a disease or condition characterized by (a) elevated expression levels and/or increased activity of TXNRD1, and/or (b) a subject susceptible to, or otherwise at risk of a RAS-mutant cancer, and/or a subject susceptible to, or otherwise at risk of pancreatic cancer, in an amount sufficient to eliminate or reduce the risk, or delay the onset of the disease, including biochemical, histologic and/or behavioral symptoms of the disease, its complications and intermediate pathological phenotypes presenting during development of the disease. Administration of a prophylac- tic TXNRD1 inhibitor can occur prior to the manifestation of symptoms characteristic of the disease or disorder, such that the disease or disorder is prevented or, alternatively, delayed in its progression.

In some embodiments, treatment with the TXNRD1 inhibitor will prevent or delay the onset of one or more of the following symptoms: pain in the upper abdomen that radi- ates towards the back, loss of appetite or unintended weight loss, depression, new-onset diabetes, blood clots, fatigue, yellowing of skin and the whites of eyes (jaundice), bloat- ing, nausea, and vomiting. In certain embodiments, (a) subjects with a disease or condition characterized by elevated expression levels and/or increased activity of TXNRD1, and/or (b) subjects with a RAS-mutant cancer, and/or subjects with pancreatic cancer that are treated with the TXNRD1 inhibitor will show TXNRD1 and/or RAS expression levels that resemble those observed in healthy control subjects.

For therapeutic and/or prophylactic applications, a com- position comprising a TXNRD1 inhibitor disclosed herein, is administered to the subject. In some embodiments, the TXNRD1 inhibitor is administered one, two, three, four, or five times per day. In some embodiments, the TXNRD1 inhibitor is administered more than five times per day. Additionally or alternatively, in some embodiments, the TXNRD1 inhibitor is administered every day, every other day, every third day, every fourth day, every fifth day, or every sixth day. In some embodiments, the TXNRD1 inhibi- tor is administered weekly, bi-weekly, tri-weekly, or monthly. In some embodiments, the TXNRD1 inhibitor is administered for a period of one, two, three, four, or five weeks. In some embodiments, the TXNRD1 inhibitor is administered for six weeks or more. In some embodiments, the TXNRD1 inhibitor is administered for twelve weeks or more. In some embodiments, the TXNRD1 inhibitor is administered for a period of less than one year. In some embodiments, the TXNRD1 inhibitor is administered for a period of more than one year. In some embodiments, the TXNRD1 inhibitor is administered throughout the subject's life.

In some embodiments of the methods of the present technology, the TXNRD1 inhibitor is administered daily for 1 week or more. In some embodiments of the methods of the present technology, the TXNRD1 inhibitor is administered daily for 2 weeks or more. In some embodiments of the methods of the present technology, the TXNRD1 inhibitor is administered daily for 3 weeks or more. In some embodi- ments of the methods of the present technology, the TXNRD1 inhibitor is administered daily for 4 weeks or more. In some embodiments of the methods of the present technology, the TXNRD1 inhibitor is administered daily for 6 weeks or more. In some embodiments of the methods of the present technology, the TXNRD1 inhibitor is administered daily for 12 weeks or more. In some embodiments, the TXNRD1 inhibitor is administered daily throughout the subject's life.

Determination of the Biological Effect of TXNRD1 Inhibitor

In various embodiments, suitable in vitro or in vivo assays are performed to determine the effect of a specific TXNRD1 inhibitor and whether its administration is indicated for treatment. In various embodiments, in vitro assays can be performed with representative animal models, to determine if a given TXNRD1 inhibitor exerts the desired effect on reducing or eliminating signs and/or symptoms of a RAS-mutant cancer. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects. In some embodiments, in vitro or in vivo testing is directed to the biological function of one or more TXNDR1 inhibitors of the present technology.

Animal models of a RAS-mutant cancer, and/or pancreatic cancer may be generated using techniques known in the art (see Example 7 described herein). Such models may be used to demonstrate the biological effect of TXNRD1 inhibitors in the prevention and treatment of conditions arising from disruption of a particular gene, and/or inhibition of activity of a specific protein and for determining what comprises a therapeutically effective amount of the one or more TXNRD1 inhibitors disclosed herein in a given context.

Modes of Administration and Effective Dosages

Any method known to those in the art for contacting a cell, organ or tissue with one or more TXNRD1 inhibitors disclosed herein may be employed. Suitable methods include in vitro, ex vivo, or in vivo methods. In vivo methods typically include the administration of one or more TXNRD1 inhibitors to a mammal, suitably a human. When used in vivo for therapy, the one or more TXNRD1 inhibitors described herein are administered to the subject in effective amounts (i.e., amounts that have desired therapeutic effect). The dose and dosage regimen will depend upon the degree of the disease state of the subject, the characteristics of the particular TXNRD1 inhibitor used, e.g., its therapeutic index, and the subject's history.

The effective amount may be determined during preclinical trials and clinical trials by methods familiar to physicians and clinicians. An effective amount of one or more TXNRD1 inhibitors useful in the methods may be administered to a mammal in need thereof by any of a number of well-known methods for administering pharmaceutical compounds. The TXNRD1 inhibitor may be administered systemically or locally.

The one or more TXNRD1 inhibitors described herein can be incorporated into pharmaceutical compositions for administration, singly or in combination, to a subject for the treatment or prevention of a RAS-mutant cancer, and/or a subject for the treatment or prevention of pancreatic cancer. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The pharmaceutical compositions having one or more TXNRD1 inhibitors disclosed herein can include a carrier, which can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A therapeutic agent can be formulated in a carrier system. The carrier can be a colloidal system. The colloidal system can be a liposome, a phospholipid bilayer vehicle, or a lipid nanoparticle. In one embodiment, the therapeutic agent is encapsulated in a liposome while maintaining the agent's structural integrity. One skilled in the art would appreciate that there are a variety of methods to prepare liposomes. (See Lichtenberg, et al., *Methods Biochem. Anal.*, 33:337-462 (1988); Anselem, et al., *Liposome Technology*, CRC Press (1993)). Liposomal formulations can delay clearance and increase cellular uptake (See Reddy, *Ann. Pharmacother.*, 34(7-8):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic agent can be embedded in the polymer matrix, while maintaining the agent's structural integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, ChemicalBiology, 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods*, 4(3): 201-9 (1994); and Gregoriadis, "Engineering Liposomes for Drug Delivery: Progress and Problems," *Trends Biotechnol.*, 13(12):527-37 (1995). Mizguchi, et al., *Cancer Lett.*, 100: 63-69 (1996), describes the use of fusogenic liposomes to deliver a protein to cells both in vivo and in vitro.

Dosage, toxicity and therapeutic efficacy of any therapeutic agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of the one or more TXNRD1 inhibitors disclosed herein sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example, dosages can be 1 mg/kg body weight or 10 mg/kg body weight every day, every two days or every three days or within the range of 1-10 mg/kg every week, every two weeks or every three weeks. In one embodiment, a single dosage of the therapeutic compound ranges from 0.001-10,000 micrograms per kg body weight. In one embodiment, one or more TXNRD1 inhibitor concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In some embodiments, a therapeutically effective amount of one or more TXNRD1 inhibitors may be defined as a concentration of inhibitor at the target tissue of $10^{-32}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the present methods can be any mammal, including, for example, farm animals, such as sheep, pigs, cows, and horses; pet animals, such as dogs and cats; laboratory animals, such as rats, mice and rabbits. In some embodiments, the mammal is a human.

Combination Therapy

In some embodiments, one or more of the TXNRD1 inhibitors disclosed herein may be combined with one or more additional therapies for the prevention or treatment of a RAS-mutant cancer or pancreatic cancer. Additional therapeutic agents include, but are not limited to, ABRAXANE® (albumin-bound paclitaxel), GEMZAR® (gemcitabine), 5-FU (fluorouracil), ONIVYDE® (irinotecan liposome injection), surgery, radiation, or a combination thereof.

In some embodiments, the one or more TXNRD1 inhibitors disclosed herein may be separately, sequentially or simultaneously administered with at least one additional therapeutic agent selected from the group consisting of immunotherapeutic agents, alkylating agents, topoisomerase inhibitors, endoplasmic reticulum stress inducing agents, antimetabolites, mitotic inhibitors, nitrogen mustards, nitrosoureas, alkylsulfonates, platinum agents, taxanes, vinca agents, anti-estrogen drugs, aromatase inhibitors, ovarian suppression agents, VEGF/VEGFR inhibitors, EGF/EGFR inhibitors, RAS inhibitors, PARP inhibitors, cytostatic alkaloids, cytotoxic antibiotics, antimetabolites, endocrine/hormonal agents, bisphosphonate therapy agents, phenphormin and targeted biological therapy agents (e.g., therapeutic peptides described in U.S. Pat. No. 6,306,832, WO 2012007137, WO 2005000889, WO 2010096603 etc.). In some embodiments, the at least one additional therapeutic agent is a chemotherapeutic agent.

Specific chemotherapeutic agents include, but are not limited to, cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines (e.g., daunorubicin and doxorubicin), cladribine, midostaurin, bevacizumab, oxaliplatin, melphalan, etoposide, mechlorethamine, bleomycin, microtubule poisons, annonaceous acetogenins, chlorambucil, ifosfamide, streptozocin, carmustine, lomustine, busulfan, dacarbazine, temozolomide, altretamine, 6-mercaptopurine (6-MP), cytarabine, floxuridine, fludarabine, hydroxyurea, pemetrexed, epirubicin, idarubicin, SN-38, ARC, NPC, campothecin, 9-nitrocamptothecin, 9-aminocamptothecin, rubifen, gimatecan, diflomotecan, BN80927, DX-8951f, MAG-CPT, amsacnne, etoposide phosphate, teniposide, azacitidine (Vidaza), decitabine, accatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephalomannine, streptozotocin, nimustine, ranimustine, bendamustine, uramustine, estramustine, mannosulfan, camptothecin, exatecan, lurtotecan, lamellarin D9-aminocamptothecin, amsacrine, ellipticines, aurintricarboxylic acid, HU-331, or combinations thereof.

Examples of antimetabolites include 5-fluorouracil (5-FU), 6-mercaptopurine (6-MP), capecitabine, cytarabine, floxuridine, fludarabine, gemcitabine, hydroxyurea, methotrexate, pemetrexed, and mixtures thereof.

Examples of taxanes include accatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephalomannine, and mixtures thereof.

Examples of DNA alkylating agents include cyclophosphamide, chlorambucil, melphalan, bendamustine, uramustine, estramustine, carmustine, lomustine, nimustine, ranimustine, streptozotocin; busulfan, mannosulfan, and mixtures thereof.

Examples of topoisomerase I inhibitor include SN-38, ARC, NPC, camptothecin, topotecan, 9-nitrocamptothecin, exatecan, lurtotecan, lamellarin D9-aminocamptothecin, rubifen, gimatecan, diflomotecan, BN80927, DX-8951f, MAG-CPT, and mixtures thereof. Examples of topoisomerase II inhibitors include amsacrine, etoposide, etoposide phosphate, teniposide, daunorubicin, mitoxantrone, amsacrine, ellipticines, aurintricarboxylic acid, doxorubicin, and HU-331 and combinations thereof.

Examples of immunotherapeutic agents include immune checkpoint inhibitors (e.g., antibodies targeting CTLA-4, PD-1, PD-L1), ipilimumab, 90Y-Clivatuzumab tetraxetan, pembrolizumab, nivolumab, trastuzumab, cixutumumab, ganitumab, demcizumab, cetuximab, nimotuzumab, dalotuzumab, sipuleucel-T, CRS-207, and GVAX.

Examples of RAS inhibitors include AMG 510, MRTX849, ARS-3248, BI 1701963, ARS-1620, ARS-853, thiol-reactive GDP analogs, BBP-454, mRNA-5671, KRAS G12D inhibitors, and the like.

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

Kits

The present disclosure also provides kits for the prevention and/or treatment of a RAS-mutant cancer (e.g., RAS mutant pancreatic cancer), comprising one or more TXNRD1 inhibitors. Optionally, the above described components of the kits of the present technology are packed in suitable containers and labeled for the prevention and/or treatment of a RAS-mutant cancer (e.g., RAS mutant pancreatic cancer).

The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kit can also comprise, e.g., a buffering agent, a preservative or a stabilizing agent. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit. In certain embodiments, the use of the reagents can be according to the methods of the present technology.

EXAMPLES

The present technology is further illustrated by the following Examples, which should not be construed as limiting in any way. The examples herein are provided to illustrate advantages of the present technology and to further assist a person of ordinary skill in the art with preparing or using the compositions and systems of the present technology. The examples should in no way be construed as limiting the scope of the present technology, as defined by the appended claims. The examples can include or incorporate any of the variations, aspects, or embodiments of the present technology described above. The variations, aspects, or embodiments described above may also further each include or incorporate the variations of any or all other variations, aspects or embodiments of the present technology. The following Examples demonstrate the preparation, characterization, and use of illustrative compositions of the present technology that inhibit TXNRD1 expression and/or activity.

Example 1: Experimental Materials and Methods

Preprocessing of scRNA-seq count data. The raw, HGNC-aligned, UMI count matrix generated via 10× sequencing was preprocessed and scaled prior to analyzing in downstream analysis pipelines. Low-abundance genes (e.g. average count <0.25) and genes with reads in <10% of cells as well as cells with non-zero reads for <10% of all genes were removed from the count matrix. To adjust for discrepancies in sequencing depth between individual cells, count matrices were normalized in some cases and scaled prior to carrying forward in subsequent analyses. Methods of normalization included, but were not limited to: 1) globally scaling cell-level counts to match the median depth across all cells (scalar adjustment), and 2) solving linear systems to obtain unique scaling factors for individual cells. In some cases, inter-sample batch effects were corrected via a mutual nearest neighbors algorithm.

Supervised dimensionality reduction. In order to computationally identify therapeutic targets, high-dimensional count data were mapped to a lower-dimensional, latent space. The latent space was constructed via supervised dimensionality reduction on a collection of pure cell types (e.g., pancreatic adenocarcinoma, ductal, and acinar cells), with cell type serving as the supervised label for reduction. In this way, the latent space maximized the separability between cancer and primary cells. In some cases, cells targeted with an essential gene (e.g., PCNA or MCM6 via RNAi or CRISPR) were also included in construction of the latent space in order to define a region of "toxicity." Toxicity manifested as, e.g., knocked down a gene induced apoptosis in primary cells. Following model training, cells interrogated with CRISPR target candidates were mapped to the same latent space constructed from the pure cell types in order to quantify their transcriptional shift towards a wild-type expression profile (therapeutic index).

Several algorithms were used for supervised dimensionality reduction. In some cases, the Elbow method (Richards et al., *J Shoulder Elbow Surg* 8(4): 351-354 (1999)) was used to determine the optimal number of dimensions for the latent space.

Scoring of therapeutic index. The target genes interrogated via a pooled CRISPRi library were quantified in terms of their ability to shift the transcriptional profile of cancer cells back to a wild-type-like expression state (therapeutic index). Genes were scored via machine learning algorithms. Briefly, separate, single-class machine learning algorithms were trained on the latent expression profiles of distinct cell types including, but not limited to: 1) pancreatic ductal cells; 2) pancreatic acinar cells; 3) pancreatic adenocarcinomas; and 4) pancreatic adenocarcinomas with an essential gene (e.g., PCNA or MCM6) targeted (via CRISPR/RNAi) as a model for toxicity. Each of the trained machine learning models was then used to score candidate genes based on the output of the decision function applied to latent expression profiles of single cells targeted with the CRISPRi library. In some cases, cells were repeatedly sampled with replacement in order to construct a bootstrap confidence interval for the decision function estimate.

2-D Pooled negative selection RNAi screening. A custom shRNA library focused on 442 drug target genes (2245 shRNAs, five to six per gene) was designed and constructed as previously described (Huang et al., *Genes Dev.* 28(16): 1800-1814 (2014)). The library was cloned into TRMPV-Neo vector and transduced into Tet-On murine pancreatic ductal adenocarcinoma (mPDAC) cells (Kras$^{G12D}$; Myc; shp53). Lito et al., *Cancer Cell* 25(5):697-710 (2014). The conditions used for transduction of the library predominantly led to a single retroviral integration and represented each shRNA in a calculated number of at least 1000 cells. Transduced cells were selected for 5 days using 1 mg/mL G418 (Invitrogen). At each passage, >20 million cells were maintained to preserve library representation throughout the experiment. After drug selection, T0 samples were obtained (20 million cells per replicate) and sorted for Venus$^+$ cells. After 12 days (six passages, T12), 20 million shRNA-expressing (dsRed$^+$ Venus$^+$) cells were sorted for each replicate using a FACSAriaII (BD Biosciences). Genomic DNA from T0 and T12 samples was isolated by two rounds of phenol extraction using PhaseLock tubes (5 Prime) followed by isopropanol precipitation.

The results obtained from the mPDAC screen were then compared with the results obtained from Myc; p53$^{-/-}$ murine hepatocellular carcinoma (mHCC) cells (Huang et al., *Genes Dev.* 28(16): 1800-1814 (2014)), and a two-dimensional RNAi screening plot was constructed. See, e.g., FIG. 3A.

Plasmids. For conditional RNAi experiments, shRNAs were expressed from the TRMPV-Neo vector from either miR-E or miR-30 backbones, which have been described previously (Zuber et al., *Nat Biotechnol.* 29(1):79-83 (2011); Fellmann et al., *Cell Rep* 5(6): 1704-1713 (2013)). Knockdown efficiency or overexpression was evaluated by immunoblotting.

Immunoblotting. Cell pellets were lysed in Laemmli buffer (100 mM Tris-HCl pH 6.8, 5% glycerol, 2% SDS, 5% 2-Mercaptoethanol). Equal amounts of protein were resolved on 12% SDS-polyacrylamide gels and transferred to PVDF membranes for 120 minutes under 90V. The abundance of β-actin was monitored to ensure equal loading. Images were analyzed using the AlphaView software (ProteinSimple). Immunoblots were performed using antibodies for TXNRD1 (TrxR1) (1:1000, sc-28321, Santa Cruz Biotechnology), KRAS (1:200, WH0003845M1, Sigma-Aldrich), or β-actin-HRP (1:10000, A3854, Sigma).

Proliferation assays. Competitive proliferation assays using shRNAs in TRMPV-Neo vector (with miR-30 or miR-E backbone) were performed as described previously (Huang et al., *Genes Dev.* 28(16): 1800-1814 (2014)). Assays for in vitro growth inhibition by auranofin or piperlongumine were performed by counting the viable cell numbers using CellTiter-Glo Luminescent Cell Viability Assay (Promega) after incubation of cells in the presence of increasing concentrations of auranofin or piperlongumine for 72 hr. Proliferation rates were calculated by dividing viable cell numbers at 72 hr by the viable cell numbers at 0 hr. Relative proliferation rates were calculated by normalizing to the proliferation rate of vehicle-treated cells.

Animal studies. All experimental procedures described in this study were approved by the Institutional Animal Care and Use Committee (IACUC) at Memorial Sloan Kettering Cancer Center (NY), under protocol number 11-06-016 and 11-06-018. Mice were maintained under specific pathogen-free conditions, and food and water were provided ad libitum.

In vivo conditional RNAi experiments. Tet-On murine PDAC cells were transduced with luciferase-hygro and TRMPV-Neo-miR-E shRNA constructs. One million murine PDAC cells were orthotopically transplanted into female nude recipient mice (NCR nu/nu, purchased from Charles River laboratories and Harlan Laboratories). For whole-body bioluminescent imaging, mice were intraperitoneally injected with 50 mg/kg D-Luciferin (Goldbio), and after 10 min, analyzed using an IVIS Spectrum system (Caliper LifeSciences). Quantification was performed using Living Image software (Caliper LifeSciences) with standardized round regions of interests covering the mouse trunk and extremities. For shRNA induction, animals were treated with doxycycline in drinking water (2 mg/ml with 2% sucrose; Sigma-Aldrich) and food (625 mg/kg, Harlan Laboratories).

In vivo drug treatment experiments. For auranofin treatment trials, 16 mg auranofin was first solved in 4 mL ethanol, and then diluted with 12 mL PBS to a final concentration of 1 mg/ml. Mice were given daily auranofin (10 mg/kg) or a similar volume of vehicle by intraperitoneal injection. The sick animals were sacrificed and pancreatic tissues and tumors were used for further analysis.

RNA sequencing and Gene set enrichment analysis (GSEA) analyses. For RNA sequencing, total RNA from mPDAC cells harboring shRNAs targeting control *Renilla* Luciferase or TXNRD1 was isolated using RNeasy Mini Kit, QIAshredder Columns and RNase-Free DNase Set (Qiagen). RNA-Seq library construction and sequencing were performed according to protocols used by the Integrated Genomics Operation (IGO) Core at MSKCC. 5-10 million reads were acquired per replicate sample. After removing adaptor sequences with Trimmomatic (Bolger et al., 2014), RNA-seq reads were aligned to GRCh37.75(hg19) using the STAR alignment tool (Dobin et al., 2013). Genome wide transcript counting was performed by HTSeq to generate FPKM matrix (Anders et al., 2015 Bioinformatics). Gene set enrichment analysis (Subramanian et al., 2005) was performed using GSEA v2.07 software.

Statistics. Data are presented as mean±standard deviation if not otherwise stated. Statistical significance between groups was calculated by two-tailed Student's t-test. Correlation was calculated by Pearson test. Prism 7 software was used to calculate the IC$_{50}$ values. Significance values are P<0.05 (*), P<0.01 (), and P<0.001 (*). Volcano plots were prepared in some cases.

Analysis of gene dependency. The data of human cancer cell line whole genome sgRNA screen used for all heatmaps was from http://genomecrispr.dkfz.de/. The Log 2FC (abundance fold-change with log transformation) was used to calculate the gene dependency score for each gene in each experiment. The gene dependency score was calculated via taking the average of Log 2FC of all sgRNAs targeting the same gene. Un-supervised clustering using "Pheatmap" R package was used to cluster genes with similar phenotypes for visualization.

Determination of fold change in sensitivity to Auranofin and quantitative analysis of drug synergy. CompuSyn software (Version 1.0) (http://www.combosyn.com), which is based on the Median-Effect Principle and the Combination Index-Isobologram Theorem was used to analyze drug synergism. Combination index (CI) values CI>1 indicates antagonism; CI=0.75-1.25 indicates additive effects; and <1 indicates synergism. Each GI (Growth inhibition) or CI score represents data from at least three independent experiments.

Auranofin pharmacokinetics. The plasma and pancreas pharmacokinetics of gold were analyzed in 9 NCR nu/nu mice following administration of a single dose of 10 mg/kg auranofin suspension via intraperitoneal injection. Plasma and pancreas samples for determination of gold concentration were obtained at 2, 4, and 24 hours following administration of auranofin. Collected plasma and pancreas samples were analyzed using an inductively coupled plasma mass spectrometry (ICPMS) method to quantify gold concentration.

Figure 1A:
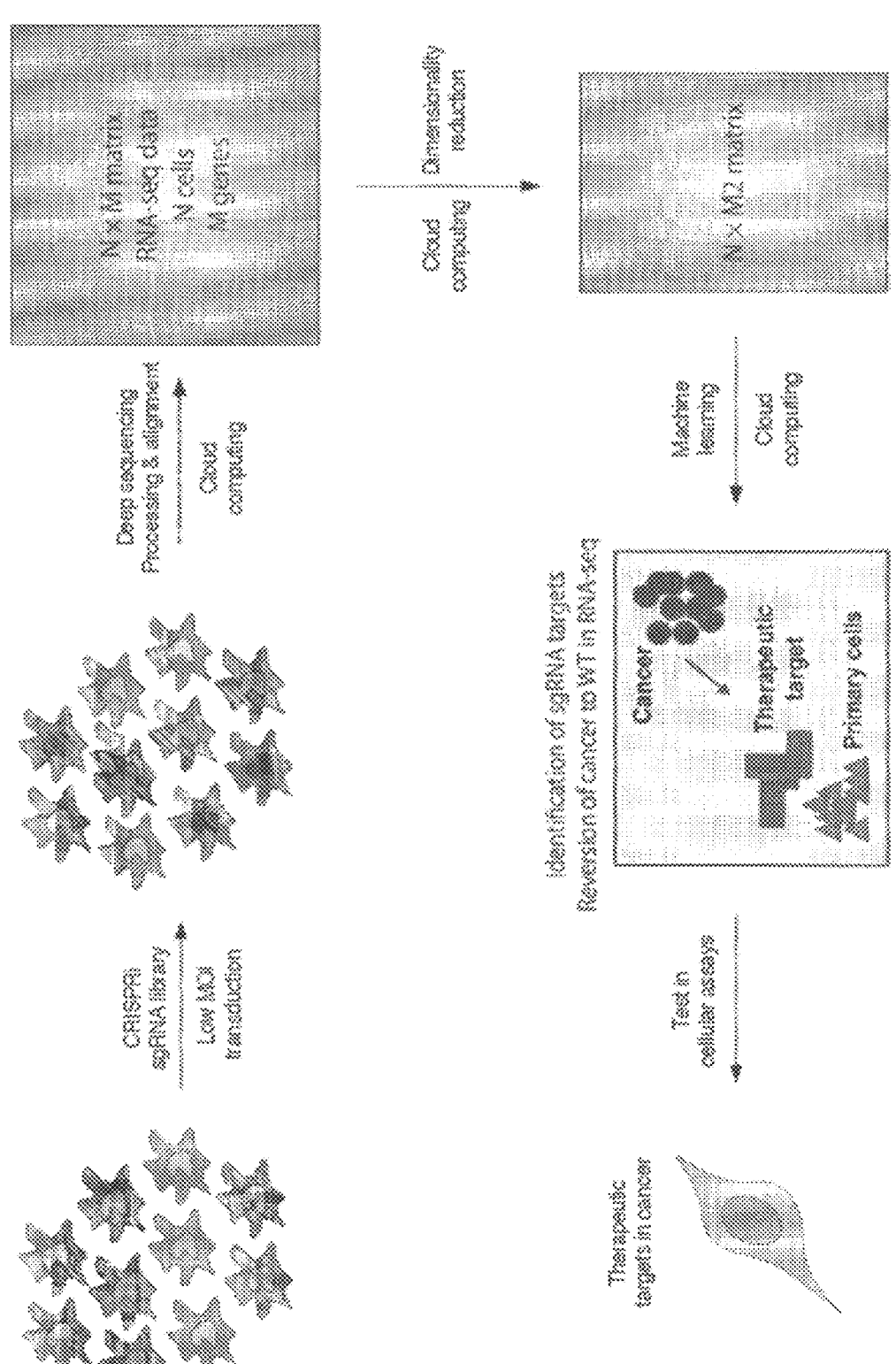
FIG. 1A shows a schematic diagram illustrating the pipeline used in the present disclosure for discovery of therapeutic targets in KRAS-mutant pancreatic cancer. The pipeline included low multiplicity-of-infection (MOI) transduction of KRAS-mutant pancreatic cancer cells with a clustered regularly interspaced short palindromic repeats based interference (CRISPRi) library (See, e.g., Gilbert et al., *Cell* 154: 442-451 (2013)), single-cell RNA sequencing (scRNA-seq), genomic alignments and generation of count matrix (See, e.g., Tang et al., Nature Methods 6: 377-382 (2009)), supervised dimensionality reduction, and machine learning algorithms to identify novel targets in which suppression maximally and selectively target cancer cells.
Figure 1B:
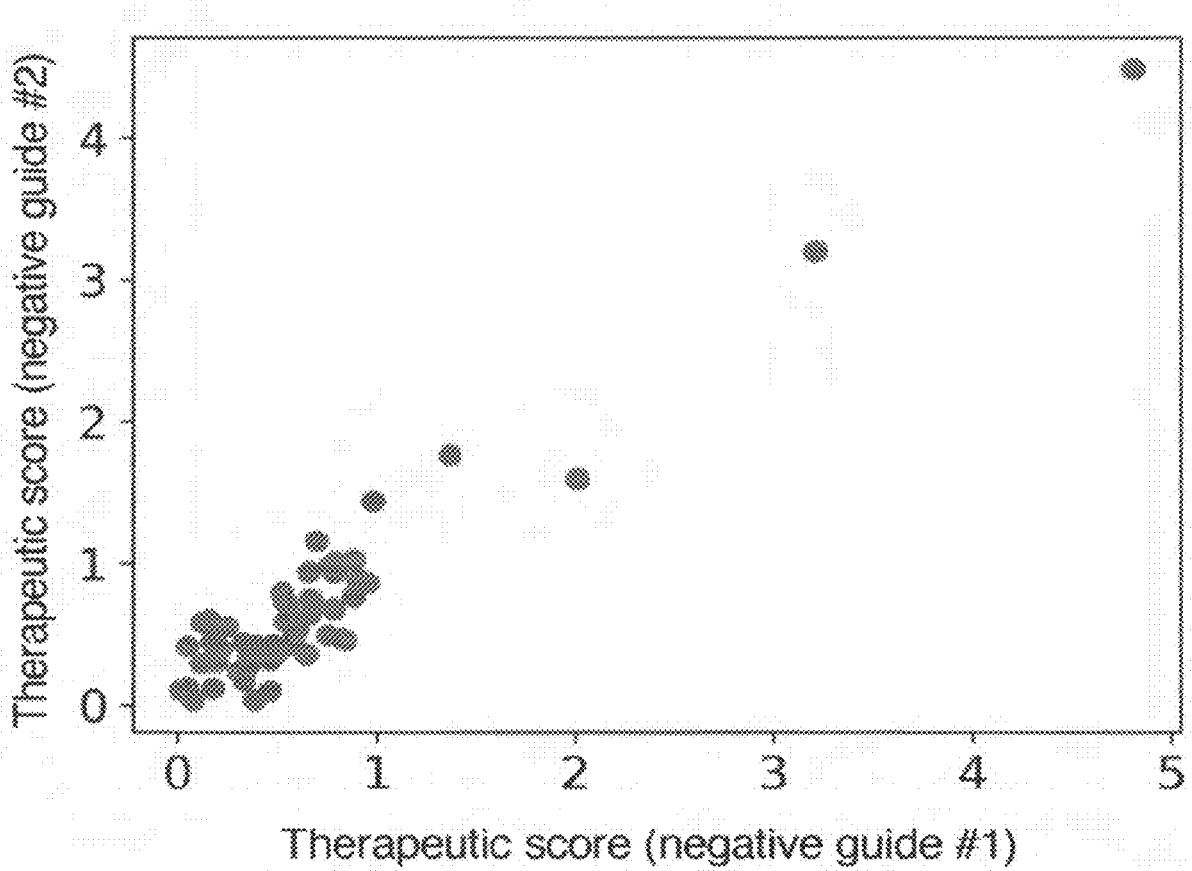
FIG. 1B shows a scatter plot of z-transformed therapeutic scores for several CRISPR target candidates. The therapeutic index was scored across two negative guide RNAs based on a machine learning algorithm, which collectively established negative control benchmarks for identifying therapeutic targets.

Example 2: Computational Discovery and Validation of Novel Targets in Kras-Mutant Pancreatic Cancer FIGS. 1A-1B provide a pipeline for computational discovery of therapeutic targets in RAS-mutant pancreatic cancer. As shown in FIG. 1A, Kras-mutant pancreatic cell lines were screened using a CRISPRi library transduced at a low multiplicity of infection (MOI). The transcriptomes of single cells were isolated and converted to DNA libraries using a Chromium instrument (10× Genomics) and an enzyme kit (10× Genomics), and were sequenced using Hiseq4000 system (Illumina). Single-cell RNA sequencing (scRNA-seq) profiles of individual cells were matched to their respective CRISPR targets via paired-end sequencing and using barcodes. The raw reads in FASTQ format were aligned with whole genome and mapped to an appropriate genomic coordinate and HGNC gene for each cell, resulting in a count matrix comprised of N cells×M genes (See FIG. 1A). This N×M matrix was further reduced to a N×50 matrix via supervised dimensionality reduction (See FIG. 1A). The dimensionality reduction model was trained to identify pure cell types (e.g. cancer cells, ductal cells, acinar cells, or cancer cells expressing a non-targeted guide RNA, which served as the negative controls) such that the lower-dimensional latent space maximally separated healthy cells and cancer cells from each other (See FIG. 1A-2A). Cells expressing CRISPR targets that maximally drove mRNA expression pattern away from the negative controls, and towards healthy cells (ductal cells or acinar cells) were identified using this algorithm, and such CRISPR targets constituted the most promising targets that were pursued in preclinical development.

As shown in FIGS. 1A-1B, the therapeutic index was quantified using machine learning algorithms. Briefly, separate machine learning models were trained to identify distinct cell populations, including: 1) pancreatic ductal cells (positive control for therapeutic index); 2) pancreatic acinar cells (positive control for therapeutic index); 3) Kras-mutant PDAC cells expressing a non-target guide RNA (negative control for therapeutic index); and 4) Kras-mutant PDAC cells expressing an essential gene targeted (positive control for a toxic target). As shown in FIGS. 1A-1B, the trained machine learning models were then applied to RNA-seq data of Kras-mutant PDAC cells expressing a CRISPRi targets to detect cells that exhibited RNA-seq profiles similar to pancreatic acinar cells and distinguishable from Kras-mutant PDAC cells expressing negative control for therapeutic index. Identities of the CRISPRi targets expressed by such cells were identified based on paired-end sequencing and barcodes. Targets with maximal therapeutic index were chosen to pursue in preclinical development.

Example 3: Computational Identification of TXINRD1 as a Therapeutic Target in KRAS-Mutant Pancreatic Cancer As shown in FIG. 1B, the scRNA-seq profiles of individual Kras-mutant PDAC cells expressing CRISPRi targets were analyzed using decision functions of machine learning algorithms trained on two non-target guide RNAs, a toxic target, and a healthy ductal cell line as described above. The outputs of the decision functions were further transformed via a variety of methods, including but not limited to: effect size, K.S.-statistic, z-score, or p-value relative to a control population. Scores across multiple machine learning algorithms and replicates were further aggregated via various methods, including but not limited to: average, weighted average, rank aggregation, weighted rank aggregation, Stouffer's method (z-scores), and Fischer's method (p-values).

Figure 2A:
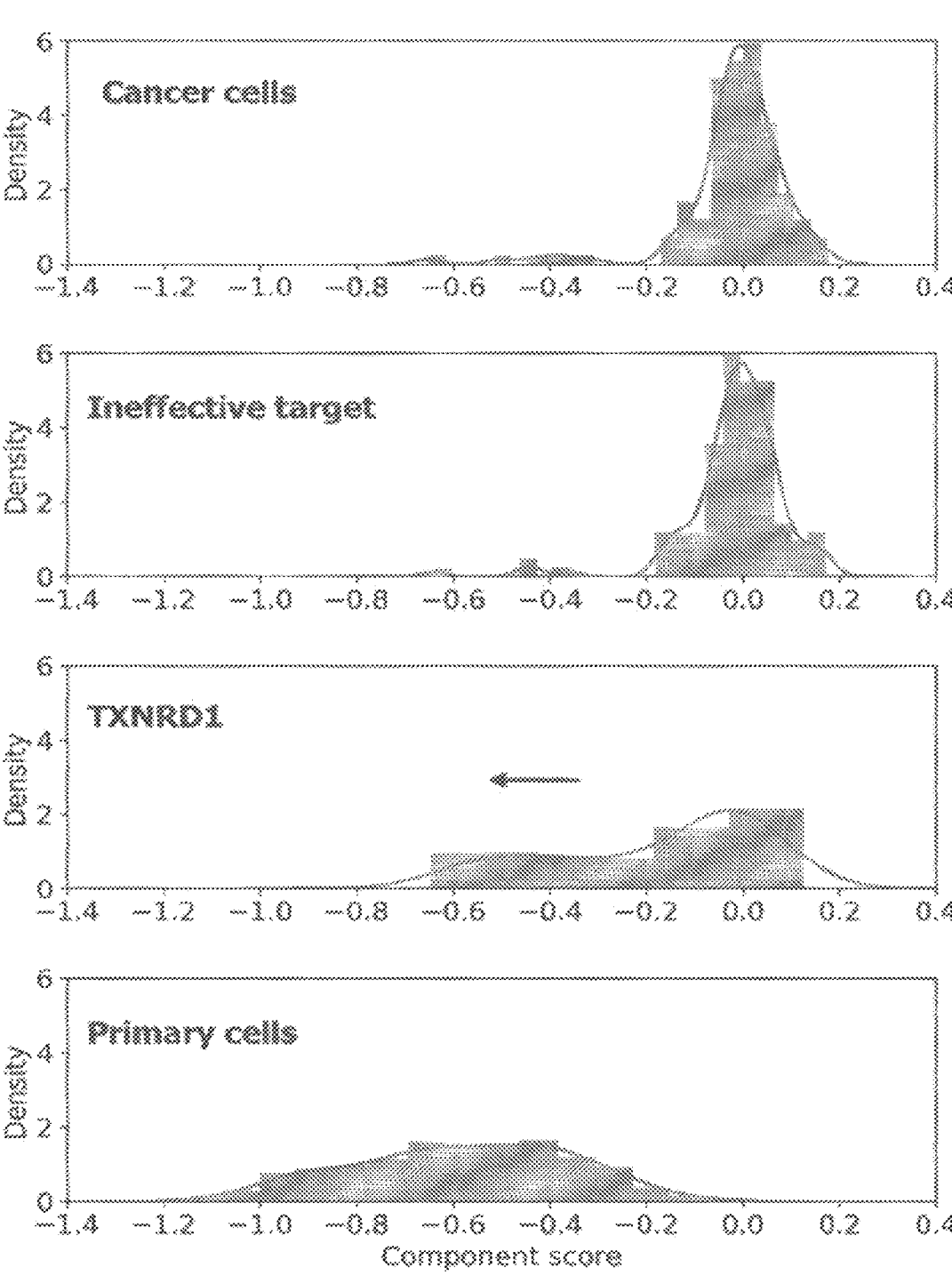
FIG. 2A shows the distribution of cell type populations along a single dimension after supervised dimensionality reduction using machine learning algorithms. The following populations are shown: 1) Cancer cell: cancer cells with a non-targeting guide RNA gene targeted (N=120), 2) Ineffective target: cancer cells with a negative control gene targeted (N=122), 3) TXNRD1: cancer cells with TXNRD1 targeted (N=87), and 4) Healthy cell: healthy ductal cells (N=600).
Figure 2B:
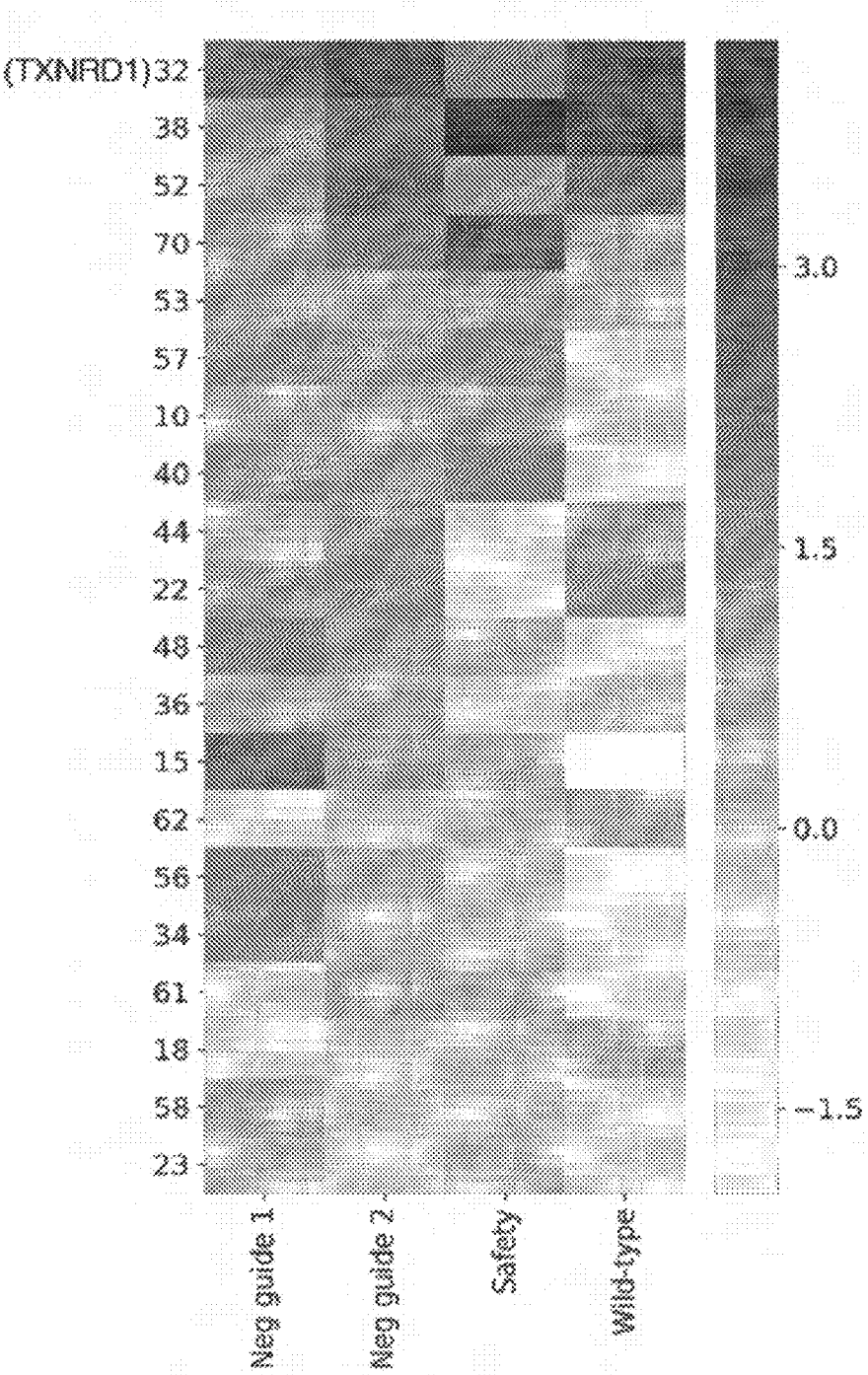
FIG. 2B shows a heat map illustrating z-transformed therapeutic scores for the top 20 candidate targets. The candidate targets are displayed in descending order based on average rank across the four indicated decision functions from a machine learning algorithm. As shown, TXNRD1 exhibited the highest average rank.
Figure 2C:
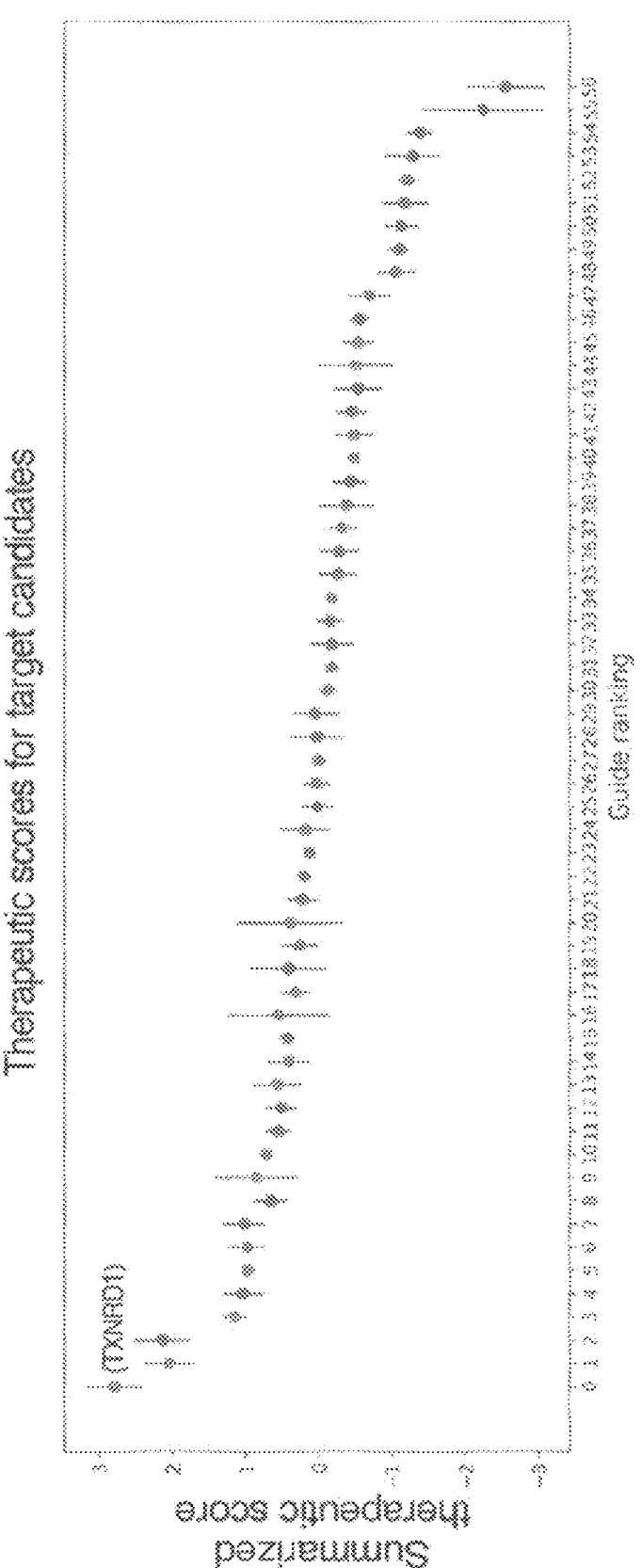
FIG. 2C shows a graph depicting weight-averaged decision function scores for therapeutic index across a panel of candidate targets. TXNRD1 emerged as the highest-ranking target.

As shown in FIG. 2A, TXNRD1 was identified as a CRISPRi target that transformed Kras-mutant PDAC cells to exhibit RNA-seq profiles similar to pancreatic acinar cells. Distribution of cell type populations was analyzed along a single dimension after supervised dimensionality reduction using machine learning algorithms and plotted. As shown in FIG. 2A, Kras-mutant PDAC cells expressing guide RNA targeting TXNRD1 (N=87), showed a shift towards healthy ductal cells (N=600). By comparison, Kras-mutant PDAC cells expressing an ineffective CRISPRi target (a non-targeting guide RNA (N=122) largely overlapped the profile of cancer cells. As shown in FIG. 2B, the z-transformed therapeutic index of TXNRD1, averaged across the four decision functions from machine learning algorithms, was the highest of the top 20 candidate targets. Similarly, as shown in FIG. 2C, TXJRD1 exhibited the highest weight-averaged decision function scores for therapeutic index among a panel of over fifty candidate targets.

Figure 3A:
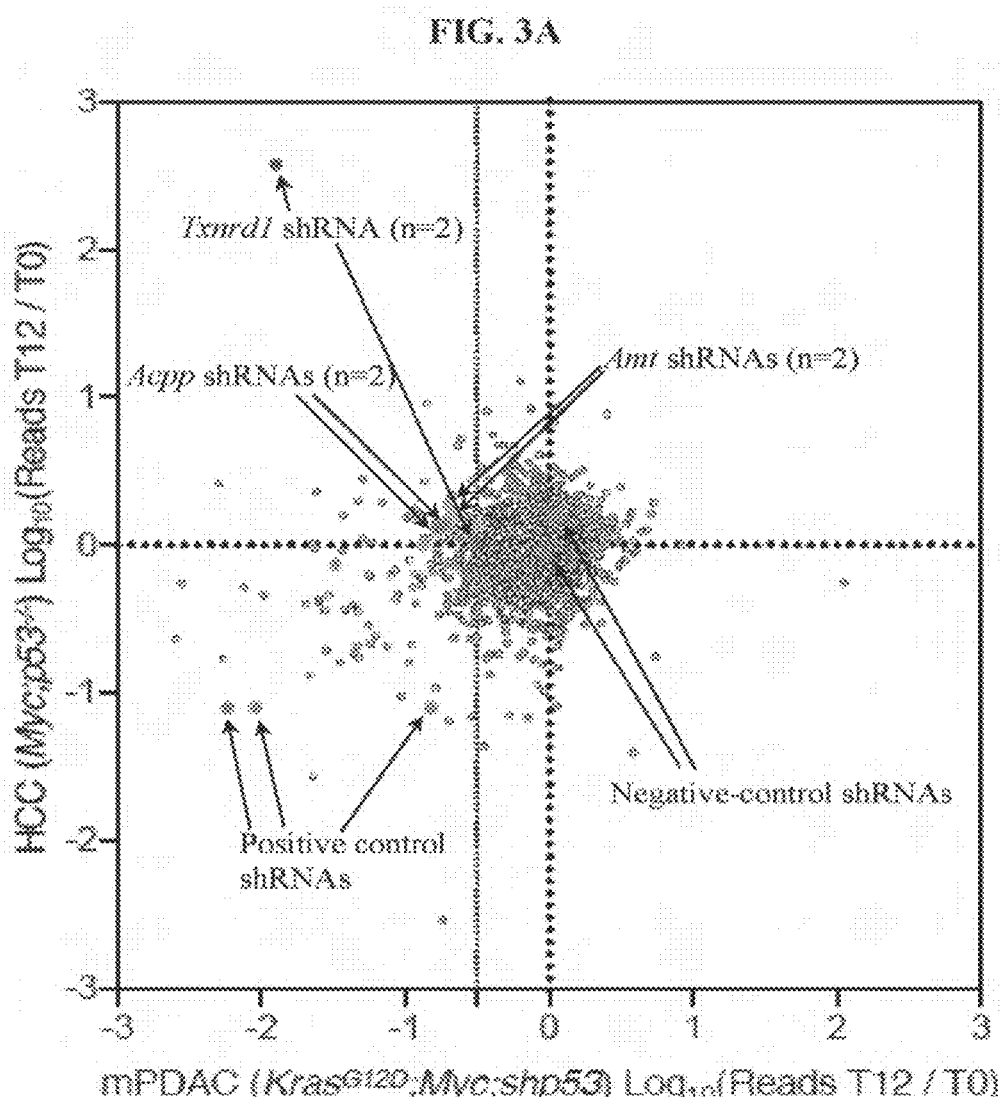
FIG. 3A shows the results of cross-analysis of shRNA-mediated pooled negative selection screening. shRNA-mediated pooled negative selection screening was performed in (1) KrasG12D; Myc; shp53 murine pancreatic ductal adenocarcinoma (mPDAC) cells, and (2) Myc; p53$^{-/-}$ murine hepatocellular carcinoma (mHCC) cells. The results of shRNA-mediated pooled negative selection screening from the two cell types were cross-analyzed for comparative purposes.
Figure 3C:
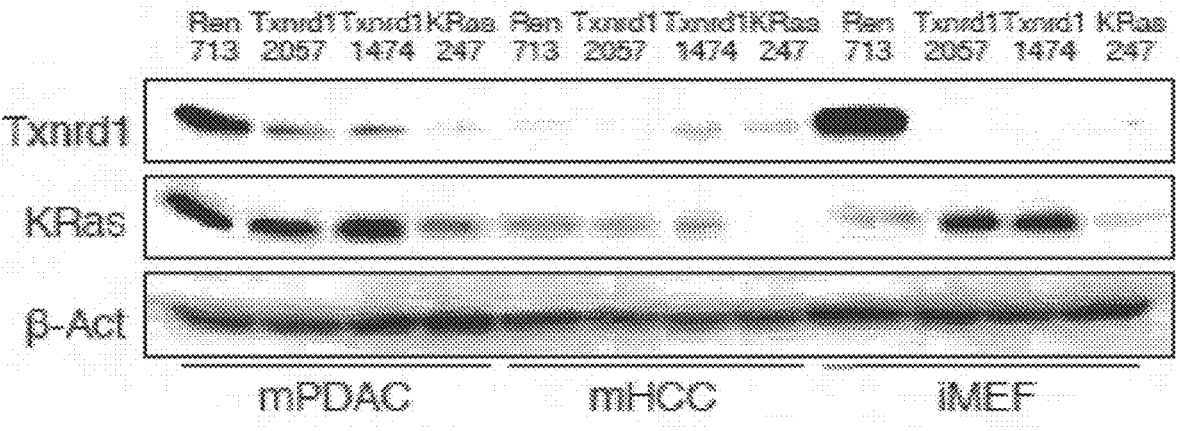
FIG. 3C shows immunoblots illustrating TXNRD1 knockdown in mPDAC, mHCC and iMEF cells.

Example 4: Identification of TXNRD1 as a Therapeutic Target by a 2-D RNAi Screening Approach To selectively identify drug targets that are essential for the maintenance of KRAS-mutant PDAC, a custom library of short hairpin RNAs (shRNAs) directed toward known drug targets was screened for negative selection in a genetically defined murine HCC model (Kras$^{G12D}$; Myc; shp53). The results were cross-analyzed with prior negative selection results from a murine HCC model (Myc; p53$^{-/-}$) (Huang et al., *Genes Dev.* 28(16): 1800-1814 (2014)). As shown in FIG. 3A, shRNAs targeting Txnrd1, Acpp, and Amt were found to be selectively depleted in the Kras-mutant PDAC cells, compared to the negative control shR-NAs, which remained unchanged in both cell lines. In comparison, positive control shRNAs were depleted in both murine HCC and murine HCC (See FIG. 3A).

To detect depletion of cells expressing specific siRNA was quantitated in mPDAC, mHCC and iMEFs, these cells transduced with a virus carrying an inducible shRNA against Txnrd1, Acpp, Amt and controls: Ren.713 (a non-targeting shRNA which served as a negative control), Rpa3.561 (a positive control for growth inhibition in all proliferating cells), Kras.247 (a positive control for mPDAC-specific growth inhibition). The percentage of cells expressing these shRNAs was determined on day 0 and on day 12 of shRNA induction. Decrease in the percentage of cells expressing a shRNA indicated inhibitory effects of the shRNA. As shown in FIG. 3B, shRNA Ren.713, which is a non-targeting negative control (against *Renilla* luciferase) had no effect in any cells, the positive control shRNA Rpa3.561 was depleted in all cell types tested. The mPDAC-specific positive control Kras.247 was depleted in mPDAC compared to mHCC and iMEFs. As shown in FIG. 3B, shRNAs against Txnrd1, Acpp, and Amt exhibited inhibitory effects in Kras-mutant PDAC cells (Kras$^{G12D}$. Myc; shp53), compared to the negative control, but not in mHCC cells (Myc; p53$^{-/-}$) or nontransformed immortalized mouse embryonic fibro-blasts (iMEF). The effect of Txnrd1 shRNA was more pronounced than shRNA targeting Acpp or Amt. The West-ern blots shown in FIG. 3B show that the shRNA reduced amounts of proteins they targeted. Therefore, this assay also identified Txnrd1 as a promising target. Given that RAS gain of function mutations (e.g., at codon 12, 13, or 61) occur in regions that share 100% amino acid sequence identity among the KRAS, NRAS, and HRAS isoforms (See Prior et al., *Cancer Research* 72(10) (2012)), inhibition of TXNRD1 is anticipated to treat cancers associated with KRAS, NRAS, and HRAS mutations.

Figure 6A:
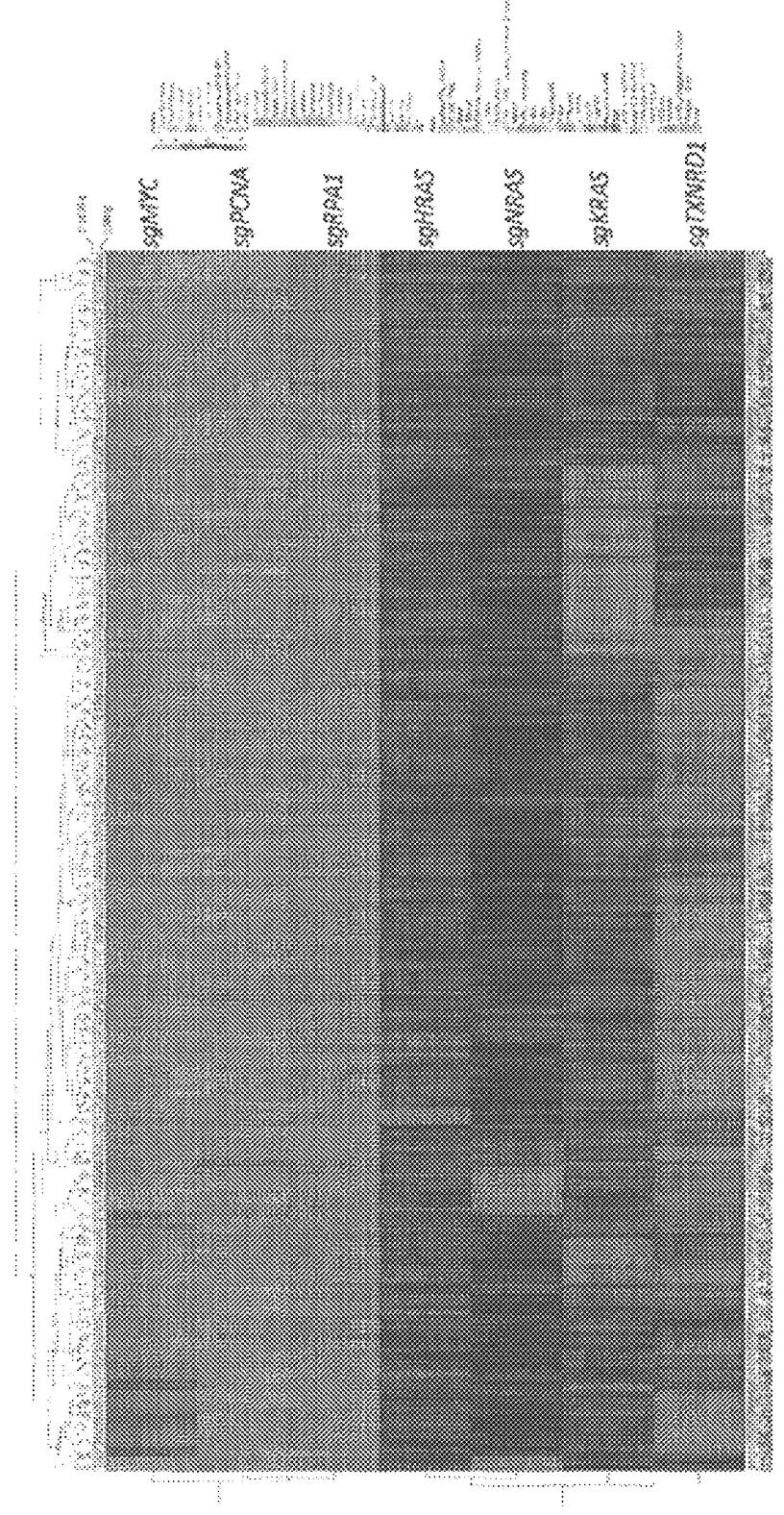
FIGS. 6A-6B show heat maps illustrating the survival dependency of the indicated cell lines on listed genes. Each column represents a cell line that exhibited the highest average rank and each row represents a gene. Gene dependency score was calculated by taking the average of log 2FC (abundance fold change relative to non-diseased tissue) of all corresponding sgRNAs (FIG. 6A) or shRNAs (FIG. 6B). Zero represents no change, negative number represents depletion, and positive number represents an enrichment of indicated cell lines. Un-supervised clustering was used to cluster genes with similar phenotypes. As shown, knocking out or knocking down replication genes RAP1 or PCNA resulted in general lethality to almost all cell lines. In contrast, TXNRD1 is conditionally required for certain cell lines which exhibit similar dependency for KRAS, HRAS, and NRAS.
Figure 6B:
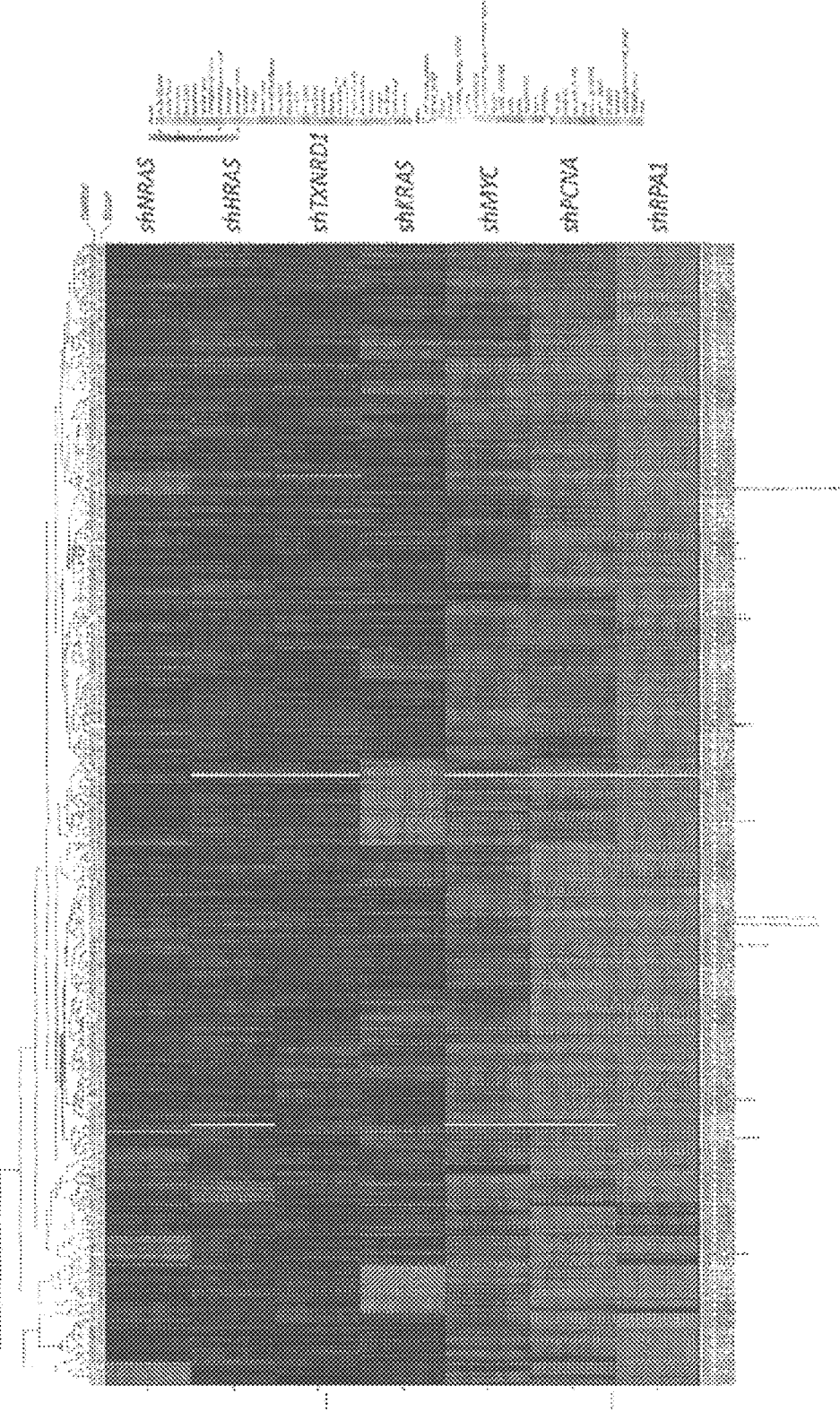

TXNRD1 dependency was further investigated in various cell lines. As shown in FIGS. 6A-6B, knocking out or knocking down replication genes RAP1 or PCNA resulted in general lethality to almost all cell lines. In contrast, TXNRD1 is conditionally required for certain cell lines which exhibit similar dependency for KRAS, HRAS, and NRAS.

These results demonstrate that the TXNRD1 inhibitor compositions of the present technology are useful in meth-ods for treating a disease or condition characterized by elevated levels of RAS expression and/or elevated levels of TXNRD1 expression in a subject in need thereof.

Example 5: KRAS-Mutant PDAC Growth is Sensitive to Pharmacological TXNRD1 Inhibition To evaluate the effect of pharmacological inhibition of TXNRD1 in pancreatic cancer with small molecule drugs, inhibitor studies with myricetin, manumycin A, protopor-phyrin IX, and auranofin were undertaken.

Auranofin is an inhibitor of enzymatic activity of TXNRD1 (See Gromer et al., *J Biol Chem* 273(32): 20096-20101). Myricetin, manumycin A and protoporphyrin IX are also inhibitors of enzymatic activity of TXNRD1. mPDAC cells were treated with the TXNRD1 inhibitor auranofin or DMSO for 72 hr, and viability was measured. DMSO treatment served as a negative control causing a lack of growth inhibition. Viable cell number of DMSO-treated cells was set to 1. Viability of auranofin-treated cells, which was normalized to that of DMSO-treated cells, was plotted as a function of auranofin concentration and was fit to an exponential growth curve. Each of myricetin, manumycin A and protoporphyrin IX were also subjected to similar treat-ment.

Figure 3D:
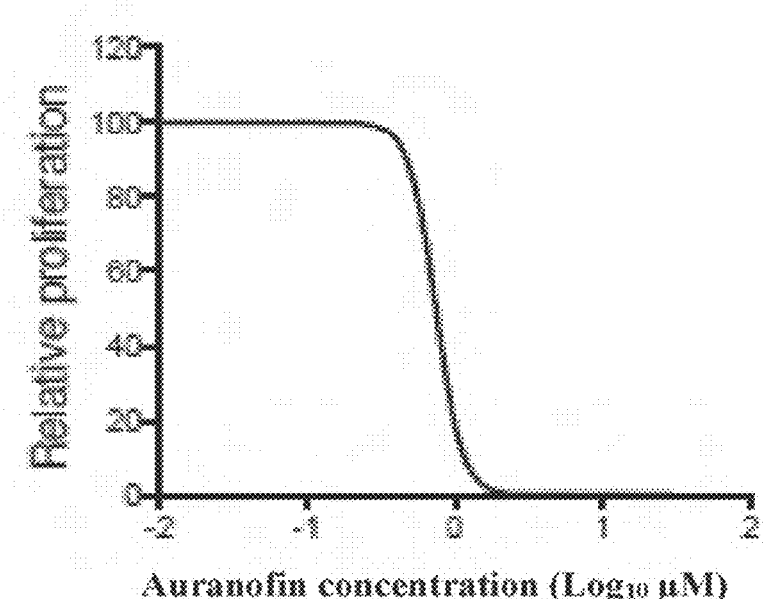
FIG. 3D shows the effect of pharmacological inhibition of TXNRD1 in pancreatic cancer cells. mPDAC cells were treated with increasing doses of auranofin for 72 hours. Relative proliferation was calculated by measuring viable cell numbers, and normalizing to the viable cell numbers of DMSO-treated cells, which were set to 1. Relative proliferation was then plotted as a function of auranofin concentration and fit to an exponential curve.

As shown in FIG. 3D, auranofin inhibited growth of mPDAC cells at submicromolar concentration. These results demonstrate that the TXNRD1 inhibitor compositions of the present technology are useful in methods for treating a disease or condition characterized by RAS mutations, elevated levels of RAS expression and/or elevated levels of TXNRD1 expression in a subject in need thereof.

Example 6: KRAS Status Predicts Response to TXINRD1 Inhibition

Figure 3E:
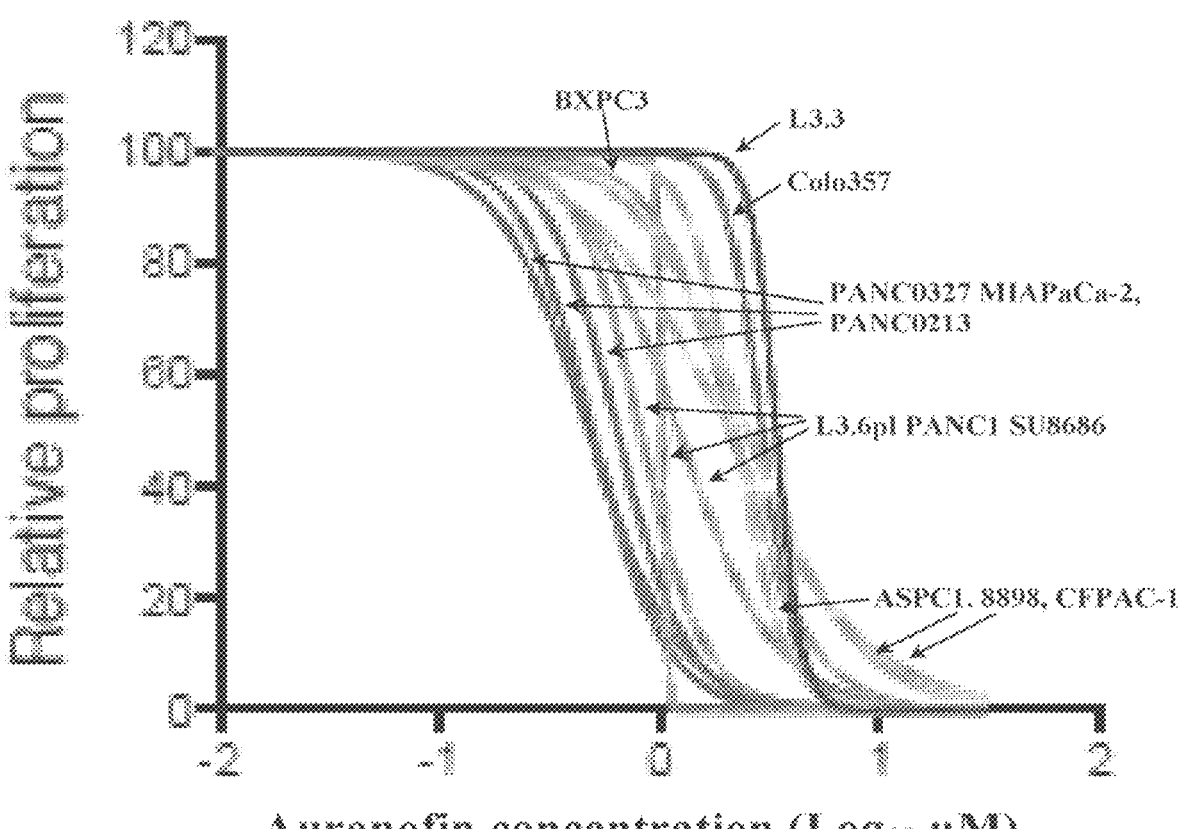
FIG. 3E shows the effect of pharmacological inhibition of TXNRD1 in human pancreatic cancer cells, as measured by the change in viable cell numbers after 72 hours in culture with increasing doses of auranofin. Relative proliferation was calculated by measuring viable cell numbers, and normalizing to the viable cell numbers of DMSO-treated cells, which were set to 1. Relative proliferation was then plotted as a function of auranofin concentration and fit to an exponential curve. L3.3, Colo357, and BXPC3 have wild-type KRAS, and rest of the cell lines harbor a KRAS mutation.

Since the screening system discussed above and FIGS. 1A-3B was driven by mutant Kras, p53 loss and Myc overexpression, whether alterations in either gene could dictate sensitivity to TXNRD1 inhibition was investigated. Twelve pancreatic cancer cell lines were treated with increasing concentration of auranofin or DMSO. Among the cell lines used in this experiment L3.3, Colo357, and BXPC3 have wild-type KRAS. The cell lines PANC0327, MIAPaCa-2, PANC0213, ASPC1, 8898, CFPAC-1, L3.6pl, PANC1 and SU8686 harbored KRAS mutations. As shown in FIG. 3E, although there was variability from a cell line to cell line, the KRAS mutant cells were generally more sensitive to auranofin than the wild-type KRAS cells.

Figure 4A:
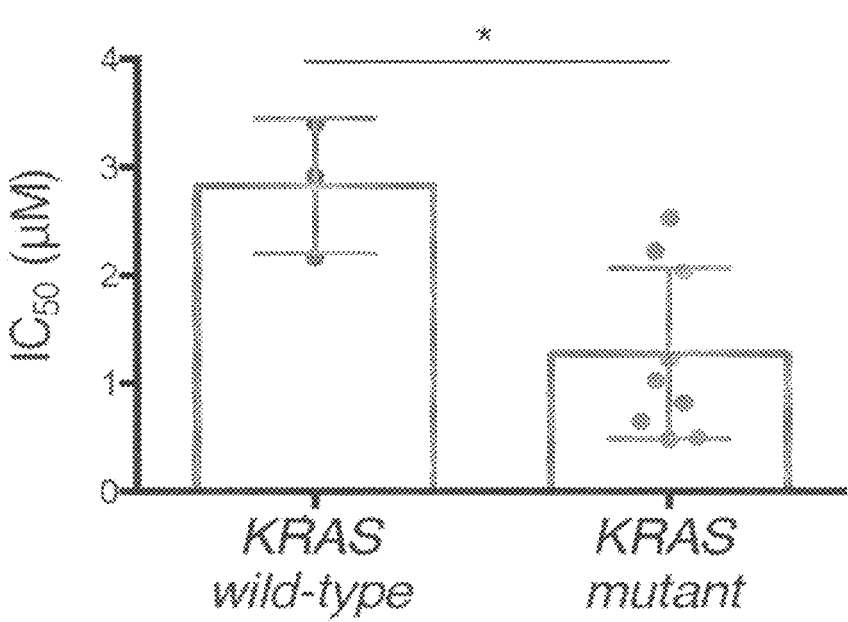
FIG. 4A shows a bar graph illustrating the correlation of $IC_{50}$ value of the TXNRD1 inhibitor auranofin with KRAS status in human pancreatic cancer cell lines (n=12).
Figure 4B:
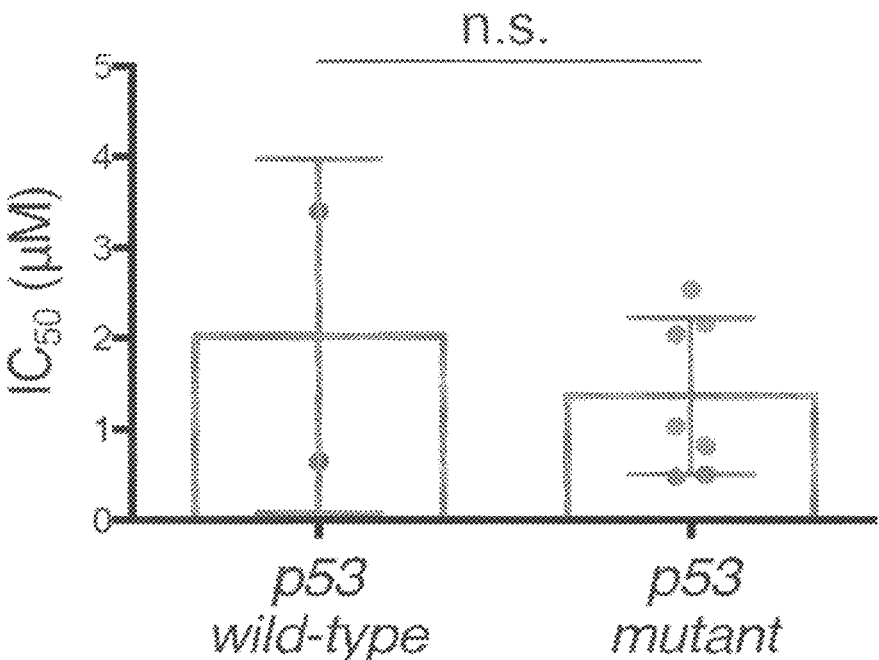
FIG. 4B shows a bar graph illustrating the correlation of $IC_{50}$ of auranofin with p53 status in human pancreatic cancer cell lines (n=9).
Figure 4C:
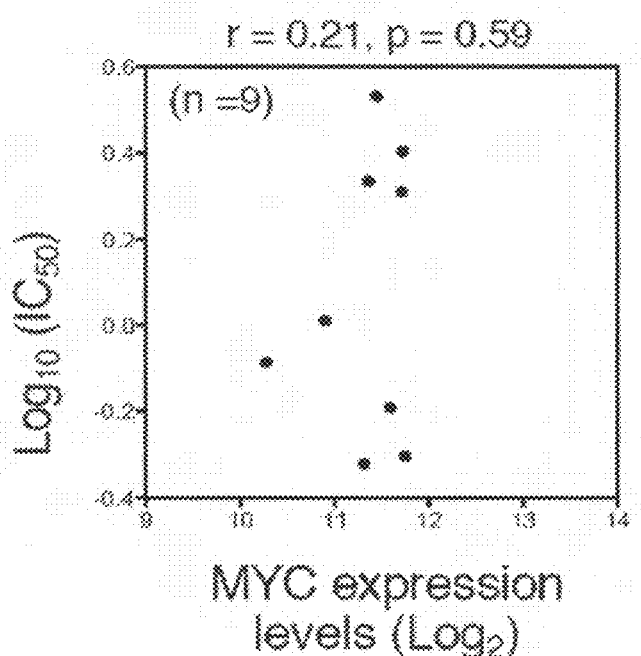
FIG. 4C shows a scatter plot illustrating the correlation of $IC_{50}$ of auranofin with Myc expression levels in human pancreatic cancer cell lines (n=9).
Figure 4D:
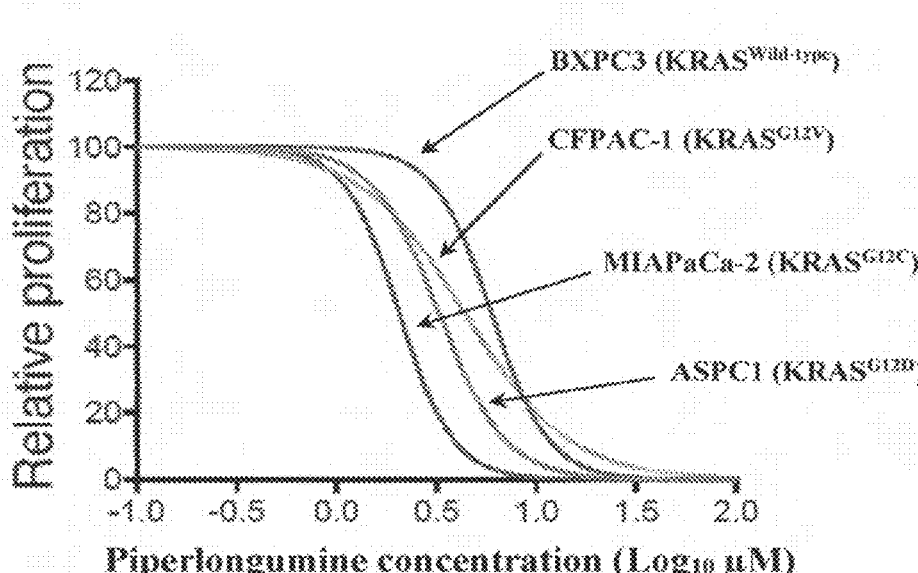
FIG. 4D shows the effect of pharmacological inhibition of TXNRD1 as measured by treatment of pancreatic cancer cells with piperlongumine (another TXNRD1 inhibitor) for 72 hours. Cancer cells harboring different KRAS mutations (G12C, G12D, G12V) or wild-type allele were assayed. Relative proliferation was calculated by measuring viable cell numbers, and normalizing to the viable cell numbers of DMSO-treated cells, which were set to 1. Relative proliferation was then plotted as a function of auranofin concentration and fit to an exponential curve.

To understand whether the observed difference between sensitivities of wild-type KRAS cells and KRAS mutant cells, was statistically significant, the IC$_{50}$ data of the rela-tive sensitivity of human PDAC cell lines to TXNRD1 inhibition by auranofin was compared. As shown in FIG. 4A, a significant correlation was found between the anti-prolif-erative response to TXNRD1 inhibition and KRAS muta-tional status. In contrast, as shown in FIG. 4B-4C, there was a no significant correlation between the response to TXNRD1 inhibition and p53 mutational status or MYC mRNA expression. To understand the effect of KRAS muta-tions (G12C, G12D, G12V) on auranofin sensitivity, human pancreatic cancer cells harboring different KRAS mutations (G12C, G12D, G12V) or wild-type were treated with another TXNRD1 inhibitor piperlongumine. As shown in FIG. 4D, the KRAS mutant cells were more sensitive to piperlongumine than the wild-type KRAS cells, further reinforcing the above findings.

Figure 4E:
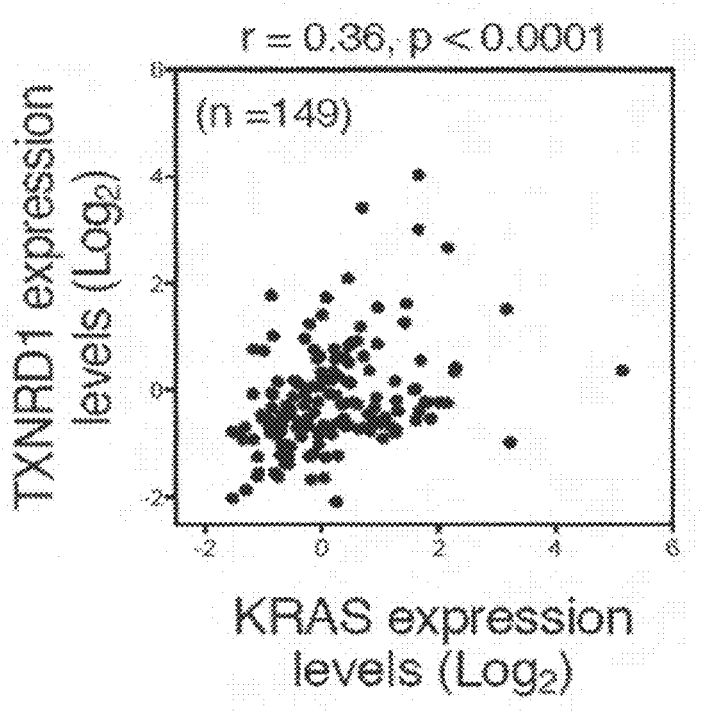
FIG. 4E shows a scatter plot illustrating the correlation between TXNRD1 and KRAS expression levels in TCGA human pancreatic cancer tumors (n=149).

To understand whether a correlation exists between expression of KRAS and TXIRD1, expression of both these genes was quantitated in 149 human pancreatic cancer tumors from the Cancer Genome Atlas Research Network (TCGA) and shown as a scatter plot. As shown in FIG. 4E, a correlation between expression of TXARD1 and KRAS expression levels was observed (r=0.36, p<0.0001).

Figure 4F:
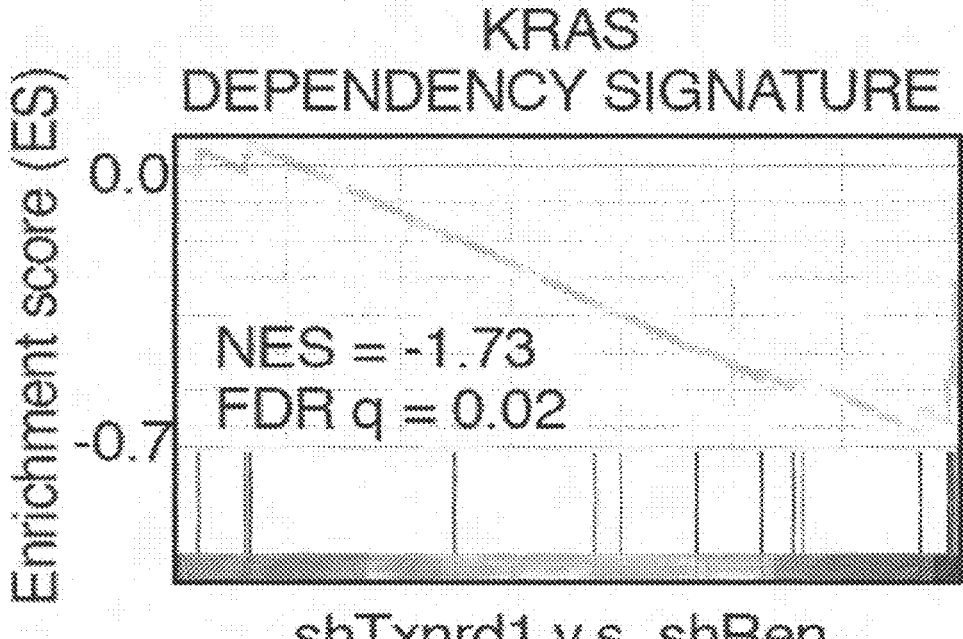
FIGS. 4F-4H show evaluation of changes in the gene signatures upon TXARD1 knockdown in mPDAC cells. Gene set enrichment analysis (GSEA) was used to evaluate changes in the gene signatures of KRAS dependency (FIG. 4F), pancreatic cancer (FIG. 4G), and Amino acid transporter/ferroptosis (FIG. 4H) upon TXARD1 knockdown in mPDAC cells compared to the cells harboring shRen (a non-targeting shRNA serving as a negative control).
Figure 4G:
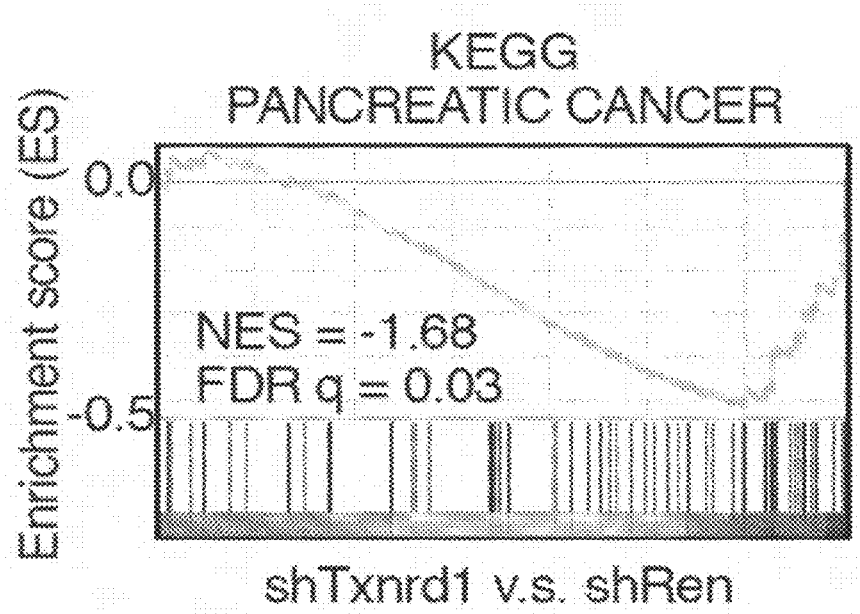
Figure 4H:
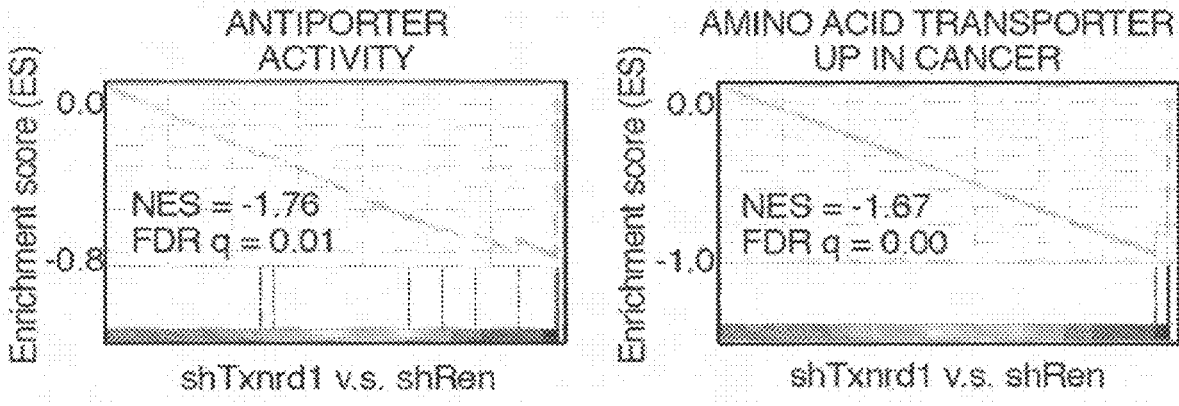

To understand the molecular mechanisms of TXNRD1 suppression in the PDAC cells, RNA-seq analyses of the mPDAC cells harboring shRNAs targeting control *Renilla* or Txnrd1 were performed. As shown in FIGS. 4F-4G, suppression of Cdk9 resulted in reversion of both KRAS dependency (FIG. 4F) and pancreatic cancer signatures (FIG. 4G), further validating the findings that TXNRD1 is required for KRAS oncogenic signaling. Interestingly, as shown in FIG. 411, suppression of TXNRD1 showed a downregulation of gene signatures related to amino acid transporter and ferroptosis including a gene called SLC7A11.

These results demonstrate that the TXNRD1 inhibitor compositions of the present technology are useful in methods for treating a disease or condition characterized by elevated levels of RAS expression and/or elevated levels of TXNRD1 expression in a subject in need thereof.

Example 7: TXNRD1 is Required for Maintenance of KRAS-Mutant Pancreatic Tumors

Figure 5A:
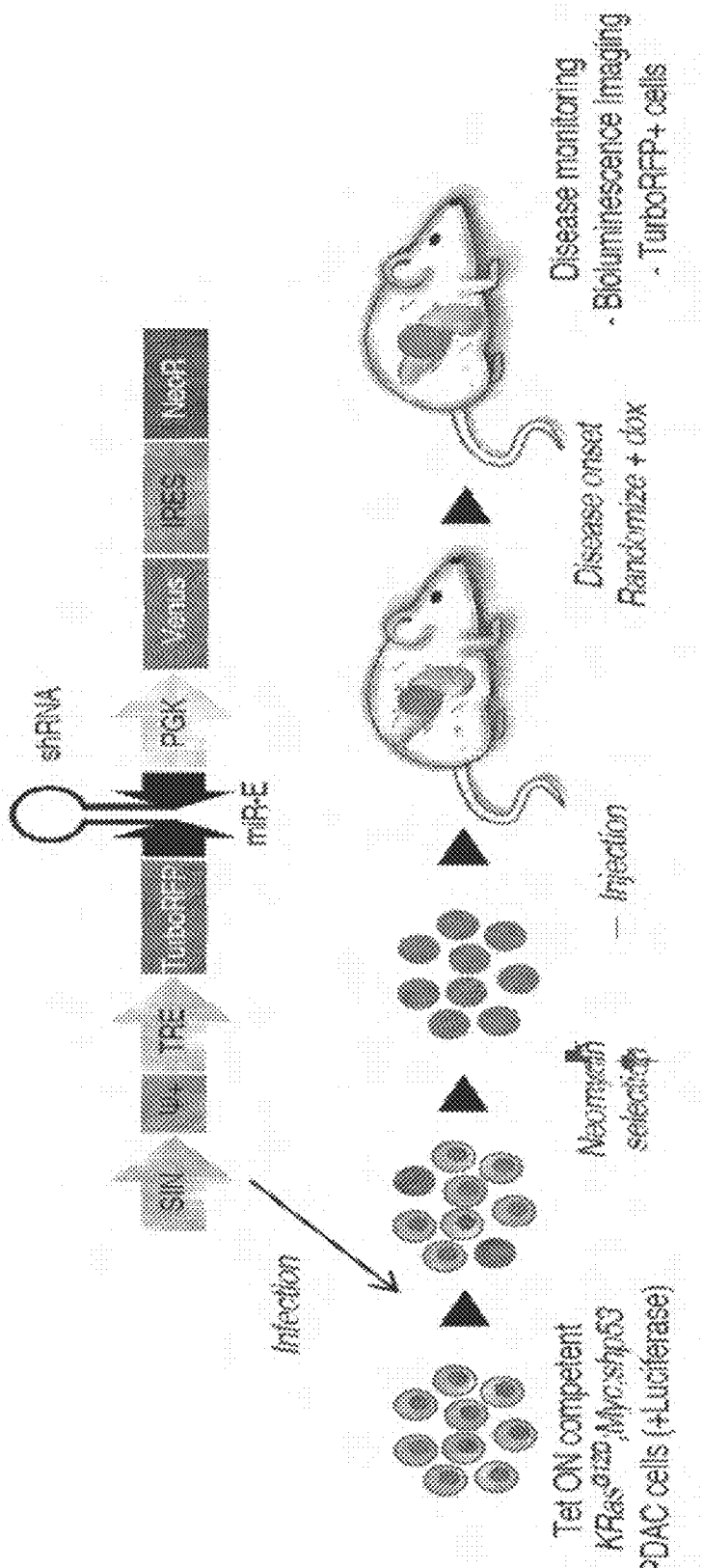
FIG. 5A shows a schematic representation of conditional RNAi experiments. Tet-On competent murine PDAC cells were transduced with TRMPV-Neo-miR-E shRNAs and a luciferase-hygro vector. The transduced cells were selected for G418 and hygromycin resistance, and transplanted into the pancreas of recipient mice. Upon disease onset, as determined using bioluminescent imaging (which typically occurred after seven days), shRNA expression was induced in a subset of mice by doxycycline (dox) supplementation in drinking water and chow.
Figure 5B:
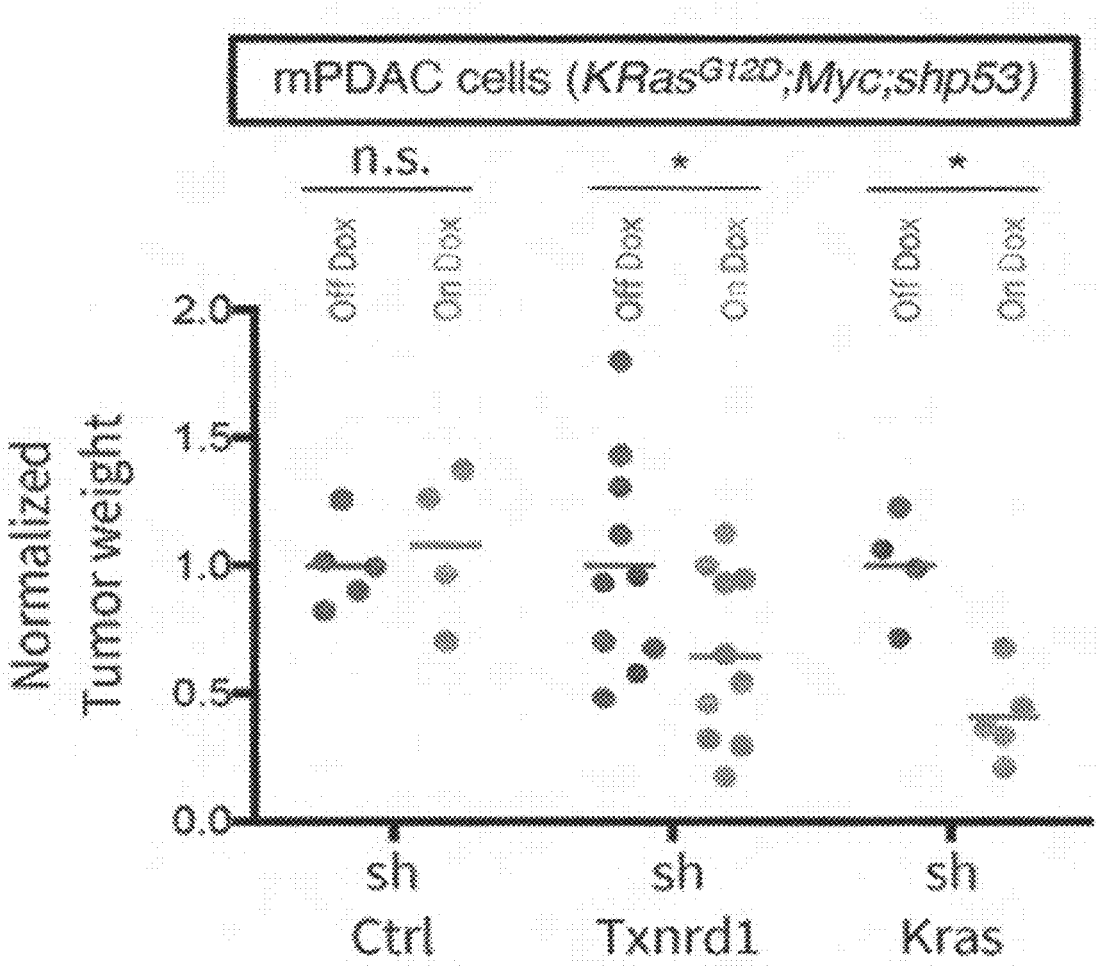
FIG. 5B shows a scatter plot illustrating tumor weights in animals treated with or without doxycycline to induce corresponding shRNAs (n=4-5).
Figure 5C:
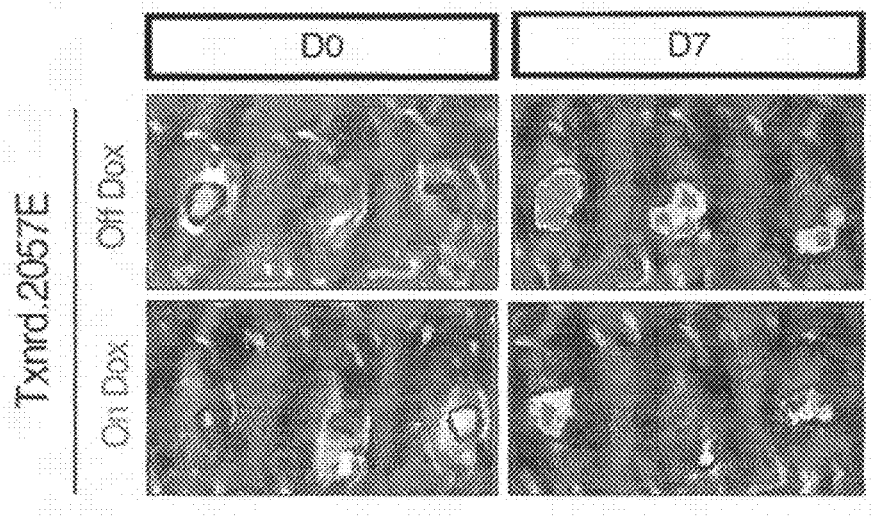
FIG. 5C shows bioluminescent imaging of representative mice orthotopically transplanted with mPDAC cells harboring the indicated TRMPV-Neo-miR-E shRNAs with and without dox treatment for 7 days. Dox was administered upon disease onset. Bioluminescent images on Day 0 (DO) and Day 7 (D7) are shown.

The relevance of TXNRD1 on PDAC progression in vivo was also investigated. To suppress Txnrd1 in established pancreatic tumors, mPDAC cells were transduced with Luciferase and dox inducible TRMPV-Neo-miR-E constructs containing Txnrd1 shRNAs or control shRNAs (Renilla and Kras) and were transplanted into the pancreas of recipient mice by orthotopic injection (See FIG. 5A). Upon detection of a luminescent signal, the animals were treated without or with dox to induce the corresponding shRNA expression. As shown in FIG. 5C, bioluminescent imaging revealed that mice from the untreated group (no dox) displayed large pancreatic tumors by day 7. In contrast, knockdown of Txnrd1 or Kras led to a comparable delay in tumor growth. Therefore, RNAi-mediated suppression of Txnrd1 approximates the effect of Kras inhibition in eliciting anti-tumor effects in Kras-mutant PDAC in vivo. Tumor weights were quantitated from animals treated with or without doxycycline to induce corresponding shRNAs (n=4-5). As shown in FIG. 5B, tumor weights from mice from the untreated group (no dox) displayed larger pancreatic tumors compared to the mice having knockdown of Txnrd1 or Kras led to a comparable delay in tumor growth. Weighs of tumors expressing Ren.713E were not affected by doxycycline treatment (compare the two sets of replicates in Ren.713 column of FIG. 5B). Weighs of tumors expressing Txnrd1 and KRAS shRNA were comparably inhibited by doxycycline treatment (compare the two sets of replicates between groups and within groups in Txnrd1.2057E, Txnrd1.1474E and KRas.247 columns of FIG. 5B).

These results demonstrate that the TXNRD1 inhibitor compositions of the present technology, such as an agent that inhibit expression of TXNRD1, are useful in methods for treating a RAS-mutant cancer in a subject in need thereof.

Figure 5D:
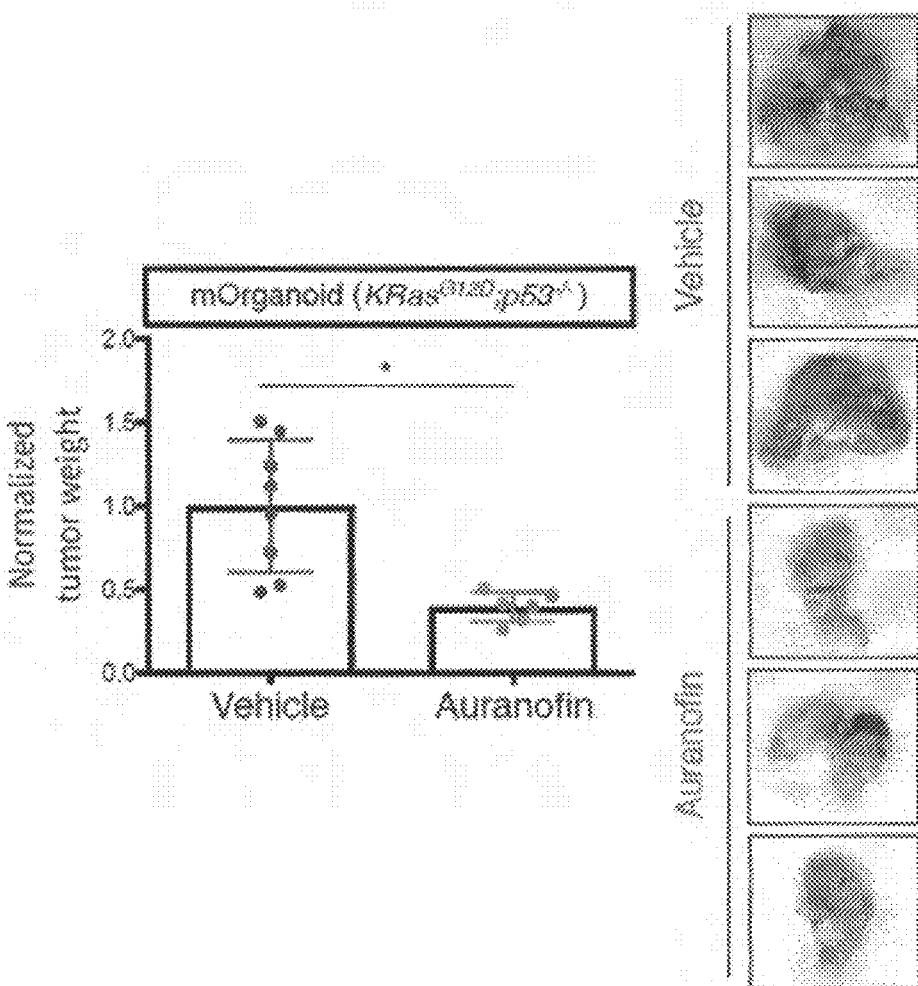
FIG. 5D shows a bar graph illustrating in vivo tumor weigh reduction caused by auranofin treatment. KRas$^{G12D}$; p53$^{-/-}$ organoids were transplanted in recipient mice, and the mice were treated with vehicle only or auranofin (n=3-4) for 1 week. Tumor weights were measured and plotted.
Figure 5E:
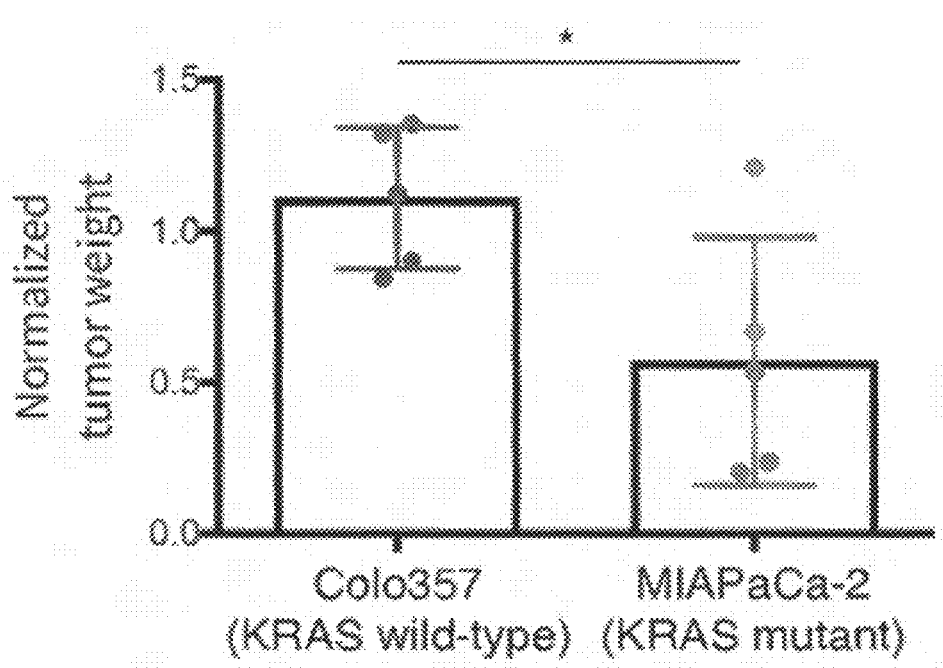
FIG. 5E shows a bar graph illustrating in vivo effects of auranofin treatment on human pancreatic cancer cell line tumor weights. MIAPaCa-2 (KRAS mutant) or Colo357 (KRAS wild-type) organoids were transplanted into the pancreases of recipient mice. The mice were treated with vehicle only or auranofin (n=5) for 2 weeks. Tumor weights were measured and plotted.

Growth inhibitory effects of pharmacological TXNRD1 inhibition was also examined in additional murine PDAC models generated by transplanting KRas$^{G}$12D; p53$^{-/-}$ pancreatic cancer organoid lines into the pancreas of recipient mice. Mice were treated either with vehicle only, acting as a negative control, or auranofin. As shown in FIG. 5D, consistent with the in vivo RNAi results (FIGS. 5A-5C), treatment with TXNRD1 inhibitor auranofin (10 mg/kg, one per day, 5 days per week) triggered a delay in Kras-mutant tumor growth. In addition, as shown in FIG. 5E, growth inhibitory effects of pharmacological TXNRD1 inhibition was found in human xenograft models generated by KRAS-mutant PDAC cells (MIAPaCa-2: KRAS mutant) but not in KRAS wild-type cells (Colo357: KRAS wild-type). Thus, TXNRD1 is required for the maintenance of KRAS-mutant tumors and dependency in vivo. FIG. 10 demonstrates that auranofin is delivered into the pancreas.

FIG. 9 demonstrates that patients with pancreatic adenocarcinoma (PDAC) who exhibit TXNRD1 mRNA upregulation show reduced overall survival compared with PDAC patients that express low levels of TXNRD1.

FIGS. 7A-7D show the antiproliferative effects of TXNRD1 inhibitor Auranofin in KRAS-mutant pancreatic cancer cells and potential synergistic inhibitory effects when combined with Gemcitabine. FIGS. 8A-8D show the antiproliferative effects of TXNRD1 inhibitor Auranofin in KRAS-mutant pancreatic cancer cells and potential synergistic inhibitory effects when combined with KRAS$^{G12C}$ inhibitor AMG 510.

These results demonstrate that the TXNRD1 inhibitor compositions of the present technology are useful in methods for treating a RAS-mutant cancer in a subject in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

What is claimed is:

1. A method for treating a RAS-mutant cancer in a subject in need thereof, comprising administering to the subject a therapeutically effective amount of a thioredoxin reductase 1 (TXNRD1) inhibitor selected from the group consisting of auranofin, Piperlongumine, (Diphenyl-2-thienylphosphine-κP) [2-(4-methoxyphenyl) ethynyl]gold (D9), 2-((4-Chlorophenyl) sulfonyl)-6-methoxy-3-nitropyridine (TRi-1), Myricetin, 4-(benzothiazol-2-yl)-4-hydroxycyclohexa-2,5-dienone (PMX464), 1-methylpropyl 2-imidazolyl disulfide (PX12), brevetoxin-2, manumycin A, ethaselen, aurothioglucose, protoporphyrin IX, an anti-TXNRD1 antibody, and Tri-2

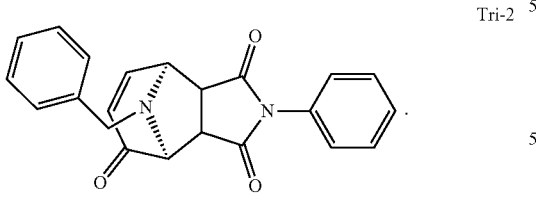

and an additional therapeutic agent, wherein the additional therapeutic agent is gemcitabine or a KRAS$^{G12C}$ inhibitor, wherein the KRAS$^{G12C}$ inhibitor is sotorasib (AMG 510).

2. The method of claim 1, wherein the subject displays elevated expression levels of RAS protein in cancer cells prior to treatment.

3. The method of claim 1, wherein the RAS-mutant cancer is lung cancer, mucinous adenoma, pancreatic cancer, col-orectal cancer, skin cancer, endometrial cancer, testicular germ cell cancer, or adrenal gland cancer.

4. The method of claim 3, wherein the RAS-mutant cancer comprises a KRAS, NRAS, or HRAS mutation selected from the group consisting of G12C, G12D, G12V, G12A, G12S, G12R, G13D, G13C, G13S, G13R, G13A, G13V, Q61H, Q61L, Q61R, Q61K, Q61P, and Q61E.

5. The method of claim 1, wherein the subject exhibits one or more signs or symptoms selected from among pain in the upper abdomen that radiates towards the back, loss of appetite or unintended weight loss, depression, new-onset diabetes, blood clots, fatigue, yellowing of skin and the whites of eyes (jaundice), bloating, nausea, and vomiting.

6. The method of claim 1, wherein the subject harbors one or more point mutations in TP53, CDKN2A, SMAD4, MLL3, TGFBR2, ARID1A, SF3B1, EPC1, ARID2, ATM, ZIM2, MAP2K4, NALCN, SLC16A4, MAGEA6, ROBO2, KDM6A, PREX2, ERBB2, MET, FGFR1, CDK6, PIK3R3, PIK3CA, BRCA1, BRCA2, or PALB2.

7. The method of claim 1, wherein the subject is human.

8. The method of claim 1, wherein the TXNRD1 inhibitor is administered orally, topically, intranasally, systemically, intravenously, subcutaneously, intraperitoneally, intradermally, intraocularly, iontophoretically, transmucosally, or intramuscularly.

9. The method of claim 1, wherein the TXNRD1 inhibitor or the inhibitory nucleic acid is administered daily for 6 weeks or more, or is administered daily for 12 weeks or more.

* * * * *